(12) United States Patent
Sporn et al.

(10) Patent No.: US 8,129,429 B2
(45) Date of Patent: Mar. 6, 2012

(54) SYNTHETIC TRITERPENOIDS AND METHODS OF USE IN THE TREATMENT OF DISEASE

(75) Inventors: Michael B. Sporn, Tunbridge, VT (US); Karen T. Liby, West Lebanon, NH (US); Gordon W. Gribble, Lebanon, NH (US); Tadashi Honda, Hanover, NH (US); Robert M. Kral, Grapevine, TX (US); Colin J. Meyer, Frisco, TX (US)

(73) Assignees: Reata Pharmaceuticals, Inc., Irving, TX (US); Trustees of Dartmouth College, Hanover, NH (US)

( * ) Notice: Subject to any disclaimer, the term of this patent is extended or adjusted under 35 U.S.C. 154(b) by 498 days.

(21) Appl. No.: 12/352,473

(22) Filed: Jan. 12, 2009

(65) Prior Publication Data

US 2009/0326063 A1  Dec. 31, 2009

Related U.S. Application Data

(60) Provisional application No. 61/020,624, filed on Jan. 11, 2008, provisional application No. 61/109,114, filed on Oct. 28, 2008.

(51) Int. Cl.
  *A61K 31/21* (2006.01)
(52) U.S. Cl. ........ 514/510; 514/511; 514/512; 514/506; 514/519; 558/429; 558/430; 558/440; 558/443
(58) Field of Classification Search .......... 514/510, 514/511, 512, 506, 519; 558/431, 429, 430, 558/440, 443
See application file for complete search history.

(56) References Cited

U.S. PATENT DOCUMENTS

| | | | | |
|---|---|---|---|---|
| 4,395,423 | A | 7/1983 | Neumann | 424/304 |
| 4,808,614 | A | 2/1989 | Hertel | 514/45 |
| 5,013,649 | A | 5/1991 | Wang et al. | 435/69.1 |
| 5,064,823 | A | 11/1991 | Lee et al. | 514/198 |
| 5,401,838 | A | 3/1995 | Chou | 536/281 |
| 5,426,183 | A | 6/1995 | Kjell | 536/285.5 |
| 5,464,826 | A | 11/1995 | Grindey et al. | 514/50 |
| 5,521,294 | A | 5/1996 | Wildfeur | 536/187 |
| 5,597,124 | A | 1/1997 | Kessel et al. | 241/30 |
| 5,603,958 | A | 2/1997 | Morein et al. | 424/489 |
| 5,606,048 | A | 2/1997 | Chou et al. | 536/271.1 |
| 5,972,703 | A | 10/1999 | Long et al. | 435/372 |
| 6,025,395 | A | 2/2000 | Breitner et al. | 514/570 |
| 6,303,569 | B1 | 10/2001 | Greenwald et al. | 514/2 |
| 6,326,507 | B1 | 12/2001 | Gribble et al. | 558/415 |
| 6,485,756 | B1 | 11/2002 | Aust et al. | 424/725 |
| 6,552,075 | B2 | 4/2003 | Gribble et al. | 514/522 |
| 6,890,946 | B2 | 5/2005 | Nakshatri et al. | 514/400 |
| 6,974,801 | B2 | 12/2005 | Honda et al. | 514/25 |
| 7,176,237 | B2 | 2/2007 | Honda et al. | 514/519 |
| 7,265,096 | B2 | 9/2007 | Gallop et al. | 514/49 |
| 7,288,568 | B2 | 10/2007 | Gribble et al. | 514/519 |
| 7,435,755 | B2 | 10/2008 | Konopleva et al. | 514/510 |
| 2003/0119732 | A1 | 6/2003 | Konopleva et al. | 514/510 |
| 2005/0276836 | A1 | 12/2005 | Wilson et al. | 424/434 |
| 2005/0288363 | A1 | 12/2005 | Gribble et al. | 558/303 |
| 2007/0155742 | A1 | 7/2007 | Honda et al. | 514/519 |
| 2007/0249561 | A1 | 10/2007 | Taylor | 514/79 |
| 2008/0220057 | A1 | 9/2008 | Gribble et al. | 514/522 |
| 2008/0233195 | A1 | 9/2008 | Sporn et al. | 514/63 |
| 2008/0261985 | A1 | 10/2008 | Honda et al. | 548/400 |
| 2009/0048204 | A1 | 2/2009 | Walling et al. | 514/49 |
| 2009/0048205 | A1 | 2/2009 | Meyer et al. | 514/49 |
| 2009/0060873 | A1 | 3/2009 | Sporn et al. | 424/85.6 |
| 2009/0093447 | A1 | 4/2009 | Konopleva et al. | 514/510 |

FOREIGN PATENT DOCUMENTS

| | | |
|---|---|---|
| DE | 10 2005 041613 | 3/2007 |
| EP | 0 272 891 A2 | 6/1988 |
| EP | 0 329 348 B1 | 7/1995 |
| EP | 0 376 518 B1 | 11/1995 |
| EP | 0 576 230 B1 | 4/1996 |
| EP | 0 577 303 B1 | 10/1997 |
| EP | 0 712 860 B1 | 12/2001 |
| JP | 2005/314381 | 11/2005 |
| JP | 2008-110962 | 5/2008 |
| JP | 2008-247898 | 10/2008 |
| WO | WO 91/15498 | 10/1997 |
| WO | WO 98/00173 | 1/1998 |
| WO | WO 98/32762 | 7/1998 |
| WO | WO 99/33483 | 7/1999 |
| WO | WO 99/65478 | 12/1999 |
| WO | WO 00/73253 | 12/2000 |
| WO | WO 01/01135 | 1/2001 |
| WO | WO 02/03996 | 1/2002 |
| WO | WO 02/47611 | 6/2002 |
| WO | WO 03/043631 | 5/2003 |
| WO | WO 03/059339 | 7/2003 |
| WO | WO 2005/042002 | 5/2005 |
| WO | WO 2005/046732 | 5/2005 |
| WO | WO 2006/029221 | 3/2006 |
| WO | WO 2008-016095 | 8/2006 |
| WO | WO 2007/005879 | 1/2007 |
| WO | WO 2007/069895 | 6/2007 |
| WO | WO 2008/111497 | 9/2008 |
| WO | WO 2008/136838 | 11/2008 |
| WO | WO 2009/023232 | 2/2009 |
| WO | WO 2009-058849 | 5/2009 |
| WO | WO 2010/093944 | 8/2010 |

OTHER PUBLICATIONS

International Search Report and Written Opinion issued in PCT/US2009/030771, dated Sep. 4, 2009.

(Continued)

*Primary Examiner* — Jeffrey S. Lundgren
*Assistant Examiner* — Ibrahim D Bori
(74) *Attorney, Agent, or Firm* — Fulbright & Jaworski L.L.P.

(57) ABSTRACT

The present invention concerns methods for treating and preventing renal/kidney disease, insulin resistance/diabetes, fatty liver disease, and/or endothelial dysfunction/cardiovascular disease using synthetic triterpenoids, optionally in combination with a second treatment or prophylaxis.

40 Claims, 15 Drawing Sheets

OTHER PUBLICATIONS

Shin et al., "NRF2 modulates aryl hydrocarbon receptor signaling: influence on adipogenesis," *Molecular and Cellular Biology*, 27:7188-7197, 2007.

Begum et al., "Synthesis of 2β-hydroxyursolic acid and other ursane analogs from ursonic acid," *Australian Journal of Chemistry*, 46 (7): 1067-1071, 1993.

Bowden et al., "Constituents of the fruit of *Pseudopanax arboreum* (Araliaceae)," *Australian J. of Chemistry*, 28 (1): 91-107, 1975.

Campbell et al., "Endocyclic α,β-unsaturated ketones. VI. Ultraviolet and infrared absorption spectra and resonance stabalization," *Bioorganic and Medicinal Chemistry Letters*, 7(13): 1623-1628, 1997.

Chattopadhyay et al., "Studies on autoxidation: Part IV. Synthesis of isomeric 2,3-diols of olean-I2-en-28-oate and isohopane (moretane)," *Indian J. of Chemistry, Section B: Organic Chemistry Including Medicinal Chemistry*, 15 (1): 21-24, 1977.

Devi et al., "Constituents of black dammar resin and some transformation products of α- and and β-amyrins," *Indian J. of Chemistry*, 7 (12): 1279-1280, 1969.

Elgamal et al., "Glycyrrhetic acid derivatives with modified ring A," *J. of Pharmaceutical Sciences*, 62 (9): 1557-1558, 1973.

Elgamal et al., "The C-2,C-3-glycol derivatives of glycyrrhetic acid," *Tetrahedron*, 30 (23/24): 4083-4087, 1974.

Endová et al., "Preparation of 2,3-secodiacids of the lupane series," *Collection of Czechoslovak Chemical Communications*, 59 (6): 1420-1429, 1994.

Evers et al., "Betulinic acid derivatives: a new class of human immunodeficiency virus type 1 specific inhibitors with a new mode of action," *J. of Medicinal Chemistry*, 39 (5): 1056-1068, 1996.

Ganguly et al., "Oxidation of ring in a lupeol," *Tetrahedron*, 22 (10): 3597-3599, 1966.

García-Granados et al., "Semi-synthesis of triterpene A-ring derivatives from oleanolic and maslinic acids. Theoretical and experimental $^{13}C$ chemical shifts," *J. of Chemical Research*, Synopses, 2: 56-57, 2000.

García-Granados et al., "Semi-synthesis of triterpene A-ring derivatives from oleanolic and maslinic acids. Part II. Theoretical and experimental $^{13}C$ chemical shifts," *J. of Chemical Research*, Synopses, 5: 211-212, 2000.

Glen et al., "Isolation of a new triterpenoid from rose-bay willowherb," *Chemistry and Industry*, London, United Kingdom), 46: 1908, 1965.

Govindachari et al., "Gymnosporol, a new pentacyclic triterpene from *Gymnosporia rothiana*," *Indian Journal of Chemistry*, 8 (5): 395-397, 1970.

Green and Long, "Compounds related to the steroid hormones. Part II. The action of hydrogen bromide on 2-bromo-3-oxo-$\Delta^1$-5α-steroids," *J. of the Chemical Society*, 2532-2543, 1961.

Hanna and Ourisson, "Studies of cyclic ketones. VIII. Preparation and properties of polycyclic α-diketones," *Bulletin de la Societe Chimique de France*, 1945-1951, 1961. (French only, but see attached English CAPLUS database summary.).

Hattori et al., "A triterpene from the fruits of *Rubus chingii*," *Phytochemistry*, 27 (12): 3975-3976, 1988.

Huneck, "Triterpene, XIV: die bromierung von 19β28-epoxy-3-oxo-2-diazo- und -1-oxo-2-diazo-sowie von 19β28-epoxy-1-oxo-18αH-oleanan," *Chemische Berichte*, 98 (9): 2837-2843, 1965. (German only, but see attached English CAPLUS database summary.).

Khan et al., "α-amyrin derivatives from *Corchorus depressus*," *Phytochemistry*, 30 (6): 1989-1992, 1991.

Klinot and Vystrcil, "Triterpenes. VII. Stereochemistry of 2-bromo derivatives of allobetuline and alloheterobetaline," *Collection of Czechoslovak Chemical Communications*, 31 (3): 1079-1092, 1966.

Klinot et al., "Triterpenes. Part LXXXVI. Triterpenoid 2,3-ketolis, diols and their acetates: preparation and conformation of the ring A," *Collection of Czechoslovak Chemical Communications*, 54 (2): 400-412, 1989.

Kumar and Seshadri, "Triterpenoids of *Pterocarpus santalinus*: constitution of a new lupene diol," *Phytochemistry*, 14 (2): 521-523, 1975.

Kundu et al., "Synthese von 2α-methoxycarbonyl-A-nor-lupa," *Chemische Beerichte*, 101 (9): 3255-3264, 1968. (German only, but see attached English CAPLUS database summary.).

Lavie and Shvo, "Constituents of *Ecballium elaterium*: proposed structure for elatericin A and B," *Chemistry and Industry*, (London, United Kingdom), 429-430, 1959.

Lawrie et al. "Isolation of derivatives of ursolic acid from apple skin," *Chemistry and Industry*, (London, United Kingdom), 41: 1720, 1966.

Lehn and Ourisson, "Syntheses in the lupane series," *Bulletin de la Societe Chimque de France*, 1133-1136, 1962. (French only, but see attached English CAPLUS database summary.).

Lehn and Vystreil, "Resonance magnetique nucleaire de produits naturels—VI : Triterpènes dérivés de la bétuline," *Tetrahedron*, 19 (11): 1733-1745, 1963. (English abstract).

Lehn and Ourisson, "Nuclear magnetic response (N.M.R.) of natural products. I. General introduction. Triterpenes of the lupane series. Methyl groups," *Bulletin de la Societe Chimique de France*, 1137-1142, 1962. (French only, but see attached English CAPLUS database summary.).

Li et al., "Studies on constituents of Rosa multiflora thunb," *Zhongguo Yaoke Daxue Xuebao*, 33 (3): 184-187, 2002. (Chinese only, but see attached English CAPLUS database summary.).

Lugemwa et al., "A heliothis zea antifeedant from the abundant birchbark triterpene betulin", *Journal of Agricultural and Food Chemistry*, 38 (2): 493-496, 1990.

Mane and Ingle, "Synthesis and biological activity of some new 1,5-benzothiazepines containing thiazole moiety: 2-aryl-4-(4-methyl-2-substituted-aminothiazol-5-y1)-2,3-dihydro-1, 5-benzothiazepines," *Indian Journal of Chemistry, Section B: Organic Chemistry Including Medicinal Chemistry*, 21B (10): 973-974, 1982.

Manzoor-i-Khuda and Habermehl, "Chemical constituents of *Corchorus capsularis* and *C. olitorium* (jute plant). III. Structure of corosin," *Zeitschrift fuer Naturforschung, Teil C: Biochemie, Biophysik, Biologie, Virologie*, 29 (5-6): 209-221, 1974.

Manzoor-i-Khuda, "Isolation techniques for active principles from plants and their composition and structure determination through spectroscopic techniques," *New Trends Nat. Prod*, 26: 303-323, 1986.

Misra et al., "Studies on autoxidation: Part II—synthesis of isomeric 2,3-diols of Δ12-oleanene," *Indian J. of Chemistry, Section B: Organic Chemistry Including Medicinal Chemistry*, 14B (6): 411-414, 1976.

Osman et al., "Application of chemical reactions on thin-layer chromatoplates. IV. Triterpene," *Bulletin of the Chemical Society of Japan*, 47 (8): 2056-2058, 1974.

Osman et al., "Chemical studies on pentacyclic triterpenes. I. Benzilic acid rearrangement of ring A in ursolic acid," *Egyptian J. of Chemistry*, 15 (3): 269-272, 1972.

Picard et al., "Structure of the triterpenes," *J. Soc. Chem. Ind.*, 58: 58-59, 1939.

Pitzele, "Synthesis of 2-oxygenated glycyrhetic acid derivatives," *J. of Medicinal Chemistry*, 117 (2): 191-194, 1974.

Pradhan and De, "Preparation of triterpenoid diosphenol via oximinoketone and structure of baccatin," *Indian J. of Chemistry, Section B: Organic Chemistry including Medicinal Chemistry*, 21B (9): 823-828, 1982.

Pradhan and Ghosh, "Studies on reactions of 2-bromo-3-ketotriterpenoids: Part IV. Debromination and dehydrobromination of 2α-bromo and 2,2-dibromo derivatives of lupanone and methyl dihydrobetulonate," *Indian J. of Chemistry, Section B: Organic Chemistry including Medicinal Chemistry*, 33B (1): 73-75, 1994.

Sejbal et al., "Triterpenes. Part LXXIII. Reactions of triterpenoid ketones with sulfur and morpholine under Willgerodt-Kindler reaction conditions," *Collection of Czechoslovak Chemical Communications*, 51 (1): 118-127, 1986.

Sejbal et al., "Triterpenes. Part XC. Conversion of betulin into careyagenolide (2α,3β-dihydroxy-18α, 19βH-ursan-28, 20β-olide," *Collection of Czechoslovak Chemical Communications*, 54 (4): 1036-1042, 1989.

Shimao and Oae, "The Wallach rearrangement of some 4,4'-disubstituted azoxybenzenes," *Bulletin of the Chemical Society of Japan*, 56 (2): 643-644, 1983.

Witz et al., "Cyclic ketones. XIII. Circular dichroism of steroid and triterpene ketones. Conformation of ring A of 8-methylated 3-oxotriterpenes," *Bull. Soc. China*, France: 1101-1112, 1963. (French only, but see attached English CAPLUS database summary.).

Liby et al., "The Synthetic Triterpenoids, CDDO and CDDO-Imidazolide Are Potent Inducers of Herne Oxygenase-1 and Nrf/ARE Signaling," *Cancer Research*, 65:4789-4798, 2005.

Office Communication issued in Japanese Patent Application No. 2010-542411, dated Jan. 17, 2011. (English translation).

Takahashi et al., "Organ protective role of heme oxygenase-1 against oxidative stress," *Folia Pharmacolgica Japonica*, 130:252-256, 2007. (English translation).

Takahashi et al., "Role of Stress Protein in Organopathy," *Renal and Intestinal Injury*, 30:359-365, 2006. (English Translation).

"CDDO in treating patients with metastatic or unresectable solid tumors or lymphoma," http://www.clinicaltrials.gov/ct2/show/NCT00352040?term=CDDO&rank=1, Dec. 14, 2008.

"FDA mulls drug to slow late-stage Alzheimer's," http://www.cnn.com/2003/HEALTH/conditions/09/24/alzheimers.drug.ap/index.html, Retrieved on Sep. 23, 2003.

"Phase IIa trail to determine the effects of bardoxolone methyl on renal function in patients with diabetic nephropathy," http://www.clinicaltrials.gov/ct2/show/NCT00664027?term=rta&rank=10, Dec. 14, 2008.

"RTA 402 in advanced solid tumors or lymphoid malignancies," http://www.clinicaltrials.gov/ct2/show/NCT00508807?term=rta&rank=2&show_desc=Y, Dec. 14, 2008.

"Study to assess the safety, tolerability, and pharmacodynamics of RTA 402 in patients with hepatic dysfunction," http://www.clinicaltrials.gov/ct2/show/NCT00550849?term=rta&rank=4, Dec. 14, 2008.

Abraham and Kappas, "Heme oxygenase and the cardiovascular-renal system," *Free Radic. Biol. Med.*, 39 (1): 1-25, 2005.

Agarwal and Mehta, "Possible involvement of Bcl-2 pathway in resinoid X receptor alpha-induced apoptosis of HL-60 cells," *Biochem Biophys Res Commun.*, 230(2):251-253, 1997.

Ahmad et al., "Triterpenoid CDDO-Me blocks the NF-κB pathway by direct inhibition of IKKβ on Cys-179", *J. Biol. Chem.*, 281:35764-9, 2006.

Akrivakis et al., "Prolonged infusion of gemcitabine in stage IV breast cancer: a phase I study," *Anti-Cancer Drugs*, 10 (6): 525-531, 1999.

Al-alami et al., "Divergent effect of taxol on proliferation, apoptosis and nitric oxide production in MHH225 CD34 positive and U937 CD34 negative human leukemia cells," *Leukemia Res.*, 22:939-945, 1998.

Alexander et al., "Synthesis and cytotoxic activity of two novel 1-dodecylthio-2-decyloxypropyl-3-phosphatidic acid conjugates with gemcitabine and cytosine arabinoside," *J. Med. Chem.*, 46 (19): 4205-4208, 2003.

Ambs et al., "p53 and vascular endothelial growth factor regulate tumor growth of NOS2-expressing human carcinoma cells," *Nat. Med.*, 4(12):1371-1376, 1998.

Amstutz et al., "Die position 5 im oxotremorin-gerust: eine zentrale stelle fur die steuerung der aktivitat am muscarinischen rezeptor," *Helv. Chim. Acta.*, 70:2232-2244, 1987.

Andreeff et al., "Expression of bcl-2-related genes in normal and AML progenitors: Changes induced by chemotherapy and cationic acid," *Leukemia*, 13:1881-1892, 1999.

Andreeff et al., "PPARgamma nuclear receptor as a novel molecular target in leukemias," *2002 Keystone Symposia*, Abstract No. 501, 2002.

Andreeff, "Acute myeloid leukemia," *In: Cancer Treatment*, Haskell (Ed.), W. B. Saunders, 911-922, 1995.

Araujo et al., "Systemic rather than local heme oxygenase-1 overexpression improves cardiac allograft outcomes in a new transgenic mouse," *J. Immunol.*, 171 (3): 1572-1580, 2003.

Ardestani et al., "Effects of dexamethasone and betamethasone as COX-2 gene expression inhibitors on rigidity in a rat model of Parkinson's disease," *Indian J. Pharmacol.*, 39:235-9, 2007.

Ariga et al., "Role of sphingolipid-mediated cell death in neurodegenerative diseases," *Journal of Lipid Research*, 39:1-16, 1998.

Bach, "Heme oxygenase-1 and transplantation tolerance," *Hum. Immunol.*, 67 (6): 430-432, 2006.

Baeuerle, "NF-κB: ten years after," *Cell*, 87:13-20, 1996.

Bagasra et al., "Activation of the inducible form of nitric oxide synthase in the brains of patients with multiple sclerosis," *Proc. Natl. Acad. Sci. USA*, 92:12041-12045, 1995.

Baker et al., "2'-Deoxy-2'-methylenecytidine and 2'-deoxy-2',2'-difluorocytidine 5'-diphosphates: potent mechanism-based inhibitors of ribonucleotide reductase," *J. Med. Chem.*, 34 (6): 1884, 1991.

Baldwin, Jr., "The NF-κB and IκB proteins: new discoveries and insights," *Annu. Rev. Immunol.*, 14:649-681, 1996.

Balkwill et al., "Smoldering and polarized inflammation in the initiation and promotion of malignant disease," *Cancer Cell*, 7 (3): 211-217, 2005.

Bargou et al., "Constitutive nuclear factor κB-RelA activation is required for proliferation and survival of Hodgkin's disease tumor cells," *J. Clin. Invest.*, 100:2961-2969, 1997.

Barkett and Gilmore, "Control of apoptosis by Rel/NF-κB transcription factors," *Oncogene*, 18:6910-6924, 1999.

Barnes and Karin, "Nuclear factor-κB—a pivotal transcription factor in chronic inflammation diseases," *N. Engl. J. Med.*, 336:1066-1071, 1997.

Beal, "Mitochondria, free radicals, and neurodegeneration," *Curr. Opin. Neurobiol.*, 6:661-666, 1996.

Beran et al., "Topotecan and cytarabine is an active combination regimen in myelodysplastic syndromes and chronic myelomonocytic leukemia," *J. Clinical Oncology*, 17(9):2819-2830, 1999.

Bliard et al., "Glycosylation of acids under phase transfer conditions. Partial synthesis of saponins," *Tetrahedron Lett.*, 35:6107-6108, 1994.

Bogdan et al., "Contrasting mechanisms for suppression of macrophage cytokine release by transforming growth factor-beta and interleukin-10," *J. Biol. Chem.*, 267:23301-23308, 1992.

Bogdan and Ding, "Taxol, a microtubule-stabilizing antineoplastic agent, induces expression of tumor necrosis factor α and interleukin-1 in macrophages," *J. Leukoc. Biol.*, 52(1):119-121, 1992.

Bollag and Holdener, "Retinoids in cancer prevention and therapy," *Annals of Oncology*, 3:513-526, 1992.

Boolbol et al., "Cyclooxygenase-2 overexpression and tumor formation are blocked by sulindac in a murine model of familial adenomatous polyposis," *Cancer Res.*, 56(11):2556-2560, 1996.

Bore et al., "The anti-inflammatory triterpenoid methyl 2-cyano-3, 12-dioxoolean 1,9(11)-dien-28-oate methanol solvate hydrate," Acta Crystallorg C., 58(Pt 3):o199-o200, 2002.

Brookes et al., "The triterpenoid 2-cyano-3,12-dioxooleana-1,9-dien-28-oic acid and its derivatives elicit human lymphoid cell apoptosis through a novel pathway involving the unregulated mitochondrial permeability transition pore," *Cancer Res.*, 67:1793-1802, 2007.

Bruder and Caplan, "First bone formation and the dissection of an osteogenic lineage in the embryonic chick tibia is revealed by monoclonal antibodies against osteoblasts," *Bone*, 10:359-375, 1989.

Bruder and Caplan, "A monoclonal antibody against the surface of osteoblasts recognizes alkaline phosphatase isoenzymes in bone, liver, kidney, and intestine," *Bone*, 11:189-198, 1990.

Bruder et al., "Terminal Osteogenic cell differentiation in culture requires beta-glycerol phosphate," *Trans. Ortho. Res. Soc.*, 16:58, 1991.

Bruland et al., "Expression and characteristics of a novel human osteosarcoma-associated cell surface antigen," *Cancer Res.*, 48:5302-5308, 1988.

Buzoni-Gatel et al., "Intraepithelial lymphocytes traffic to the intestine and enhance resistance to *Toxoplasma gondii* oral infection," *J. Immunol.*, 162:5846-5852, 1999.

Buzoni-Gatel et al., "Murine ileitis after intracellular parasite infection is controlled by TGF-beta-producing intraepithelial lymphocytes," *Gastroenterolog*, 120:914-924, 2001.

Cai and Vasella, "A new protecting group for alkynes: orthogonally protected dialkynes," *Helv. Chim. Acta.*, 78:732-757, 1995.

Carter et al., "Expression of survivin, a member of the inhibitor of apoptosis (IAP) family of caspase inhibitors is expressed in AML and regulated by cytokines and ATRA," *Blood*, 94(Suppl 1):479a, Abstract # 2142, 1999.

Cassady and Suffness, In *Anticancer Agents Based on Natural Product Models*; Academic Press, NY, 254-269, 1980.

Castaigne et al., "All-trans retinoic acid as a differentiation therapy for acute promyelocytic leukemia," *Blood*, 76(9):1704-1709, 1990.

Cerwenka and Swain, "TGF-β1: immunosuppressant and viability factor for T lymphocytes," *Microbes and Infection*, 1: 1291-1296, 1999.

Chauhan et al., "The bortezomib/proteasome inhibitor PS-341 and triterpenoid CDDO-Im induce synergistic anti-multiple myeloma (MM) activity and overcome bortezomib resistance," *Blood*, 103:3158-3166, 2004.

Chen et al., "Chondrogenesis in chick limb bud mesodermal cells: reciprocal modulation by activin and inhibin," *Exp. Cell. Res.*, 206:119-27, 1993.

Chen et al., "Stimulation of chondrogenesis in limb bud mesoderm cells by recombinant human bone morphogenetic protein 2B (BMP-2B) and modulation by transforming growth factor beta 1 and beta 2," *Exp. Cell. Res.*, 195:509-15, 1991.

Cheng et al., "Differentiation of human bone marrow osteogenic stromal cells in vitro: induction of the osteoblast phenotype by dexamethasone," *Endocrinology*, 134:277-86, 1994.

Chintharlapalli et al., "2-Cyano-3,12-dioxoolean-1,9-dien-28-oic acid and related compounds inhibit growth of colon cancer cells through peroxisome proliferator-activated receptor gamma-dependent and -independent pathways," *Mol. Pharmacol.*, 68:119-128, 2005.

Cho et al., "The transcription factor NRF2 protects against pulmonary fibrosis," *FASEB Journal*, 18:1-29, 2004.

Chou et al., "Sterospecific Synthesis of 2-Deoxy-2, 2-difluororibonolactone and its Use in the Preparation of 2'-Deoxy-2', 2'-difluoro-B—D-ribofuranosyl Pyrimidine Nucleosides: The Key Role of Selective Crystallization," *Synthesis*, 565-570, 1992.

Chung and Wasicak, "Synthesis of chiral ∀-acetylenic cyclic amines from ∀-amino acids: App.s to differentially constrained oxotremorine analogues as muscarinic agents," *Tetrahedron Lett.*, 31:3957-3960, 1990.

Cianchi et al., "Cyclooxygenase-2 activation mediates the proangiogenic effect of nitric oxide in colorectal cancer," *Clinical Cancer Research*, 10:2694-2704, 2004.

Clinton et al., "Steroidal[3,2-c]pyrazoles. II. Androstanes, 19-norandrostanes and their unsaturated analogs," *J. Am Chem Soc.*, 83:1478-1491, 1961.

Corey and Ruden, "Stereoselective methods for the synthesis of terminal *cis* AND *trans* enyne units," *Tetrahedron Lett.*, 1495-1499, 1973.

Coyle and Puttfarcken, "Oxidative stress, glutamate, and neurodegenerative disorders," *Science*, 262:689-695, 1993.

Cripe, "Adult Acute Leukemia," *Current Problems in Cancer*, 21 (1): 4-64, 1997.

Cui, "A material science perspective of pharmaceutical solids," *Int. J. Pharmceutics*, 339 (1-2): 3-18, 2007.

Dean et al., "Halogenolysis of methyl glycyrrhetate with lithium iodidedimethylformamide," *J. Chem. Soc.*, 6655-6659, 1965.

Dezube et al., "Interim results of a phase I trial with a novel orally administered synthetic triterpenoid RTA 402 (CDDO-Me) in patients with solid tumors and lymphoid malignancies," *J. Clin. Oncol.*, 2007 ASCO Annual Meeting Proceedings, 25(18S):14101, 2007.

Di Stefano et al., "Inhibition of [3H]thymidine incorporation into DNA of rat regenerating liver by 2',2'-difluorodeoxycytidine coupled to lactosaminated poly-L-lysine," *Biochem. Pharmacol.*, 57 (7): 793-799, 1999.

Ding et al., "Macrophage deactivating factor and transforming growth factors-$\beta_1$ $\beta_2$ and $\beta_3$, inhibit induction of macrophage nitrogen oxide synthesis by IFNγ[1]," *J. Immunol.*, 145:940-944, 1990.

Dinkova-Kostova et al., "Extremely potent triterpenoid inducers of the phase 2 response: correlations of protection against oxidant and inflammatory stress," *PNAS*, 102:4584-4589, 2005.

Drach et al., "Induction of differentiation in myeloid leukemia cell lines and acute promyelocytic leukemia cells by liposomal all-trans-retinoic acid," *Cancer Research*, 53:2100-2104, 1993.

Dragnev et al., "The retinoids and cancer prevention mechanisms," *The Oncologist*, 5:361-368, 2000.

Drefahl and Huneck, "Nor-olea-12-enol-17-amin und Olea-12-enol-28-amin," *Chem. Ber.*, 91:278-281, 1958.

DuBois et al., "$G_1$ delay in cells overexpressing prostaglandin endoperoxide synthase-2[1]," *Cancer Res.*, 56(4):733-737, 1996.

DuBois et al., "Increased cyclooxygenase-2 levels in carcinogen-induced rat colonic tumors," *Gastroenterology*, 110:1259-1262, 1996.

Dutcher et al., "Pentacyclic triterpene synthesis. 5. Synthesis of optically pure ring AB precursors," *J. Org. Chem.*, 41:2663-2669, 1976.

Ekmekcioglu et al., "Tumor iNOS predicts poor survival for stage III melanoma patients," *Int. J. Cancer*, 119:861-866, 2006.

Ellies et al., "Mammary tumor latency is increased in mice lacking the inducible nitric oxide synthase," *Int. J. Cancer*, 106:1-7, 2003.

Elliot et al., "The triterpenoid CDDO inhibits expression of matrix metalloproteinase-1, matrix metalloproteinase-13 and Bcl-3 in primary human chondrocytes," *Arthritis Res. Ther.*, 5:R285-R291, 2003.

Elsawa et al., "Preferential Inhibition of Malignant Cell Growth by CDDO in Waldenstrom Macroglobulinemia," *Blood*, 108(11):2528, 2006.

Elstner et al., "Ligands for peroxisome proliferator-activated receptorgamma and retinoic acid receptor inhibit growth and induce apoptosis of human breast cancer cells in vitro and in BNX mice," *Proc. Natl. Acad. Sci. USA*, 95:8806-8811, 1998.

Embleton et al., "Antitumour reactions of monoclonal antibody against a human osteogenic-sarcoma cell line," *Br. J. Cancer*, 43:4801-4805, 1981.

Engel et al., "Quantitation of minimal residual disease in acute myelogenous leukemia and myelodysplastic syndromes in complete remission by molecular cytogenetics of progenitor cells," *Leukemia*, 13:568-577, 1999.

Estey et al., "Molecular remissions induced by liposomal-encapsulated all-trans retinoic acid in newly diagnosed acute promyelocytic leukemia," *Blood*, 94:2230-2235, 1999.

Estey et al., "Randomized phase II study of fludarabine + cytosine arabinoside + idarubicin + all-trans retinoic acid + granulocyte-colony stimulating factor in poor prognosis newly diagnosed acute myeloid leukemia and myelodysplastic syndrom," *Blood*, 93(8):2478-2484, 1999.

Favaloro, Jr. et al., "Design and synthesis of tricyclic compounds with enone functionalities in rings A and C: a novel class of highly active inhibitors of nitric oxide production in mouse macrophages," *J Med Chem*, 45(22):4801-4805, 2002.

Finkbeiner and Stiles, "Chelation as a driving force in organic reactions. IV. Synthesis of a ∀-nitro acids by control of the carboxylastion-decarboxylation equilibrum," *J. Am. Chem. Soc.*, 85:616-622, 1963.

Gandhi et al., "Prolonged infusion of gemcitabine: clinical and pharmacodynamic studies during a phase I trial in relapsed acute myelogenous leukemia," *J. Clin. Oncol.*, 20 (3): 665-673, 2002.

Genain and Hauser, "Creation of a model for multiple sclerosis in *Callithrix jacchus* marmosets," *J. Mol. Med.*, 75:187-197, 1997.

Ghosh et al., "NF-κB and Rel proteins: evolutionarily conserved mediators of immune response," *Annu Rev Immunol.*, 16:225-260, 1998.

Godoy et al., "Central and systemic IL-I exacerbates neurodegeneration and motor symptoms in a model of Parkinson's disease," *Brain*, 131:1880-1894, 2008.

Grieco and Speake, "Synthetic Studies on Quassinoids: Total Synthesis and Biological Evaluation of (+)-Des-D-chaparrinone," *J. Org. Chem.*, 63:5929-5936, 1998.

Guo et al., "Selective Protection of 2',2'-Diflurodeoxycytidine (Gemcitabine)," *J. Org. Chem.*, 64: 8319-8322, 1999.

Guo et al., "Targeted delivery of a peripheral benzodiazepine receptor ligand-gemcitabine conjugate to brain tumors in a xenograft model," *Cancer Chemother. Pharmacol.*, 48 (2): 169-176, 2001.

Gura et al., "Systems for identifying new drugs are often faulty," *Science*, 278:1041-1042, 1997.

Guttridge et al., "NF-kappaB controls cell growth and differentiation through transcriptional regulation of cyclin D1," *Mol. Cell. Biol.*, 19 (8): 5785-5799, 1999.

Hail et al., "Evidence supporting a role for calcium in apoptosis induction by the synthetic triterpenoid 2-cyano-3,12-dioxooleana-1,9-dien-28-oic acid (CDDO)," *J. Biol. Chem.*, 279:11179-11187, 2004.

Heiner et al., "Localization of GD2-specific monoclonal antibody 3F8 in human osteosarcoma," *Cancer Res.*, 47:5377-5384, 1987.

Hidvegi et al., "A low temperature method of isolating normal human articular chondrocytes," *Osteoarthr. Cartil.*, 14:89-93, 2006.

Hinz et al., "NF-kappaB function in growth control: regulation of cyclin D1 expression and G0/G1-to-S-phase transition," *Mol. Cell. Biol.*, 19 (4): 2690-2698, 1999.

Hirota et al., "Stereoselective total synthesis of (±)-eperuane-8β,15-diol[1]," *Bull. Chem. Soc. Jpn.*, 61:4023-4028, 1988.

Hirota et al., "Suppression of tumor promoter-induced inflammation of mouse ear by ursolic acid and 4,4-dimethycholestane derivatives" *Agric. Biol. Chem.*, 54:1073-1075, 1990.

Hirota et al., "Total synthesis of (±)-amarolide, a quassinoid bitter principle," *J. Org. Chem.*, 56:1119-1127, 1991.

Honda et al., "A novel dicyanotriterpenoid, 2-cyano-3,12-dioxooleanan-1,9(11)-dien-28-onitrile, active at picomolar concentrations for inhibition of nitric oxide production," *Bioorganic & Medicinal Chemistry Letters*, 12:1027-1030, 2002.

Honda et al., "An efficient synthesis of tricyclic compounds (±)-(4aβ,8aβ,10aα)—1,2,3,4,4a,6,7,8,8a,9,1-,10a-Dodecahydro-1,1,4a-Trimethy1-2-Oxophenanthrene-8a-Carboxolic acid, its methyl ester, and (±)-(4aβ,8aβ,10aα)-3,4,4a,6,7,8,8a,9,10,10a-Decahydro-8a-Hydroxymethy1-1,1,4a-Trimethylphenanthren-2(1H)-one," *Org. Prep. Proced. Int.*, 37 (6):546-550, 2005.

Honda et al., "Design and synthesis of 2-cyano-3,12-dioxoolean-1,9-dien-28-oic acid, a novel and highly active inhibitor of nitric oxide production in mouse macrophages," *Bioorg Med Chem Lett.*, 8(19):2711-2714, 1998.

Honda et al., "Design, synthesis, and biological evaluation of biotin conjugates of 2-cyano-3,12-dioxooleana-1,9(11)-dien-28-oic acid for the isolation of the protein targets," *J. Med Chem.*, 47 (20): 4923-4932, 2004.

Honda et al., "Efficient synthesis of (−)- and (+)-tricyclic compounds with enome functionalities in rings a and C. A novel class of orally active anti-inflammatory and cancer chemopreventive agents," *Org Biomol Chem.*, 1:4384-4391, 2003.

Honda et al., "New enone derivatives of oleanolic acid and ursolic acid as inhibitors of nitric oxide production in mouse macrophages," *Bioorg. Med. Chem. Lett.*, 7:1623-1628, 1997.

Honda et al., "Novel synthetic oleanane and ursane triterpenoids with various enone functionalities in ring A as inhibitors of nitric oxide production in mouse macrophages," *J. Med. Chem.*, 43:1866-1877, 2000.

Honda et al., "Novel synthetic oleanane triterpenoids: a series of highly active inhibitors of nitric oxide production in mouse macrophages," *Bioorg Med Chem Lett*, 9(24):3429-3434, 1999.

Honda et al., "Novel tricyclic compounds having acetylene groups at C-8a and cyano enones in rings A and C: highly potent anti-inflammatory and cytoprotective agents," *J. Med. Chem.*, 50:1731-1734, 2007.

Honda et al., "Synthesis of (±)-3,3-ethylenedioxy-14α-hydroxy-5-picrasene-11,16-dione, a 14αH-picrasane derivative," *Chem. Lett.*, 299-302, 1981.

Honda et al., "Synthesis of a novel dicyano abietane analogue: a potential antiinflammatory agent," *J. Org. Chem.*, 71:3314-3316, 2006.

Honda et al., "Synthetic oleanane and ursane triterpenoids with modified rings A and C: A series of highly active inhibitors of nitric oxide production in mouse macrophages," *J. Med. Chem.*, 43:4231-4246, 2000.

Hong et al., "Phase I trial of a novel oral NF-κB/pSTAT3 inhibitor RTA-402 in patients with solid tumors and lymphoid malignancies," 44th Annual Meeting of the American Society of Clinical Oncology, 2008.

Hosoi et al., "Detection of human osteosarcoma-associated antigen(s) by monoclonal antibodies," *Cancer Res.*, 42:654-661, 1982.

Huang et al., "Inhibition of skin tumorigenesis by Rosemary and its constituents carnosol and ursolic acid," *Cancer Res.*, 54:701-708, 1994.

Huang et al., "Inhibitory effects of dietary curcumin on forestomach, duodenal, and colon carcinogenesis in mice," *Cancer. Res.*, 54:5841-5847, 1994.

Huang et al., "Structure of a WW domain containing fragment of dystrophin in complex with β-dystroglycan," *Nat. Struct. Biol.*, 7:634-638, 2000.

Hyer et al., "Synthetic triterpenoids cooperate with tumor necrosis factor-related apoptosis-inducing ligand to induce apoptosis of breast cancer cells," *Cancer Res.*, 65:4799-4808, 2005.

Iguchi et al., "Lipid peroxidation and disintegration of the cell membrane structure in cultures of rat lung fibroblasts treated with asbestos," *J. Appl. Toxicol.*, 13:269-275, 1993.

Ikeda et al., "Induction of redox imbalance and apoptosis in multiple myeloma cells by the novel triterpenoid 2-cyano-3,12-dioxoolean-1,9-dien-28-oic acid," *Mol. Cancer Ther.*, 3:39-45, 2004.

Ikeda et al., "The novel triterpenoid CDDO and its derivatives induce apoptosis by disruption of intracellular redox balance," *Cancer Res.*, 63:5551-5558, 2003.

Ishikawa et al., "Heme oxygenase-1 inhibits atherogenesis in Watanabe heritable hyperlipidemic rabbits," *Circulation*, 104 (15): 1831-1836, 2001.

Kerwin et al., "Quassinoid synthesis. 2. Preparation of a tetracyclic intermediate having the Bruceantin tetrahydrofuran ring," *J. Org. Chem.*, 52:1686-1695, 1987.

Khan et al., "A dichotomous role for nitric oxide during acute *Toxoplasma gondii* infection in mice," *Proc. Natl. Acad. Sci. USA*, 94:13955-13960, 1997.

Kim et al., "Capasase-3 activation is involved in apoptosis induced by a synthetic triterpenoid in Non-small cell lung cancer (NSCLC) cells," *Proc. Amer. Assoc. Cancer Res.*, 41:770, Abstract #4894, 2000.

Kim et al., "Identification of a novel synthetic triterpenoid, methyl-2-cyano-3,12-dioxooleana-1,9-dien-28-oate, that potently induces caspace-mediated apoptosis in human lung cancer cells," Molecular Cancer Therapeutics, 1:177-184, 2002.

Kircher, "Triterpenes, in organ pipe cactus," *Phytochemistry*, 19:2707-2712, 1980; Database CAPLUS on STN AN:1981:550946.

Klotz et al., "Selective expression of inducible nitric oxide synthase in human prostate carcinoma," *Cancer*, 82:1897-1903, 1998.

Konopleva and Andreeff, "Regulatory pathways in programmed cell death," *Cancer Mol Biol.*, 6:1229-1260, 1999.

Konopleva et al., "Activation of nuclear transcription factor PPARgamma by the novel triterpenoid CDDO as targeted therapy in breast cancer," *2002 Keystone Symposium*, Abstract No. 539, 2002.

Konopleva et al., "Apoptosis: molecules and mechanisms," *Adv Exp Med Biol*, 457:217-236, 1998.

Konopleva et al., "Engraftment potential of AML progenitors into NOD/scid mice is dependent on baseline CXCR4 expression," *Blood*, 94(Suppl 1):166b, Abstract #3916, 1999.

Konopleva et al., "Mechanisms and Activity of PPARgamma-Active Triterpenoids CDDO and CDDO-Me in Leukemias," *Blood*, 106:2460, 2005.

Konopleva et al., "Novel synthetic triterpenoid CDDO-Me: potent antiproliferative, proapoptotic and differentiating agent in AML," *Blood*, 96(11), Part 1: 121A, abstract # 522, 2000.

Konopleva et al., "Novel synthetic triterpenoid, CDDO, and its methyl ester: Potent antiproliferative, proapoptotic and differentiating agents in AML," *Blood*, 94(Suppl 1):479a, Abstract #2140, 1999.

Konopleva et al., "Novel triterpenoid CDDO-Me is a potent inducer of apoptosis and differentiation in acute myelogenous leukemia," *Blood*, 99(1):326-335, 2002.

Konopleva et al., "Peroxisome proliferator-activated receptor gamma and retinoid X receptor ligands are potent inducers of differentiation and apoptosis in leukemias," *Mol. Cancer Ther.*, 3:1249-1262, 2004.

Konopleva et al., "PPARγ nuclear receptor as a novel therapeutic target in AML," *Blood*, 96(11):460a, Abstract #1982, 2000.

Konopleva et al., "PPARgamma Ligand CDDO Induces Apoptosis in Leukemias Via Multiple Apoptosis Pathways," *Abstracts of the 44th Annual Meeting of the American Society of Hematology*, Abstract No. 2209, 2002.

Konopleva et al., "PPARgamma Ligands Are Potent Inducers of Apoptosis in Leukemias and Lymphomas," *American Society of Hematology 43rd Annual Meeting and Exposition*, Abstract No. 501, 2001.

Konopleva et al., "PPARgamma Nuclear Receptor as a Novel Molecular Target in Leukemia Therapy," *Proc. Amer. Assoc. Cancer Res.*, 43:4730, 2002.

Konopleva et al., "Suppression of ERK Activation is Required for Triterpenoid Methyl-CDDO-Induced Apoptosis in AML," *Blood*, 102(11):1404, 2003.

Konopleva et al., "Synthetic triterpenoid 2-cyano-3,12-dioxooleana-1,9-dien-28-oic acid induces growth arrest in HER2-overexpressing breast cancer cells," *Mol. Cancer Ther.*, 5:317-328, 2006.

Konopleva et al., "Synthetic triterpenoid CDDO as a novel therapy for resistant breast cancer," *Proc. Amer. Assoc. Cancer Res.*, 44:2726, 2003.

Konopleva et al., "The novel triterpenoid CDDO-Me suppresses MAPK pathways and promotes p38 activation in acute myeloid leukemia cells," *Leukemia*, 19:1350-1354, 2005.

Konopleva et al., "The synthetic triterpenoid 2-cyano-3,12-dioxooleana-1,9-dien-28-oic acid induces caspase-dependent and -independent apoptosis in acute myelogenous leukemia," *Cancer Res.*, 64:7927-7935, 2004.

Konopleva et al., "Triterpenoid methyl-CDDO s a potent inducer of apoptosis in CD34+ AML progenitor cells via activation of SAPK pathways and inhibition of MAPK cascades," *Blood*, 104:2533, 2004.

Kornblau et al., "Apoptosis regulating proteins as targets of therapy for hematological malignancies," *Exp. Opin. Inv. Drugs*, 8:2027-2057, 1999.

Kornblau et al., "Phase I study of mitoxantrone plus etoposide with multidrug blockage by SDZ PSC-833 in relapsed or refractory acute myelogenous leukemia," *J. Clin. Oncol.*, 15(5):1796-1802, 1997.

Kowalski and Reddy, "Ester homologation revisited: a reliable, higher yielding and better understood procedure," *J. Org. Chem.*, 57:7194-7208, 1992.

Kress et al., "Triterpenoids display single agent activity in a mouse model of CLL/SBL," *Blood*, 108(11):2530, 2006.

Kress et al., "Triterpenoids display single agent anti-tumor activity in a transgenic mouse model of chronic lymphocytic leukemia and small B cell lymphoma," *PLOS ONE*, 6(e559):1-11, 2007.

Kruger et al., "Up-regulation of heme oxygenase provides vascular protection in an animal model of diabetes through its antioxidant and antiapoptotic effects," *J. Pharmacol. Exp. Ther.*,319 (3): 1144-1152, 2006.

Kurbacher et al., "Ascorbic acid (vitamin C) improves the antineoplastic activity of doxorubicin, cisplatin, and paclitaxel in human breast carcinoma cells in vitro," *Cancer Lett.*, 103:183-189, 1996.

Kurinna et al., "The novel triterpenoid CDDO-Me promotes apoptosis in Gleevec-resistant chronic myeloid leukemia cells by caspase-independent mechanisms," *Proc. Amer. Assoc. Cancer Res.*, 46:2240, 2005.

Lala et al., "Role of nitric oxide in tumor progression: lessons from experimental tumors," *Cancer and Metastasis Reviews*, 17 (1): 91-106, 1998.

Langille et al., "Differential effects of physiological concentrations of retinoic acid in vitro on chondrogenesis and myogenesis in chick craniofacial mesenchyme," *Differentiation*, 40:84, 1989.

Lapillonne et al., "Activation of peroxisome proliferator-activated receptor gamma by a novel synthetic triterpenoid 2-cyano-3,12-dioxooleana-1,9-dien-28-oic acid induces growth arrest and apoptosis in breast cancer cells," *Cancer Res.*, 63:5926-5939, 2003.

Lawson et al., "Isolation and preliminary characterization of a monoclonal antibody that interacts preferentially with the liver isoenzyme of human alkaline phosphatase," *Clin. Chem.*, 31:381-385, 1985.

Lee et al., "Functional and quantitative analysis of splenic T cell immune responses following oral *Toxoplasma gondii* infection in mice," *Experimental Parasitology*, 91:212-221, 1999.

Lemieux, "Acylglycosyl Halides. [55] tetra-O-acetyl-α-D-glucopyranosyl bromide," *Methods Carbohydr. Chem.*, 2:221-222, 1963.

Leonard et al., "Expression of nitric oxide synthase in inflammatory bowel disease is not affected by corticosteroid treatment," *J. Clin. Pathol.*, 51:750-753, 1998.

Li and Nel, "Role of the Nrf2-mediated signaling pathway as a negative regulator of inflammation: implications for the impact of particulate pollutants on asthma," *Antioxidants & Redox Signaling*, 8:88-98, 2006.

Liby et al., "A novel acetylenic tricyclic bis-(cyano enone) potently induces phase 2 cytoprotective pathways and blocks liver carcinogenesis induced by aflatoxin," *Cancer Res.*, 68:6727-6733, 2008.

Liby et al., "The rexinoid LG100268 and the synthetic triterpenoid CDDO-methyl amide are more potent than erlotinib for prevention of mouse lung carcinogenesis," *Mol. Cancer Ther.*, 7:1251-1257, 2008.

Liby et al., "The synthetic triterpenoids, CDDO and CDDO-imidazolide, are potent inducers of heme oxygenase-1 and Nrf2/ARE signaling," *Cancer Res.*, 65:4789-4798, 2005.

Liby et al., "Triterpenoids and rexinoids as multifunctional agents for the prevention and treatment of cancer," *Nature Reviews Cancer*, 7:357-369, 2007.

Lieu et al., "Dual cytotoxic mechanisms of submicromolar taxol on human leukemia HL-60 cells," *Biochem. Pharmacology*, 53:1587-1596, 1997.

Ling et al., "The novel triterpenoid C-28 methyl ester of 2-cyano-3, 12-dioxoolen-1, 9-dien-28-oic acid inhibits metastatic murine breast tumor growth through inactivation of STAT3 signaling," *Cancer Res.*, 67:4210-4218, 2007.

Ling et al., "The novel triterpenoid CDDO-Me inhibits metastatic murine breast tumor through inhibition of Stat3 signaling," 2007 AACR Annual Meeting, Abstract No. 301, 2007.

Liotta et al., "A simple method for the efficient sysnthesis of unsaturated ∃-dicarbonyl compunds," *J. Org. Chem.*, 46:2920-2923, 1981.

Liu et al., "Herne oxygenase-1 (HO-1) inhibits postmyocardial infarct remodeling and restores ventricular function," *FASEB J.*, 20 (2): 207-216, 2006.

Long, "Regulation of human bone marrow-derived osteoprogenitor cells by osteogenic growth factors," *Clin. Invest.*, 95:881-887, 1995.

Luo et al., "IKK/NF-kappaB signaling: balancing life and death—a new approach to cancer therapy," *J. Clin. Invest.*, 115 (10): 2625-2631, 2005.

MacMicking et al., "Altered responses to bacterial infection and endotoxic shock in mice lacking inducible nitric oxide synthase," *Cell*, 81:641-650, 1995.

Mantovani et al., "Inflammation by remote control," *Nature*, 435:752-753, 2005.

Marnett, "Aspirin and the potential role of prostaglandins in colon cancer," *Cancer Res.*, 52(20):5575-5589, 1992.

Marrogi et al., "Nitric oxide synthase, cyclooxygenase 2, and vascular endothelial growth factor in the angiogenesis of non-small cell lung carcinoma," *Clinical Cancer Research*, 6:4739-4744, 2000.

Maurel et al., "Phase I trial of weekly gemcitabine at 3-h infusion in refractory, heavily pretreated advanced solid tumors," *Anti-Cancer Drugs*, 12 (9): 713-717, 2001.

McGeer and McGeer, "The inflammatory response system of brain: implications for therapy of Alzheimer and other neurodegenerative diseases," *Brain Research Reviews*, 21:195-218, 1995.

Mehta et al., "Activation of retinoid receptors RAR alpha and RXR alpha induces differentiation and apoptosis, respectively, in HL-60 cells," *Cell, Growth Differ*, 7(2): 179-186, 1996.

Melichar et al., "Growth-inhibitory effect of a novel synthetic triterpenoid, 2-cyano-3,12-dioxoolean-1,9-dien-28-oic acid, on ovarian carcinoma cell lines not dependent on peroxisome proliferator-activated receptor-gamma expression," *Gynecologic Oncology*, 93:149-154, 2004.

Mella et al., "1, 2-dideoxy-3, 4:5, 7-bis-*o*-(1-methylethylidene)-D-gluco- and -D-galacto-hept-1-ynitols : synthesis and conformational studies, " *Tetrahedron*, 44:1673-1678, 1988.

Merril and Benveniste, "Cytokines in inflammatory brain lesions: helpful and harmful," *Trends Neurosci.*, 19:331-338, 1996.

Minns et al., "A novel triterpenoid induces transforming growth factor beta production by intraepithelial lymphocytes to prevent ileitis," *Gastroenterology*, 127:119-126, 2004.

Mix et al., "A synthetic triterpenoid selectively inhibits the induction of matrix metalloproteinases 1 and 13 by inflammmatory cytokines," *Arthritis Rheum.*, 44:1096-1104, 2001.

Mix et al., "Peroxisome proliferator-activated receptor-gamma-independent repression of collagenase gene expression by 2-cyano-3,12-dioxooleana-1,9-dien-28-oic acid and prostaglandin 15-deoxy-delta(12,14) J2: a role for Smad signaling," *Mol. Pharmacol.*, 65:309-318, 2004.

Moncada et al., "Nitric oxide: physiology, pathophysiology, and pharmacology," *Pharmacol. Rev.*, 43:109-142, 1991.

Morris et al., "Association of a functional inducible nitric oxide synthase promoter variant with complications in type 2 diabetes," *J. Mol. Med.*, 80 (2): 96-104, 2002.

Morse and Choi, "Heme oxygenase-1: from bench to bedside," *Am. J. Respir. Crit. Care Med.*, 172 (6): 660-670, 2005.

Morse and Choi, "Heme oxygenase-1: the 'emerging molecule' has arrived," *Am. J. Respir. Crit. Care Med.*, 27(1):8-16, 2002.

Murphy et al., "Immunomodulatory Effects of the Triterpenoid CDDO after Allogeneic Bone Marrow Transplantation in Mice: Reduction of Acute Graft-Versus-Host Disease Lethality," *Blood*, 106:1316, 2005.

Murray and Zweifel, "Preparation of Phenyl Cyanate and Its Utilization for the Synthesis of α, β-Unsaturated Nitriles," *Synthesis*, 150-151, 1980.*Synthesis*, 150-151, 1980.

Muzart, "Synthesis of unsaturated carbonyl compounds via a chromium-mediated allylic oxidation by 70% tert.butylhydroperoxide," *Tetrahedron Lett.*, 28:4665-4668, 1987.

Na and Surh et al., "Transcriptional regulation via cysteine thiol modification: a novel molecular strategy for chemoprevention and cytoprotection," *Mol. Carcinog.*,45 (6): 368-380, 2006.

Nathan and Xie, "Nitric oxide synthases: roles, tolls, and controls," *Cell*, 78:915-918, 1994.

Nathan et al., "Protection from Alzheimer's-like disease in the mouse by genetic ablation of inducible nitric oxide synthase," *The Journal of Experimental Medicine*, 202:1163-1169, 2005.

Nathan, "Points of control in inflammation," *Nature*, 420:846-852, 2002.

Nicholson et al., "Lethality of endotoxin in mice genetically deficient in the respiratory burst oxidase, inducible nitric oxide synthase, or both," *Shock*, 11:253-258, 1999.

Nishino et al., "Inhibition of the tumor-promoting action of 12-O tetradecanoylphorbol-13-acetate by some oleanane-type triterpenoid compounds," *Cancer Res.*, 48:5210-5215, 1988.

Office Action, in Canadian Patent App. No. 2,335,505, mailed Jan. 10, 2008.
Office Action, in Canadian Patent App. No. 2,335,505, mailed Nov. 23, 2006.
Office Action, in Canadian Patent App. No. 2,335,505, mailed Sep. 22, 2008.
Office Action, in Canadian Patent App. No. 2,430,454, mailed Jan. 20, 2009.
Office Action, in European Patent App. No. 01 989 130, mailed Jul. 31, 2008.
Office Action, in European Patent App. No. 03 729 681, mailed Nov. 6, 2008.
Office Action, in European Patent App. No. 99 928 731, mailed Aug. 1, 2008.
Office Action, in European Patent App. No. 99 928 731, mailed Dec. 9, 2008.
Office Action, in European Patent App. No. 99 928 731, mailed Dec. 15, 2004.
Office Action, in European Patent App. No. 99 928 731, mailed Feb. 14, 2007.
Office Action, in U.S. Appl. No. 09/335,003, mailed Aug. 28, 2000.
Office Action, in U.S. Appl. No. 09/335,003, mailed Mar. 15, 2001.
Office Action, in U.S. Appl. No. 09/335,003, mailed Nov. 2, 2000.
Office Action, in U.S. Appl. No. 09/927,081, mailed Feb. 22, 2002.
Office Action, in U.S. Appl. No. 09/998,009, mailed Apr. 4, 2007.
Office Action, in U.S. Appl. No. 09/998,009, mailed Jul. 11, 2005.
Office Action, in U.S. Appl. No. 09/998,009, mailed Jul. 14, 2004.
Office Action, in U.S. Appl. No. 09/998,009, mailed Jul. 3, 2006.
Office Action, in U.S. Appl. No. 09/998,009, mailed Mar. 24, 2004.
Office Action, in U.S. Appl. No. 09/998,009, mailed Nov. 30, 2005.
Office Action, in U.S. Appl. No. 09/998,009, mailed Nov. 16, 2007.
Office Action, in U.S. Appl. No. 09/998,009, mailed Oct. 20, 2004.
Office Action, in U.S. Appl. No. 10/345,053, mailed Aug. 25, 2004.
Office Action, in U.S. Appl. No. 10/345,053, mailed Dec. 23, 2004.
Office Action, in U.S. Appl. No. 10/345,053, mailed Dec. 6, 2005.
Office Action, in U.S. Appl. No. 10/345,053, mailed Mar. 1, 2006.
Office Action, in U.S. Appl. No. 10/345,053, mailed May 31, 2005.
Office Action, in U.S. Appl. No. 10/395,372, mailed Apr. 28, 2006.
Office Action, in U.S. Appl. No. 10/395,372, mailed Aug. 4, 2005.
Office Action, in U.S. Appl. No. 10/395,372, mailed Dec. 20, 2006.
Office Action, in U.S. Appl. No. 10/395,372, mailed Feb. 7, 2007.
Office Action, in U.S. Appl. No. 10/395,372, mailed Jan. 28, 2004.
Office Action, in U.S. Appl. No. 10/395,372, mailed Jul. 9, 2004.
Office Action, in U.S. Appl. No. 10/395,372, mailed Jun. 12, 2006.
Office Action, in U.S. Appl. No. 10/395,372, mailed May 23, 2005.
Office Action, in U.S. Appl. No. 10/395,372, mailed Nov. 23, 2005.
Office Action, in U.S. Appl. No. 10/435,925, mailed Sep. 30, 2005.
Office Action, in U.S. Appl. No. 11/121,316, mailed Apr. 16, 2009.
Office Action, in U.S. Appl. No. 11/121,316, mailed Jul. 21, 2008.
Office Action, in U.S. Appl. No. 11/121,316, mailed Mar. 17, 2008.
Office Action, in U.S. Appl. No. 11/672,449, mailed Jun. 13, 2008.
Office Action, in U.S. Appl. No. 11/672,449, mailed Mar. 20, 2009.
Office Action, in U.S. Appl. No. 11/927,418, mailed Mar. 2, 2009.
Office Action, in U.S. Appl. No. 11/941,723, mailed Mar. 9, 2009.
Office Action, in U.S. Appl. No. 11/941,820, mailed Apr. 21, 2009.

Ohshima and Bartsch, "Chronic infections and inflammatory process as cancer risk factors: possible role of nitric oxide in carcinogenesis," *Mutat. Res.*, 305:253-264, 1994.

Omura and Swern, "Oxidation of Alcohols by 'Activated' Dimethyl Sulfoxide. A Preparative, Steric and Mechanistic Study," *Tetrahedron*, 34:1651-1660, 1978.

Ono et al., "A convenient procedure for esterification of carboxylic acids," *Bull. Chem. Soc. Jpn.*, 51:2401-2404, 1978.

Osburn et al., "Genetic of pharmacologic amplification of Nrf2 signaling inhibits acute inflammatory liver injury in mice," *Toxicological Sciences*, 104:218-227, 2008.

Oshima et al., "Suppression of intestinal polyposis in Apc$^{\Delta 716}$ knockout mice by inhibition of cyclooxygenase 2 (COX-2)," *Cell*, 87:803-809, 1996.

Pahl, "Activators and target genes of Rel/NF-κB transcription factors," *Oncogene*, 18:6853-6866, 1999.

Palcy and Goltzman, "Protein kinase signalling pathways involved in the up-regulation of the rat alpha1(I) collagen gene by transforming growth factor beta1 and bone morphogenetic protein 2 in osteoblastic cells," *Biochem. J.*, 343:21-27, 1999.

Patel et al., "Phase II clinical investigation of gemcitabine in advanced soft tissue sarcomas and window evaluation of dose rate on gemcitabine triphosphate accumulation," *J. Clin. Oncol.*, 19 (15): 3483-3489, 2001.

Paul et al., "Design and synthesis of a self-assembled photochemical dyad based on selective imidazole recognition," *Inorg. Chem.*, 41:3699-3704, 2002.

Paul et al., "Effective expression of small interfering RNA in human cells," *Nature Biotechnol.*, 20:505-508, 2002.

PCT, International Preliminary Examination Report, in Int. App. No. PCT/US1999/13635, mailed Sep. 6, 2000.
PCT, International Preliminary Examination Report, in Int. App. No. PCT/US2001/44541, mailed Jan. 15, 2004.
PCT, International Preliminary Examination Report, in Int. App. No. PCT/US2003/01307, mailed Oct. 20, 2003.
PCT, International Search Report and Written Opinion, in Int. App. No. PCT/US2008/073352, mailed Feb. 13, 2009.
PCT, International Search Report and Written Opinion, in Int. App. No. PCT/US2007/085010, mailed Apr. 16, 2008.
PCT, International Search Report and Written Opinion, in Int. App. No. PCT/US2007/071933, mailed Nov. 26, 2007.
PCT, International Search Report and Written Opinion, in Int. App. No. PCT/US2007/085010, mailed Apr. 16, 2008.
PCT, International Search Report, in Int. App. No. PCT/US1999/13635, mailed Oct. 20, 1999.
PCT, International Search Report, in Int. App. No. PCT/US2001/44541, mailed Jan. 24, 2003.

PCT, International Search Report, in Int. App. No. PCT/US2003/01307, mailed May 12, 2003.
PCT, International Search Report, in Int. App. No. PCT/US2003/14904, mailed Jul. 23, 2004.
PCT, Written Opinion, in Int. App. No. PCT/US1999/13635, mailed May 15, 2000.
PCT, Written Opinion, in Int. App. No. PCT/US2001/44541, mailed Sep. 23, 2003.
Pedersen et al., "The triterpenoid CDDO induces apoptosis in refractory CLL B cells," *Blood*, 100:2965-2972, 2002.
Petition Decision, issued in U.S. Appl. No. 10/345,053, mailed May 22, 2006.
Picard et al., "The triterpene resinols and related acids, part VI," *J. Chem. Soc.*, 1045-108, 1939.
Place et al., "The novel synthetic triterpenoid, CDDO-imidazolide, inhibits inflammatory response and tumor growth in vivo," *Clin. Cancer Res.*, 9:2798-2806, 2003.
Pollard, "Tumour-educated macrophages promote tumour progression and metastasis," *Nature Reviews*, 4:71-78, 2004.
Prescott and White, "Self-promotion? Intimate connections between APC and prostaglandin H synthase-2," *Cell*, 87:783-786, 1996.
Rangasamy et al., "Disruption of Nrf2 enhances susceptibility to severe airway inflammation and asthma in mice," *Journal of Experimental Medicine*, 202:47-59, 2005.
Rayet and Gelinas, "Aberrant rel/nfkb genes and activity in human cancer," *Oncogene*, 18:6938-6947, 1999.
Reddy et al., "Evaluation of cyclooxygenase-2 inhibitor for potential chemopreventive properties in colon carcinogenesis," *Cancer Res.*, 56(20):4566-4569, 1996.
Response to Office Action, in Canadian Patent App. No. 2,335,505, dated Jul. 10, 2008.
Response to Office Action, in Canadian Patent App. No. 2,335,505, dated May 11, 2007.
Response to Office Action, in European Patent App. No. 01 989 130, dated Sep. 5, 2008.
Response to Office Action, in European Patent App. No. 99 928 731, dated Oct. 1, 2008.
Response to Office Action, in European Patent App. No. 99 928 731, dated Mar. 9, 2009.
Response to Office Action, in European Patent App. No. 99 928 731, dated Jun. 23, 2005.
Response to Office Action, in European Patent App. No. 99 928 731, dated Aug. 14, 2007.
Response to Office Action, in U.S. Appl. No. 09/335,003, dated Sep. 28, 2000.
Response to Office Action, in U.S. Appl. No. 09/335,003, dated Mar. 2, 2001.
Response to Office Action, in U.S. Appl. No. 09/335,003, dated Apr. 16, 2001.
Response to Office Action, in U.S. Appl. No. 09/927,081, dated Jun. 24, 2002.
Response to Office Action, in U.S. Appl. No. 09/998,009, dated Apr. 21, 2004.
Response to Office Action, in U.S. Appl. No. 09/998,009, dated Sep. 14, 2004.
Response to Office Action, in U.S. Appl. No. 09/998,009, dated Apr. 19, 2005.
Response to Office Action, in U.S. Appl. No. 09/998,009, dated Oct. 11, 2005.
Response to Office Action, in U.S. Appl. No. 09/998,009, dated Mar. 30, 2006.
Response to Office Action, in U.S. Appl. No. 09/998,009, dated Jan. 3, 2007.
Response to Office Action, in U.S. Appl. No. 09/998,009, dated Sep. 4, 2007.
Response to Office Action, in U.S. Appl. No. 09/998,009, dated Feb. 18, 2008.
Response to Office Action, in U.S. Appl. No. 10/345,053, dated Sep. 24, 2004.
Response to Office Action, in U.S. Appl. No. 10/345,053, dated Mar. 23, 2005.
Response to Office Action, in U.S. Appl. No. 10/345,053, dated Sep. 3, 2005.
Response to Office Action, in U.S. Appl. No. 10/345,053, dated Feb. 6, 2006.
Response to Office Action, in U.S. Appl. No. 10/395,372, dated Apr. 28, 2004.
Response to Office Action, in U.S. Appl. No. 10/395,372, dated Nov. 9, 2004.
Response to Office Action, in U.S. Appl. No. 10/395,372, dated Jul. 25, 2005.
Response to Office Action, in U.S. Appl. No. 10/395,372, dated Nov. 23, 2005.
Response to Office Action, in U.S. Appl. No. 10/395,372, dated Apr. 21, 2006.
Response to Office Action, in U.S. Appl. No. 10/395,372, dated Oct. 12, 2006.
Response to Office Action, in U.S. Appl. No. 10/395,372, dated Jan. 12, 2007.
Response to Office Action, in U.S. Appl. No. 10/395,372, dated Feb. 14, 2007.
Response to Office Action, in U.S. Appl. No. 10/435,925, dated Mar. 30, 2005.
Response to Office Action, in U.S. Appl. No. 11/121,316, dated Apr. 4, 2008.
Response to Office Action, in U.S. Appl. No. 11/121,316, dated Dec. 19, 2008.
Response to Office Action, in U.S. Appl. No. 11/672,449, dated Dec. 15, 2008.
Response to Office Action, in U.S. Appl. No. 11/927,418, dated Apr. 2, 2009.
Response to Written Opinion, in Int. App. No. PCT/US1999/13635, dated Jul. 14, 2000.
Richardson et al., "Synthesis and restriction enzyme analysis of oligodeoxyribonucleotides containing the anti-cancer drug 2',2'-difluoro-2'-deoxycytidine," *Nucleic Acid Res.*, 20 (7): 1763-1769, 1992.
Rizzieri et al., "Phase I evaluation of prolonged-infusion gemcitabine with mitoxantrone for relapsed or refractory acute leukemia," *J. Clin. Oncol.*, 20 (3): 674-679, 2002.
Robbins et al., "Inflammation and Repair," *In*: Basic Pathology 3$^{rd}$ Edition, W.B. Saunders Company, Chapter 2, p. 28, 1981.
Rossi et al., "Anti-inflammatory cyclopentenone prostaglandins are direct inhibitors of IkappaB kinase," *Nature*, 403:103-108, 2000.
Ruvolo et al., "The novel triterpenoid methyl-CDDO inhibits Bc12 phosphorylation and potently kolls U937 cells," *Blood*, 94(10), Suppl. 1, Part 1: 280A, abstract #1251, 1999.
Sacerdoti et al., "Heme oxygenase overexpression attenuates glucose-mediated oxidative stress in quiescent cell phase: linking heme to hyperglycemia complications," *Curr. Neurovasc. Res.*, 2(2): 103-111, 2005.
Salvemini et al., "Endogenous nitric oxide enhances prostaglandin production in a model of renal inflammation," *J. Clin. Invest.*, 93(5):1940-1947, 1994.
Salvemini et al., "Nitric oxide activates cyclooxygenase enzymes," *Proc. Natl. Acad Sci. USA*, 90(15):7240-7244, 1993.
Samudio et al., "2,cyano-3,12 dioxoolean-1,9 diene-28-imidazolide induces apoptosis in pancreatic cancer via redox-dependent cytoplasmic stress," *Proc. Amer. Assoc. Cancer Res.*, 46: Abstract No. 5899, 2005.
Samudio et al., "2-Cyano-3,12-dioxooleana-1,9-dien-28-imidazolide (CDDO-Im) directly targets mitochondrial glutathione to induce apoptosis in pancreatic cancer," *J. Biol. Chem.*, 280:36273-36282, 2005.
Samudio et al., "A novel mechanism of action of methyl-2-cyano-3,12 dioxoolean-1,9 diene-28-oate: direct permeabilization of the inner mitochondrial membrane to inhibit electron transport and induce apoptosis," *Mol. Pharmacol.*, 69:1182-1193, 2006.
Samudio et al., "A novel mechanism of action of methyl-2-cyano-3,12 dioxoolean-1,9 diene-28-oate (CDDO-Me): Direct permeabilization of the inner mitochondrial membrane to inhibit electron transport and induce apoptosis," *Proc. Am. Assoc. Cancer Res.*, 47: Abstract No. 4693, 2006.
Samudio et al., "The novel triterpenoid CDDOme potently synergizes with inhibition of bcl-2 function to induce apoptosis in AML via disruption of intracellular redox homeostasis," *Proc. Amer. Assoc. Cancer Res.*, 46: Abstract No. 4955, 2005.
Satoh et al., "Activation of the Keap1/Nrf2 pathway for neuroprotection by electrophilic [correction of electrophillic] phase II inducers," *PNAS*, 103 (3): 768-773, 2006.
Scholz et al., "Sensitive and specific methods for the determination of CDDO methyl ester in mouse, rat, dog, monkey, and human plasma by LC-tandem mass spectrometry," *Proc. Amer. Assoc. Cancer Res.*, 4: Abstract No. 6321, 2003.
Seibert and Masferrer, "Role of inducible cyclooxygenase (COX-2) in inflammation," *Receptor*, 4(1):17-23, 1994.
Sharpless et al., "Electrophilic and nucleophilic organoselenium reagents. New routes to alpha, beta-unsaturated carbonyl compounds," *J. Am. Chem. Soc.*, 95:6137, 1973.
Sheng et al., "A selective cyclooxygenase 2 inhibitor suppresses the growth of H-ras-transformed rat intestinal epithelial cells," *Gastroenterology*, 113(6):1883-18891, 1997.
Sheng et al., "Inhibition of human colon cancer cell growth by selective inhibition of cyclooxygenase-2," *J. Clin. Invest.*, 99(9):2254-2259, 1997.
Shishodia et al., "A synthetic triterpenoid, CDDO-Me, inhibits IkappaBalpha kinase and enhances apoptosis induced by TNF and chemotherapeutic agents through down-regulation of expression of nuclear factor kappaB-regulated gene products in human leukemic cells," *Clin. Cancer Res.*, 12:1828-1838, 2006.
Shull et al., "Identification of a vitamin D-responsive protein on the surface of human osteosarcoma cells," *Proc. Natl. Acad. Sci. USA*, 86:5405-5410, 1989.
Shull et al., "Morphologic and biochemical studies of canine mucopolysaccharidosis I," *Am. J. Pathol.*, 114:487-495, 1984.
Simonian and Coyle, "Oxidative stress in neurodegenerative diseases," *Annu. Rev. Pharmacol. Toxicol.*, 36:83-106, 1996.
Simonsen et al., "Tetracyclic hydroxy acids," In *the Terpenes*, Cambridge University, Cambridge, 5:221-285, 1957.
Singh and Evans, "Nitric oxide, the biological mediator of the decade: fact or fiction?" *Eur. Respir. J.*, 10:699-707, 1997.
Singh et al., "Anti-inflammatory activity of oleanolic acid in rats and mice," *J. Pharm.Pharmacol.*, 44:456-458, 1992.
Sive et al., "Expression of chondrocyte markers by cells of normal and degenerate intervertebral discs," *Mol. Pathol.*, 55:91-97, 2002.
Snitman et al., "Synthetic approaches to taxodione synthesis of methyl 12-oxopodocarpa-5,9(11)-diene-8β-carboxylate," *Synth. Comm.*, 8:187-194, 1978.
Sonogashira et al., "A convenient synthesis of acetylenes: catalytic substitutions of acetylenic hydrogen with bromoakenes, iodoarenes, and bromopyridines," *Tetrahedron Lett.*, 4467-4470, 1975.
Sporn and Roberts, "Peptide growth factors and inflammation, tissue repair, and cancer," *J. Clin. Invest.*, 78:329-332, 1986.
Sporn et al., "Prospects for prevention and treatment of cancer with selective PPARγ modulators (SPARMs)," *Trends in Molecular Medicine*, 7(9):395-400, 2001.
Sporn et al., "Transforming growth factor-beta: biological function and chemical structure," *Science*, 233:532-534, 1986.
Stadheim et al., "The novel triterpenoid 2-cyano-3,12-dioxooleana-1,9-dien-28-oic acid (CDDO) potently enhances apoptosis induced by tumor necrosis factor in human leukemia cells," *J. Biol. Chem.*, 277:16448-16455, 2002.
Steadman's Medical Journal 23$^{rd}$ Edition, The Williams & Wilkins Company, p. 401, 1976.
Sterzycki, "Pyrodinium tosylate, a mild catalyst for formation and cleavage of dioxolane-type acetals," *Synthesis*, 724-725, 1979.
Stewart et al., "Risk of Alzheimer's disease and duration of NSAID use" *Neurology*, 48:626-632, 1997.
Strejan et al., "Suppression of chronic-relapsing experimental allergic encephalomyelitis in strain-13 guinea pigs by administration of liposome-associated myelin basic protein," *J. Neuroimmunol.*, 7 (1): 27, 1984.
Suh et al., "A novel synthetic oleanane triterpenoid, 2-cyano-3,12-dioxoolean-1,9-dien-28-oic acid, with potent differentiating, antiproliferative, and anti-inflammatory activity," *Cancer Res.*, 59(2):336-341, 1999.
Suh et al., "A novel synthetic oleanane triterpenoid, 2-cyano-3,12-dioxoolean-1,9-dien-28-oic acid (CDDO), induces cell differentiation in human myeloid leukemias," *Proceedings of the American Association for Cancer Research Annual Meeting*, 40:300, abstract # 1988, 1999.
Suh et al., "Novel triterpenoids suppress inducible nitric oxide synthase (iNOS) and inducible cyclooxygenase (COX-2) in mouse macrophages," *Cancer Research*, 58:717-723, 1998.
Suh et al., "Novel triterpenoids suppress inducible nitric oxide synthase (iNOS) and inducible cyclooxygenase (COX-2)," *Proceedings of the American Association for Cancer Research Annual Meeting*, 39: Abstract No. 1821, 1998.
Suh et al., "Synthetic triterpenoids activate a pathway for apoptosis in AML cells involving downregulation of FLIP and sensitization to TRAIL," *Leukemia*, 17:2122-2129, 2003.
Suh et al., "Synthetic triterpenoids enhance transforming growth factor β/Smad signaling," *Cancer Res.*, 63:1371-1376, 2003.
Suh et al., "Triterpenoids CDDO and CDDO-Me Down-Regulate FLIP Expression and Sensitize AML Cells to Trail-Induced Apoptosis," *American Society of Hematology 43$^{rd}$ Annual Meeting and Exposition*, Abstract No. 498, 2001.
Suh et al., "New triterpenoids as cancer preventive and anti-inflammatory agents," *Proceedings of the American Association for Cancer Research*, Abstract No. 1457, 38: 216, 1997.
Supplementary European Search Report, issued in European Patent App. No. 01 989 130, mailed Aug. 9, 2007.
Supplementary European Search Report, issued in European Patent App. No. 03 729 681, mailed Aug. 3, 2006.
Sun et al., "The synthetic triterpenoid, CDDO, suppresses alloreactive T cell responses and reduces murine early acute graft-versus-host disease mortality," *Biology of Blood and Marrow Transplantation*, 13:521-529, 2007.
Sussan et al., "Disruption of Nrf2, a key inducer of antioxidant defenses, attenuates ApoE-mediated atherosclerosis in mice," *PLoS One*, 3 (11): 1-9, 2008.
Syftestad et al., "The in vitro chondrogenic response of limb-bud mesenchyme to a water-soluble fraction prepared from demineralized bone matrix," *Differentiation*, 29:230, 1985.
Tabe et al., "Chromatin-Mediated Transcriptional Activation with Novel Peroxisome Proliferator—Activated Receptor gamma(P-PARgamma) Ligand 2-cyano-1,9-dien-28-oic Acid (CDDO) in Acute Promyelocytic Leukemia Cells," *Abstracts of the 44$^{th}$ Annual Meeting of the American Society of Hematology*, Abstract No. 2191, 2002.
Takabe et al., "Synthesis of lycosyl esters of oleanolic," *Carbohydrate Research*, 76:101-108, 1979, Database CAPLUS on STN AN:1980:42278.
Takahashi et al., "Increased expression of inducible and endothelial constitutive nitric oxide synthases in rat colon tumors induced by azoxymethane," *Cancer Res.*, 57:1233-1237, 1997.
Tamir and Tannebaum, "The role of nitric oxide (NO) in the carcinogenic process," *Biochim. Biophys. Acta*, 1288:F31-F36, 1996.
Tamm et al., "Expression and prognostic significance of IAP-family genes in human cancers and leukemias," *Blood*, 94(Suppl. 1):69a, Abstract # 298, 1999.
Tempero et al., "Randomized phase II comparison of dose-intense gemcitabine: thirty-minute infusion and fixed dose rate infusion in patients with pancreatic adenocarcinoma," *J. Clin. Oncol.*, 21 (18): 3402-3408, 2003.
Tenenbaum and Heersche, "Differentiation of osteoblasts and formation of mineralized bone in vitro," *Calcif. Tissue Int.*, 34:76, 1982.
Therasse et al., "New guidelines to evaluate the response to treatment in solid tumors. European Organization for Research and Treatment of Cancer, National Cancer Institute of the United States, National Cancer Institute of Canada," *J. Natl. Cancer Instit.*, 92 (3): 205, 2000.
Thimmulappa et al., "Nrf2 is a critical regulator of the innate immune response and survival during experimental sepsis," *J. Clinical Investigation*, 116 (4): 984-995, 2006.
Thimmulappa et al., "Nrf2-dependent protection from LPS induced inflammatory response and mortality by CDDO-imidazolide," *Biochem. Biophys. Res. Commun.*, 351:883-889, 2006.
Thimmulappa et al., "Preclinical evaluation of targeting the Nrf2 pathway by triterpenoids (CDDO-Im and CDDO-Me) for protection from LPS-induced inflammatory response and reactive oxygen species in human peripheral blood mononuclear cells and neutrophils," *Antioxidants & Redox Signaling*, 9:1-8, 2007.

Toriumi et al., "Mandibular reconstruction with a recombinant bone-inducing factor. Functional, histologic, and biomechanical evaluation," *Arch. Otolaryngol. Head Neck Surg.*, 117:1101-1112, 1991.

Torres et al., "Inflammation and nitric oxide production in skeletal muscle of type 2 diabetic patients," *Journal of Endocrinology*, 181:419-427, 2004.

Tran et al., "The synthetic triterpenoid CDDO-methyl ester modulates microglial activities, inhibits TNF production, and provides dopaminergic neuroprotection," *Journal of Neuroinflammation*, 5:1-14, 2008.

Tsai et al., "Monoclonal antibody to human osteosarcoma: a novel Mr 26,000 protein recognized by murine hybridoma TMMR-2," *Cancer Res.*, 50:152-161, 1990.

Tsao et al., "DRIP205 co-activator overexpression enhances PPARgamma-mediated differentiation of leukemia cells by CDDO," *Proc. Amer. Assoc. Cancer Res.*, 46: Abstract No. 1855, 2005.

Tsao et al., "Targeted Induction of Apoptosis in Leukemias by PPARgammma Ligation," *American Society of Hematology 43$^{rd}$ Annual Meeting and Exposition*, Abstract No. 2381, 2001.

Tsujii and DuBois, "Alterations in cellular adhesion and apoptosis in epithelial cells overexpressing prostglandin endoperoxide synthase 2," *Cell*, 83(3):493-501, 1995.

Tsujii et al., "Cyclooxygenases regulates angiogenesis induced by colon cancer cells," *Cell*, 93:705-716, 1998.

Turksen et al., "Isolation of monoclonal antibodies recognizing rat bone-associated molecules in vitro and in vivo," *J. Histochem. Cytochem.*, 40:1339-1352, 1992.

U.S. Appl. No. 12/426,737, filed Apr. 20, 2009.
U.S. Appl. No. 12/426,778, filed Apr. 20, 2009.
U.S. Appl. No. 12/426,791, filed Apr. 20, 2009.
U.S. Appl. No. 12/426,832, filed Apr. 20, 2009.
U.S. Appl. No. 12/426,889, filed Apr. 20, 2009.
U.S. Appl. No. 60/955,939, filed Aug. 15, 2007.

Van Muiswinkel and Kuiperij, "The Nrf2-ARE signaling pathway: promising drug target to combat oxidative stress in neurodegenerative disorders," *Current Drug Target—CNS & Neurological Disorders*, 4:267-281, 2005.

Vazquez et al., "Human immunodeficiency virus type 1-induced macrophage gene expression includes the p21 gene, a target for viral regulation," *J. Virol.*, 79:4479-4491, 2005.

Veerman et al., "Antitumor activity of prolonged as compared with bolus administration of 2',2'-difluorodeoxycytidine in vivo against murine colon tumors," *Cancer Chemother. Pharmacol.*, 38 (4): 335-342, 1996.

Vodovotz et al., "Inducible nitric oxide synthase in tangle-bearing neurons of patients with Alzheimer's Disease," *The Journal of Experimental Medicine*, 184:1425-1433, 1996.

Vukicevic et al., "Stimulation of the expression of osteogenic and chondrogenic phenotypes in vitro by osteogenin," *Proc. Natl. Acad. Sci. USA*, 86:8793-7, 1989.

Walczak et al., "Tumoricidal activity of tumor necrosis factor-related apoptosis-inducing ligand in vivo", *Nature Medicine*, 5(2):157-163, 1999.

Walsh et al., "Monoclonal antibodies with selective reactivity against osteoblasts and osteocytes in human bone," *J. Bone Miner Res.*, 9:1687-1696, 1994.

Wang et al., "A novel synthetic triterpenoid, 2-cyano-3,12-dioxoolean-1,9-dien-28-oic acid (CDDO) induces adipocyte differentiation in 3T3-L1 cells," *Proceedings of the American Association for Cancer Research Annual Meeting*, 40:300, abstract # 1989, 1999.

Wang et al., "A synthetic triterpenoid, 2-cyano-3,12-dioxooleana-1,9-dien-28-oic acid (CDDO), is a ligand for the peroxisome proliferator-activated receptor γ," *Mol. Endocrin.*, 14(10):1550-1556, 2000.

Wang et al., "Synthetic triterpenoid CDDO and its derivatives increase ceramides and are cytotoxic to pediatric acute lymphoblastic leukemia cell lines," *Proc. Am. Assoc. Cancer Res.*, 47: 4643, 2006.

Warrell et al., "Differentiation therapy of acute promyelocytic leukemia with tretinoin (all-trans-retinoic acid)," *N. Engl. J. Med.*, 324(20):1385-1393, 1991.

Williams et al., "Immunology of multiple sclerosis," *Clin. Neurosci.*, 2(3-4):229-245, 1994.

Woodley, "Liposomes for Oral Administration of Drugs," *Crit. Rev. Therapeutic Drug Carrier System*, 2(1):1-18, 1995.

Xie et al., "Differential expression patterns in human myeloblastic leukemia HL-60 and multidrug resistant HL-60/Dox cells analyzed by human cDNA expression array," *Blood*, 92 (Suppl 1):387a, Abstract #1600, 1998.

Yates et al., "Pharmacodynamic characterization of chemopreventive triterpenoids as exceptionally potent inducers of Nrf2-regulated genes," *Mol. Cancer Ther.*, 6:154-162, 2007.

Yates et al., "Potent protection against aflatoxin-induced tumorigenesis through induction of Nrf2-regulated pathways by the triterpenoid 1-[2-cyano-3-,12-dioxooleana-1,9(11)-dien-28-oyl]imidazole," *Cancer Res.*, 66:2488-2494, 2006.

Yore et al., "The synthetic triterpenoid 1-[2-cyano-3,12-dioxooleana-1,9(11)-dien-28-oyl]imidazole blocks nuclear factor-kappaB activation through direct inhibition of IkappaB kinase beta," *Mol. Cancer Ther.*, 5 (12): 3232-3239, 2006.

Yu and Kensler, "Nrf2 as a target for cancer chemoprevention," *Mutat. Res.*, 591 (1-2): 93-102, 2005.

Yue et al., "Depletion of intracellular glutathione contributes to JNK-mediated death receptor 5 upregulation and apoptosis induction by the novel synthetic triterpenoid methyl-2-cyano-3, 12-dioxooleana-1, 9-dien-28-oate (CDDO-Me).," *Cancer & Biology Therapy*, 5(5):492-497, 2006.

Zapata et al., "CDDO and CDDO-Im Reduce Tumor Burden in a Transgenic Mouse Model of CLL," *Blood*, 104:3477, 2004.

Zapata et al., "Triterpenoids show activity against leukemic cells in a transgenic mouse model of CLL," *Proc. Amer. Assoc. Cancer Res.*, 46: Abstract No. 5179, 2005.

Zhang et al., "Synthetic triterpenoid CDDO as effective therapy for HER2-expressing resistant breast cancer," *Proc. Amer. Assoc. Cancer Res.*, Abstract No. 3799, 2004.

Zhang et al., "The novel synthetic oleanane triterpenoid CDDO (2-cyano-3, 12-dioxoolean-1, 9-dien-28-oic acid) induces apoptosis in Mycosis fungoides/Sézary syndrome cells," *J. Invest. Dermatol.*, 123:380-387, 2004.

Zhou et al., "Carbon monoxide suppresses bleomycin-induced lung fibrosis," *Am. J. Pathol.*, 166 (1): 27-37, 2005.

Zhou et al., "Physical stability of amorphous pharmaceuticals: Importance of configurational thermodynamic quantities and molecular mobility," *J. Pharmaceutical Sciences*, 91 (8): 1863-1872, 2002.

Zou et al., "c-Jun NH2-terminal kinase-mediated up-regulation of death receptor 5 contributes to induction of apoptosis by the novel synthetic triterpenoid methyl-2-cyano-3,12-dioxooleana-1, 9-dien-28-oate in human lung cancer cells," *Cancer Res.*, 64:7570-7578, 2004.

European Search Report issued in EP 08795303, dated Jul. 9, 2010.

International Search Report and Written Opinion issued in PCT/US08/09703, dated Nov. 5, 2008.

Office Action issued in U.S. Appl. No. 12/191,176, dated Sep. 21, 2010.

Office Action issued in U.S. Appl. No. 12/191,176, dated Apr. 7, 2011.

Office Action issued in New Zealand Patent Application No. 586751, dated Mar. 25, 2011.

English Translation of Office Action issued in Japanese Patent Application No. 2010-542411. dated Jun. 9, 2011.

Pergola et al., "Bardoxolone methyl and kidney function in CKD with type 2 diabetes," *New England Journal of Medicine*, 365(4):327-36, 2011. (Supplementary Appendix included).

Agodoa et al., "Effect of ramipril vs amlodipine on renal outcomes in hypertensive nephrosclerosis," *JAMA*, 285:2719-2728, 2001.

Blann et al., "Circulating endothelial cells," *Thromb Haemost*, 93:228-235, 2005.

File History of U.S. Appl. No. 12/191,176, filed Aug. 13, 2008.

Guilherme et al., "Adipocyte dysfunctions linking obesity to insulin resistance and type 2 diabetes," *Nat. Rev. Mol. Cell Biol.*, 9 (5): 367-377, 2008.

Liby et al., "The synthetic triterpenoids CDDO-methyl ester and CDDO-ethyl amide prevent lung cancer induced by vinyl carbamate in A/J mice," *Cancer Res*, 67(6)2414-2419, 2007.

Lozano et al., "Losartan reduces microalbuminuria in hypertensive microalbuminuric type 2 diabetics," *Nephrol Dial Transplant*, 16(Suppl 1):85-89, 2001.

Ma et al., "Multiorgan autoimmune inflammation, enhanced lymphoproliferation, and impaired homeostasis of reactive oxygen species in mice lacking the antioxidant-activated transcription factor Nrf2," *Am J Pathol*, 168:1960-1974, 2006.

Mann et al., "Renal outcomes with telmisartan, ramipril, or both, in people at high vascular risk (the ONTARGET study): a multicentre, randomized, double-blind, controlled trial," *Lancet*, 372:547-553, 2008.

Nichols, "NF-kappaB and reperfusion injury," *Drug News Perspect.*, 17 (2): 99-104, 2004.

Niikura et al., "The effects of synthetic triterpenoids on superficial zone protein synthesis in articular chondrocytes," Abstract, *Orthopedic Research Society*, San Diego, 2007.

Niikura et al., "The effects of synthetic triterpenoids on szp synthesis in articular chondrocytes," Abstract P197, *Osteoarthritis and Cartilage*, 14(Suppl B):S112-S113, 2006.

Sengul et al., "Beneficial effect of lisinopril plus telmisartan in patients with type 2 diabetes, microalbuminuria and hypertension," *Diabetes Research and Clinical Practice*, 71:210-219, 2006.

Sjöholm and Nyström, "Inflammation and the etiology of type 2 diabetes," *Diabetes Metab. Res. Rev.*, 22: 4-10, 2006.

Suh et al., "Novel triterpenoids suppress inducible nitric oxide synthase (iNOS) and inducible cyclooxygenase (COX-2) in mouse macrophages," *Cancer Research*, 58:717-723, 1998.

Sun et al., "Structure-activity relationships of oleanane- and ursane-type triterpenoids," *Botanical Studies*, 47:339-368, 2006.

Vannini et al., "The synthetic oleanane triterpenoid, CDDO-methyl ester, is a potent antiangiogenic agent," *Molecular Cancer Therapeutics*, 6 (12 Part 1), 3139-3146, 2007.

Viberti et aL, "Microalbuminuria reduction with valsartan in patients with type 2 diabetes mellitus—A blood pressure-independent effect," *Circulation*, 106:672-678, 2002.

Vincenti et al., "The synthetic triterpenoid TP-222 inhibits RANKL induction of differentiation and MMP-9 gene expression in osteoclasts," Abstract 1385, *American College of Rheumatology Annual Scientific Meeting*, 2006.

Wardle, "Nuclear factor kappaB for the nephrologist," *Nephrol. Dial. Transplant.*, 16(9):1764-1768, 2001.

Yao et al., "Cisplatin nephrotoxicity: a review," *Am J Med Sci*, 334(2):115-124, 2007.

Yoh et al., "Nrf2-deficient female mice develop lupus-like autoimmune nephritis," *Kidney Int.*, 60(4):1343-1353, 2001.

Aschner et al., "Effect of the dipeptidyl peptidase-4 inhibitor sitagliptin as monotherapy on glycemic control in patients with type 2 diabetes," *Diabetes Care*, 29(12):2632-2637, 2006.

Goldstein et al., "Effect of initial combination therapy with sitagliptin, a dipeptidyl peptidase-4 inhibitor, and metformin on glycemic control in patients with type 2 diabetes," *Diabetes Care*, 30(8):1979-1987, 2007.

Goodman et aL, "Heme oxygenase-1 protects against radiocontrast-induced acute kidney injury by regulating anti-apoptotic proteins," *Kidney Int.*, 72:945-953, 2007.

Kobayashi and Yamamoto, "Molecular mechanisms activating the Nrf2-Keap 1 pathway of antioxidant gene regulation," *Antioxid. Redox. Signal.*, 7:385-394, 2005.

Maines and Gibbs, "30 some years of heme oxygenase: from a 'molecular wrecking ball' to a 'mesmerizing' trigger of cellular events," *Biochem. Biophys. Res. Commun.*, 338:568-577, 2005.

Nath, "Heme oxygenase-1: a provenance for cytoprotective pathways in the kidney and other tissues," *Kidney Int.*, 70, 432-443, 2006.

Stacul et al., "Strategies to reduce the risk of contrast-induced nephropathy," *Am J Cardiol*, 98(suppl):59K-77K, 2006.

Tumlin et al., "Pathophysiology of contrast-induced nephropathy," *Am. J. Cardiol.*, 98(Suppl):14K-20K, 2006.

Zingarelli et al., "Nuclear factor-κB as a therapeutic target in critical care medicine," *Crit Care Med.*, 31(Suppl):S105-S111, 2003.

"RTA 402, Therapeutic Properties I", slides/handouts presented by Reata Pharmaceuticals, Inc. at private partnering meetings at BioSquare 2006 conference, Mar. 8-10, 2006, Geneva, Switzerland.

"RTA 402, Therapeutic Properties II", slides/handouts presented by Reata Pharmaceuticals, Inc. at private partnering meetings at BIO 2006 conference, Apr. 9-12, 2006, Chicago, Illinois.

"RTA 402, Therapeutic Properties III", slides presented by Reata Pharmaceuticals, Inc. as a podium presentation at BIO 2006 conference, Apr. 9-12, 2006, Chicago, Illinois.

"RTA 402, Therapeutic Properties IV", slides/handouts presented by Reata Pharmaceuticals, Inc. at private partnering meetings at BioPartnering Europe 2006 conference, Oct. 8-10, 2006, London, England.

"RTA 402, Therapeutic Properties V", slides/handouts presented by Reata Pharmaceuticals, Inc. at private partnering meetings at BIO 2007 conference, May 6-9, 2007, Boston Massachusetts.

"RTA 402, Therapeutic Properties VI", slides/handouts presented by Reata Pharmaceuticals, Inc. at private partnering meetings at BIO 2007 conference, May 6-9, 2007, Boston, Massachusetts.

"RTA 402, Therapeutic Properties VII", slides presented by Reata Pharmaceuticals, Inc. as a podium presentation at BIO 2007 conference, May 6-9, 2007, Boston, Massachusetts.

"RTA 402, Therapeutic Properties VIII", slides/handouts presented by Reata Pharmaceuticals, Inc. at private partnering meetings at BIO Europe 2007 conference, Nov. 12-14, 2007, Hamburg, Germany.

"RTA 402, Therapeutic Properties IX", slides/handouts presented by Reata Pharmaceuticals, Inc. at a private partnering meeting at BIO Europe 2007 conference, Nov. 12-14, 2007, Hamburg, Germany.

ClinicalTrials.gov study record NCT 00352040, "CDDO in treating patients with metastatic or unresectable solid tumors or lymphoma conditions: lymphoma; small intestine cancer; unspecified adult solid tumor, protocol specific," update of Jul. 13, 2006.

ClinicalTrials.gov study record NCT 00352040, "CDDO in treating patients with metastatic or unresectable solid tumors or lymphoma conditions: lymphoma; small intestine cancer; unspecified adult solid tumor, protocol specific," update of Jul. 19, 2006.

ClinicalTrials.gov study record NCT 00352040, "CDDO in treating patients with metastatic or unresectable solid tumors or lymphoma conditions: lymphoma; small intestine cancer; unspecified adult solid tumor, protocol specific," update of Aug. 14, 2006.

ClinicalTrials.gov study record NCT 00352040, "CDDO in treating patients with metastatic or unresectable solid tumors or lymphoma conditions: lymphoma; small intestine cancer; unspecified adult solid tumor, protocol specific," update of Sep. 6, 2006.

ClinicalTrials.gov study record NCT 00352040, "CDDO in treating patients with metastatic or unresectable solid tumors or lymphoma conditions: lymphoma; small intestine cancer; unspecified adult solid tumor, protocol specific," update of Sep. 13, 2006.

ClinicalTrials.gov study record NCT 00352040, "CDDO in treating patients with metastatic or unresectable solid tumors or lymphoma conditions: lymphoma; small intestine cancer; unspecified adult solid tumor, protocol specific," update of Sep. 29, 2006.

ClinicalTrials.gov study record NCT 00352040, "CDDO in treating patients with metastatic or unresectable solid tumors or lymphoma conditions: lymphoma; small intestine cancer; unspecified adult solid tumor, protocol specific," update of Nov. 9, 2006.

ClinicalTrials.gov study record NCT 00352040, "CDDO in treating patients with metastatic or unresectable solid tumors or lymphoma conditions: lymphoma; small intestine cancer; unspecified adult solid tumor, protocol specific," update of Dec. 27, 2006.

ClinicalTrials.gov study record NCT 00352040, "CDDO in treating patients with metastatic or unresectable solid tumors or lymphoma conditions: lymphoma; small intestine cancer; unspecified adult solid tumor, protocol specific," update of Jan. 11, 2007.

ClinicalTrials.gov study record NCT 00352040, "CDDO in treating patients with metastatic or unresectable solid tumors or lymphoma conditions: lymphoma; small intestine cancer; unspecified adult solid tumor, protocol specific," update of Feb. 20, 2007.

ClinicalTrials.gov study record NCT 00352040, "CDDO in treating patients with metastatic or unresectable solid tumors or lymphoma conditions: lymphoma; small intestine cancer; unspecified adult solid tumor, protocol specific," update of Apr. 10, 2007.

ClinicalTrials.gov study record NCT 00352040, "CDDO in treating patients with metastatic or unresectable solid tumors or lymphoma conditions: lymphoma; small intestine cancer; unspecified adult solid tumor, protocol specific," update of Jun. 4, 2007.

ClinicalTrials.gov study record NCT 00352040, "CDDO in treating patients with metastatic or unresectable solid tumors or lymphoma conditions: lymphoma; small intestine cancer; unspecified adult solid tumor, protocol specific," update of Jul. 17, 2007.

ClinicalTrials.gov study record NCT 00352040, "CDDO in treating patients with metastatic or unresectable solid tumors or lymphoma conditions: lymphoma; small intestine cancer; unspecified adult solid tumor, protocol specific," update of Aug. 21, 2007.

ClinicalTrials.gov study record NCT 00352040, "CDDO in treating patients with metastatic or unresectable solid tumors or lymphoma conditions: lymphoma; small intestine cancer; unspecified adult solid tumor, protocol specific," update of Sep. 18, 2007.

ClinicalTrials.gov study record NCT 00352040, "CDDO in treating patients with metastatic or unresectable solid tumors or lymphoma conditions: lymphoma; small intestine cancer; unspecified adult solid tumor, protocol specific," update of Sep. 20, 2007.

ClinicalTrials.gov study record NCT 00352040, "CDDO in treating patients with metastatic or unresectable solid tumors or lymphoma conditions: lymphoma; small intestine cancer; unspecified adult solid tumor, protocol specific," update of Oct. 15, 2007.

ClinicalTrials.gov study record NCT 00352040, "CDDO in treating patients with metastatic or unresectable solid tumors or lymphoma conditions: lymphoma; small intestine cancer; unspecified adult solid tumor, protocol specific," update of Oct. 30, 2007.

ClinicalTrials.gov study record NCT 00352040, "CDDO in treating patients with metastatic or unresectable solid tumors or lymphoma conditions: lymphoma; small intestine cancer; unspecified adult solid tumor, protocol specific," update of Dec. 27, 2007.

ClinicalTrials.gov study record NCT 00352040, "CDDO in treating patients with metastatic or unresectable solid tumors or lymphoma conditions: lymphoma; small intestine cancer; unspecified adult solid tumor, protocol specific," update of May 26, 2008.

ClinicalTrials.gov study record NCT 00352040, "CDDO in treating patients with metastatic or unresectable solid tumors or lymphoma conditions: lymphoma; small intestine cancer; unspecified adult solid tumor, protocol specific," update of Jul. 23, 2008.

ClinicalTrials.gov study record NCT 00352040, "CDDO in treating patients with metastatic or unresectable solid tumors or lymphoma conditions: lymphoma; small intestine cancer; unspecified adult solid tumor, protocol specific," update of Jul. 31, 2008.

ClinicalTrials.gov study record NCT 00352040, "CDDO in treating patients with metastatic or unresectable solid tumors or lymphoma conditions: lymphoma; small intestine cancer; unspecified adult solid tumor, protocol specific," update of Oct. 20, 2008.

ClinicalTrials.gov study record NCT 00352040, "CDDO in treating patients with metastatic or unresectable solid tumors or lymphoma conditions: lymphoma; small intestine cancer; unspecified adult solid tumor, protocol specific," update of Nov. 26, 2008.

ClinicalTrials.gov study record NCT 00352040, "CDDO in treating patients with metastatic or unresectable solid tumors or lymphoma conditions: lymphoma; small intestine cancer; unspecified adult solid tumor, protocol specific," update of Dec. 11, 2008.

ClinicalTrials.gov study record NCT 00508807, "RTA 402 in advanced solid tumors or lymphoid malignancies conditions: lymphoid malignancies; solid tumors," update of Jul. 27, 2007.

ClinicalTrials.gov study record NCT 00508807, "RTA 402 in advanced solid tumors or lymphoid malignancies conditions: lymphoid malignancies; solid tumors," update of Jan. 22, 2008.

ClinicalTrials.gov study record NCT 00508807, "RTA 402 in advanced solid tumors or lymphoid malignancies conditions: lymphoid malignancies; solid tumors," update of Aug. 27, 2008.

ClinicalTrials.gov study record NCT 00508807, "RTA 402 in advanced solid tumors or lymphoid malignancies conditions: lymphoid malignancies; solid tumors," update of Sep. 7, 2008.

ClinicalTrials.gov study record NCT 00529113, "Study with gemcitabine and RTA 402 for patients with unresectable pancreatic cancer," update of Sep. 13, 2007.

ClinicalTrials.gov study record NCT 00529113, "Study with gemcitabine and RTA 402 for patients with unresectable pancreatic cancer," update of Dec. 18, 2007.

ClinicalTrials.gov study record NCT 00529113, "Study with gemcitabine and RTA 402 for patients with unresectable pancreatic cancer," update of Mar. 10, 2008.

ClinicalTrials.gov study record NCT 00529113, "Study with gemcitabine and RTA 402 for patients with unresectable pancreatic cancer," update of Jun. 4, 2008.

ClinicalTrials.gov study record NCT 00529113, "Study with gemcitabine and RTA 402 for patients with unresectable pancreatic cancer," update of Jun. 12, 2008.

ClinicalTrials.gov study record NCT 00529113, "Study with gemcitabine and RTA 402 for patients with unresectable pancreatic cancer," update of Oct. 10, 2008.

ClinicalTrials.gov study record NCT 00529438, "RTA 402 in patients with advanced solid tumors or lymphoid malignancies conditions: advanced solid tumors; lymphoid malignancies," update of Sep. 13, 2007.

ClinicalTrials.gov study record NCT 00529438, "RTA 402 in patients with advanced solid tumors or lymphoid malignancies conditions: advanced solid tumors; lymphoid malignancies," update of Apr. 21, 2008.

ClinicalTrials.gov study record NCT 00529438, "RTA 402 in patients with advanced solid tumors or lymphoid malignancies conditions: advanced solid tumors; lymphoid malignancies," update of Dec. 21, 2008.

ClinicalTrials.gov study record NCT 00535314, "Study of two dose levels of RTA 402 in patients with advanced malignant melanoma condition: malignant melanoma," update of Sep. 25, 2007.

ClinicalTrials.gov study record NCT 00535314, "Study of two dose levels of RTA 402 in patients with advanced malignant melanoma condition: malignant melanoma," update of Dec. 10, 2007.

ClinicalTrials.gov study record NCT 00550849, "Study to assess the safety, tolerability, and pharmacodynamics of RTA 402 in patients with hepatic dysfunction condition: liver disease," update of Oct. 29, 2007.

ClinicalTrials.gov study record NCT 00550849, "Study to assess the safety, tolerability, and pharmacodynamics of RTA 402 in patients with hepatic dysfunction condition: liver disease," update of Nov. 6, 2007.

ClinicalTrials.gov study record NCT 00664027, "Phase IIa trial to determine the effects of bardoxolone methyl on renal function in patients with diabetic nephropathy condition: diabetic nephropathy," update of Apr. 21, 2008.

ClinicalTrials.gov study record NCT 00664027, "Phase IIa trial to determine the effects of bardoxolone methyl on renal function in patients with diabetic nephropathy condition: diabetic nephropathy," update of Aug. 17, 2008.

ClinicalTrials.gov study record NCT 00664027, "Phase IIa trial to determine the effects of bardoxolone methyl on renal function in patients with diabetic nephropathy condition: diabetic nephropathy," update of Oct. 7, 2008.

ClinicalTrials.gov study record NCT 00664027, "Phase IIa trial to determine the effects of bardoxolone methyl on renal function in patients with diabetic nephropathy condition: diabetic nephropathy," update of Dec. 21, 2008.

ClinicalTrials.gov study record NCT 00811889, "Trial to determine the effects of bardoxolone methyl on eGFR in patients with type 2 diabetes and chronic kidney disease conditions: chronic kidney disease; type 2 diabetes; diabetic nephropathy," update of Dec. 18, 2008.

Office Communication and currently pending claims for corresponding Singapore Patent Application No. 201004886-6, dated Sep. 15, 2011.

Ito et al., "Involvement of caspase-8 in the induction of osteosarcoma cell apoptosis by the novel triterpenoid CDDO," *47th Annual Meeting, Orthopaedic Research Society*, Feb. 25-28, 2001, San Francisco, California, p. 0863, Poster Session, 2001.

Ito et al., "The novel triterpenoid 2-cyano-3, 12-dioxoolean-1,9-dien-28-oic acid induces apoptosis of human myeloid leukemia cells by a caspase-8-dependent mechanism," *Cell Growth & Differentiation*, 11(5):261-267, 2000.

Ito et al., "The novel triterpenoid CDDO induces apoptosis and differentiation of human osteosarcoma cells by a caspase-8 dependent mechanism," *Mol. Pharmacol.*, 59:1094-1099, 2001.

Johansen et al., "Pharmacology and preclinical pharmacokinetics of the triterpenoid CDDO methyl ester," *Proc. Amer. Assoc. Cancer Res.*, 44:1728, 2003.

Johnson et al., "A plan for distinguishing between some five- and six-membered ring ketones," *J. Am Chem. Soc.*, 67:1745-1754, 1945.

Johnson et al., "Relationships between drug activity in NCI preclinical in vitro and in vivo models and early clinical trials," *Br. J. Cancer*, 84:1424-1431, 2001.

Joyce et al., "Integration of Rac-dependent regulation of cyclin D1 transcription through a nuclear factor-kappaB-dependent pathway," *J. Biol. Chem.*, 274 (236): 25245-25249, 1999.

Kahne and Collum, "Kinetic cyanations of ketone enolates," *Tetrahedron Lett.*, 22:5011-5014, 1981.

Kaltschmidt et al., "Transcription factor NF-kappaB is activated in primary neurons by amyloid beta peptides and in neurons surrounding early plaques from patients with Alzheimer disease," *Proc. Natl. Acad. Sci. USA*, 94:2642-2647, 1997.

Karin, "Nuclear factor-kappaB in cancer development and progression," *Nature*, 441:431-436, 2006.

Kasinski et al., "Inhibition of IkappaB kinase-nuclear factor-kappaB signaling pathway by 3,5- bis(2-flurobenzylidene)piperidin-4-one (EF24), a novel monoketone analog of curcumin," *Mol. Pharmacology*, 74 (3): 654-661, 2008.

Kawamori et al., "Chemopreventive activity of celecoxib, as specific cyclooxygenase-2 inhibitor, against colon carcinogenesis," *Cancer Res.*, 58(3):409-412, 1998.

SYNTHETIC TRITERPENOIDS AND METHODS OF USE IN THE TREATMENT OF DISEASE

The present application claims the benefit of priority to U.S. Provisional Application Nos. 61/020,624, filed Jan. 11, 2008, and 61/109,114, filed Oct. 28, 2008, the entire contents of each of which are incorporated by reference herein.

BACKGROUND OF THE INVENTION

I. Field of the Invention

The present invention relates generally to the fields of biology and medicine. More particularly, it concerns compositions and methods for treating and/or preventing renal/kidney disease (RKD), insulin resistance, diabetes, endothelial dysfunction, fatty liver disease, and cardiovascular disease (CVD).

II. Description of Related Art

Renal failure, resulting in inadequate clearance of metabolic waste products from the blood and abnormal concentrations of electrolytes in the blood, is a significant medical problem throughout the world, especially in developed countries. Diabetes and hypertension are among the most important causes of chronic renal failure, also known as chronic kidney disease (CKD), but it is also associated with other conditions such as lupus or systemic cardiovascular disease. Dysfunction of the vascular endothelium commonly occurs in such conditions and is believed to be a major contributing factor in the development of chronic kidney disease. Acute renal failure may arise from exposure to certain drugs (e.g., acetaminophen) or toxic chemicals or from ischemia-reperfusion injury associated with shock or surgical procedures such as transplantation, and may ultimately result in CKD. In many patients, CKD advances to end-stage renal disease (ESRD) in which the patient requires kidney transplantation or regular dialysis to continue living. Both of these procedures are highly invasive and associated with significant side effects and quality of life issues. Although there are effective treatments for some complications of renal failure, such as hyperparathyroidism and hyperphosphatemia, no available treatment has been shown to halt or reverse the underlying progression of renal failure. Thus, agents that can improve compromised renal function would represent a significant advance in the treatment of renal failure.

Triterpenoids, biosynthesized in plants by the cyclization of squalene, are used for medicinal purposes in many Asian countries; and some, like ursolic and oleanolic acids, are known to be anti-inflammatory and anti-carcinogenic (Huang et al., 1994; Nishino et al., 1988). However, the biological activity of these naturally-occurring molecules is relatively weak, and therefore the synthesis of new analogs to enhance their potency was undertaken (Honda et al., 1997; Honda et al., 1998). An ongoing effort for the improvement of anti-inflammatory and antiproliferative activity of oleanolic and ursolic acid analogs led to the discovery of 2-cyano-3,12-dioxooleane-1,9(11)-dien-28-oic acid (CDDO) and related compounds (Honda et al., 1997, 1998, 1999, 2000a, 2000b, 2002; Suh et al., 1998; 1999; 2003; Place et al., 2003; Liby et al., 2005). Several potent derivatives of oleanolic acid were identified, including methyl-2-cyano-3,12-dioxooleana-1,9-dien-28-oic acid (CDDO-Me; RTA 402). RTA 402 suppresses the induction of several important inflammatory mediators, such as iNOS, COX-2, TNFα, and IFNγ, in activated macrophages. RTA 402 has also been reported to activate the Keap1/Nrf2/ARE signaling pathway resulting in the production of several anti-inflammatory and antioxidant proteins, such as heme oxygenase-1 (HO-1). These properties have made RTA 402 a candidate for the treatment of neoplastic and proliferative diseases, such as cancer. The ability of this compound and related molecules to treat and/or prevent kidney disease and cardiovascular disease remains untested.

SUMMARY OF THE INVENTION

The present invention provides new methods for treating and/or preventing renal/kidney disease (RKD), insulin resistance, diabetes, endothelial dysfunction, fatty liver disease, cardiovascular disease (CVD), and related disorders. Compounds covered by the generic or specific formulas below or specifically named are referred to as "compounds of the invention," "compounds of the present invention," or "synthetic triterpenoids" in the present application.

In one aspect of the present prevention, methods are provided for treating or preventing renal/kidney disease (RKD), insulin resistance, diabetes, endothelial dysfunction, fatty liver disease, or cardiovascular disease (CVD) in a subject comprising, administering to said subject a pharmaceutically effective amount of a compound having the structure:

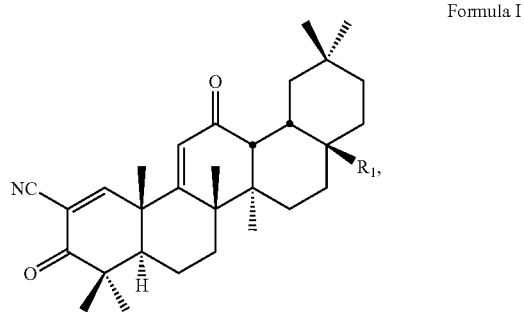

Formula I wherein $R_1$ is: —CN, or $C_1$-$C_{15}$-acyl or $C_1$-$C_{15}$-alkyl, wherein either of these groups is heteroatom-substituted or heteroatom-unsubstituted; or a pharmaceutically acceptable salt, hydrate or solvate thereof.

In some embodiments, methods are provided for treating RKD. In some variations, the RKD is diabetic nephropathy (DN). In other variations, the RKD results from a toxic insult, for example, wherein the toxic insult results from an imaging agent or a drug. For example, the drug may be a chemotherapeutic agent. In a further variation, the RKD results from ischemia/reperfusion injury. In yet a further variation, the RKD results from diabetes or hypertension. In still further variations, the RKD results from an autoimmune disease. In other variations, the RKD is chronic RKD. In still other variations, the RKD is acute RKD.

In some embodiments, the subject has undergone or is undergoing dialysis. In some embodiments, the subject has undergone or is a candidate to undergo kidney transplant. In some embodiments, the subject has RKD and insulin resistance. In some variations on the above embodiments, the subject has RKD, insulin resistance and endothelial dysfunction. In some embodiments, the subject has RKD and diabetes. In some embodiments, the subject has insulin resistance.

In some embodiments, the subject has diabetes. The pharmaceutically effective amount of the compound may also effectively treat one or more complications associated with diabetes. For example, the complications can be selected from the group consisting of obesity, hypertension, atherosclerosis, coronary heart disease, stroke, peripheral vascular disease, hypertension, nephropathy, neuropathy, myonecrosis, diabetic foot ulcers and other diabetic ulcers, retinopathy and metabolic syndrome (syndrome X). Also, for example, the complication can be metabolic syndrome (syndrome X). In some variations, the diabetes results from insulin resistance.

In some embodiments, the subject has RKD and endothelial dysfunction. In other embodiments, the subject has RKD and cardiovascular disease. In some embodiments, the subject has CVD. In some variations, the CVD results from endothelial dysfunction.

In some embodiments, the subject has endothelial dysfunction and/or insulin resistance. In some embodiments, the subject has fatty liver disease. In some variations, the fatty liver disease is non-alcoholic fatty liver disease. In other variations, the fatty liver disease is alcoholic fatty liver disease. In some variations, the subject has fatty liver disease and one or more of the following disorders: renal/kidney disease (RKD), insulin resistance, diabetes, endothelial dysfunction, and cardiovascular disease (CVD).

In some embodiments, the methods further comprise identifying a subject in need of treatment of any of the diseases, dysfunctions, resistances or disorders listed herein. In some embodiments, the subject has a family or patient history of any of the diseases, dysfunctions, resistances or disorders listed herein. In some embodiments, the subject exhibits symptoms of any of the diseases, dysfunctions, resistances or disorders listed herein.

In another aspect of the invention, a method is provided for improving glomerular filtration rate or creatinine clearance in a subject comprising, administering to said subject a pharmaceutically effective amount of a compound having the structure of Formula I, or a pharmaceutically acceptable salt, hydrate or solvate thereof.

In some embodiments, the compound is administered locally. In some embodiments, the compound is administered systemically. In some embodiments, the compound is administered orally, intraadiposally, intraarterially, intraarticularly, intracranially, intradermally, intralesionally, intramuscularly, intranasally, intraocularally, intrapericardially, intraperitoneally, intrapleurally, intraprostatically, intrarectally, intrathecally, intratracheally, intratumorally, intraumbilically, intravaginally, intravenously, intravesicularlly, intravitreally, liposomally, locally, mucosally, orally, parenterally, rectally, subconjunctivally, subcutaneously, sublingually, topically, transbuccally, transdermally, vaginally, in cremes, in lipid compositions, via a catheter, via a lavage, via continuous infusion, via infusion, via inhalation, via injection, via local delivery, via localized perfusion, bathing target cells directly, or any combination thereof. For example, in some variations, the compound is administered intravenously, intra-arterially or orally. For example, in some variations, the compound is administered orally.

In some embodiments, the compound is formulated as a hard or soft capsule, a tablet, a syrup, a suspension, a solid dispersion, a wafer, or an elixir. In some variations, the soft capsule is a gelatin capsule. In variations, the compound is formulated as a solid dispersion. In some variations the hard capsule, soft capsule, tablet or wafer further comprises a protective coating. In some variations, the formulated compound comprises an agent that delays absorption. In some variations, the formulated compound further comprises an agent that enhances solubility or dispersibility. In some variations, the compound is dispersed in a liposome, an oil in water emulsion or a water in oil emulsion.

In some embodiments, the pharmaceutically effective amount is a daily dose from about 0.1 mg to about 500 mg of the compound. In some variations, the daily dose is from about 1 mg to about 300 mg of the compound. In some variations, the daily dose is from about 10 mg to about 200 mg of the compound. In some variations, the daily dose is about 25 mg of the compound. In other variations, the daily dose is about 75 mg of the compound. In still other variations, the daily dose is about 150 mg of the compound. In further variations, the daily dose is from about 0.1 mg to about 30 mg of the compound. In some variations, the daily dose is from about 0.5 mg to about 20 mg of the compound. In some variations, the daily dose is from about 1 mg to about 15 mg of the compound. In some variations, the daily dose is from about 1 mg to about 10 mg of the compound. In some variations, the daily dose is from about 1 mg to about 5 mg of the compound.

In some embodiments, the pharmaceutically effective amount is a daily dose is 0.01-25 mg of compound per kg of body weight. In some variations, the daily dose is 0.05-20 mg of compound per kg of body weight. In some variations, the daily dose is 0.1-10 mg of compound per kg of body weight. In some variations, the daily dose is 0.1-5 mg of compound per kg of body weight. In some variations, the daily dose is 0.1-2.5 mg of compound per kg of body weight.

In some embodiments, the pharmaceutically effective amount is administered in a single dose per day. In some embodiments, the pharmaceutically effective amount is administered in two or more doses per day.

In some embodiments, the treatment method further comprises a second therapy. In some variations, the second therapy comprises administering to said subject a pharmaceutically effective amount of a second drug. In some embodiments, the second drug is a cholesterol lowering drug, an anti-hyperlipidemic, a calcium channel blocker, an anti-hypertensive, or an HMG-CoA reductase inhibitor. Non-limiting examples of second drugs are amlodipine, aspirin, ezetimibe, felodipine, lacidipine, lercanidipine, nicardipine, nifedipine, nimodipine, nisoldipine and nitrendipine. Further non-limiting examples of second drugs are atenolol, bucindolol, carvedilol, clonidine, doxazosin, indoramin, labetalol, methyldopa, metoprolol, nadolol, oxprenolol, phenoxybenzamine, phentolamine, pindolol, prazosin, propranolol, terazosin, timolol and tolazoline. In some variations, the second drug is a statin. Non-limiting examples of statins are atorvastatin, cerivastatin, fluvastatin, lovastatin, mevastatin, pitavastatin, pravastatin, rosuvastatin and simvastatin. In some variations, the second drug is a dipeptidyl peptidase-4 (DPP-4) inhibitor. Non-limiting examples of DPP-4 inhibitors are sitagliptin, vildagliptin, SYR-322, BMS 477118 and GSK 823093. In some variations, the second drug is a biguanide. For example, the biguanide can be metformin. In some variations, the second drug is a thiazolidinedione (TZD). Non-limiting examples of TZDs are pioglitazone, rosiglitazone and troglitazone. In some variations, the second drug is a sulfonylurea derivative. Non-limiting examples of sulfonyl urea derivatives are tolbutamide, acetohexamide, tolazamide, chlorpropamide, glipizide, glyburide, glimepiride and gliclazide. In some variations, the second drug is a meglitinide. Non-limiting examples of meglitinides include repaglinide, mitiglinide and nateglinide. In some variations, the second drug is insulin. In some variations, the second drug is an alpha-glucosidase inhibitor. Non-limiting examples of alpha-glucosidase inhibitors are acarbose, miglitol and voglibose. In some variations, the second drug is a glucagon-like peptide-1 analog. Non-limiting examples of glucagon-like peptide-1 analogs are exenatide and liraglutide. In some variations, the second drug is a gastric inhibitory peptide analog. In some variations, the second drug is a GPR40 agonist. In some variations, the second drug is a GPR119 agonist. In some variations the second drug is a GPR30 agonist. In some variations, the second drug is a glucokinase activator. In some variations, the second drug is a glucagon receptor antagonist. In some variations, the second drug is an amylin analog. A non-limiting example of an amylin analog is pramlintide. In some variations, the second drug is an IL-1β receptor antagonist. A non-limiting examples of a IL-1β receptor antagonist is anakinra. In some variations, the second drug is an endocannabinoid receptor antagonist or inverse agonist. A non-limiting example of a endocannabinoid receptor antagonist or inverse agonist is rimonabant. In some variations, the second drug is Orlistat. In some variations, the second drug is Sibutramine. In some variations, the second drug is a growth factor. Non-limiting examples of growth factors are TGF-β1, TGF-β2, TGF-β1.2, VEGF, insulin-like growth factor I or II, BMP2, BMP4, BMP7, a GLP-1 analog, a GIP analog, a DPP-IV inhibitor, a GPR119 agonist, a GPR40 agonist, gastrin, EGF, betacellulin, KGF, NGF, insulin, growth hormone, HGF, an FGF, an FGF homologue, PDGF, Leptin, prolactin, placental lactogen, PTHrP, activin, inhibin, and INGAP. Further non-limiting examples of growth factors are parathyroid hormone, calcitonin, interleukin-6, and interleukin-11.

In some embodiments, the subject is a primate. In some variations, the primate is a human. In other variations, the subject is a cow, horse, dog, cat, pig, mouse, rat or guinea pig.

In some embodiments, the compound is defined as:

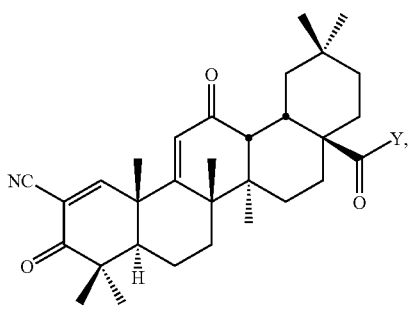

Formula II wherein Y is: —H, hydroxy, amino, halo, or $C_1$-$C_{14}$-alkoxy, $C_2$-$C_{14}$-alkenyloxy, $C_2$-$C_{14}$-alkynyloxy, $C_1$-$C_{14}$-aryloxy, $C_2$-$C_{14}$-aralkoxy, $C_1$-$C_{14}$-alkylamino, $C_2$-$C_{14}$-alkenylamino, $C_2$-$C_{14}$-alkynylamino, $C_1$-$C_{14}$-arylamino, $C_3$-$C_{10}$-aryl, or $C_2$-$C_{14}$-aralkylamino, wherein any of these groups is heteroatom-substituted or heteroatom-unsubstituted; or a pharmaceutically acceptable salt, hydrate or solvate thereof.

In some embodiments, Y is a heteroatom-unsubstituted $C_1$-$C_4$-alkylamino, such that the compound of the invention is, for example:

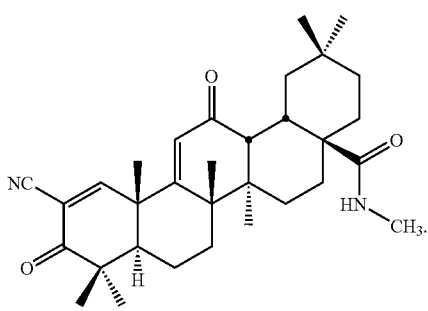

In some embodiments, Y is a heteroatom-substituted or heteroatom-unsubstituted $C_2$-$C_4$-alkylamino, such that the compound of the invention is, for example:

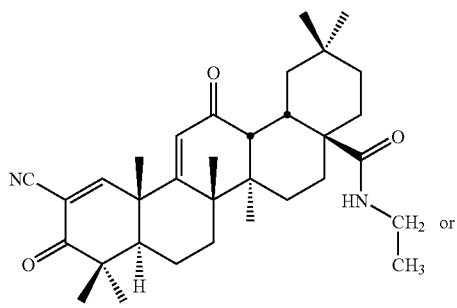

or

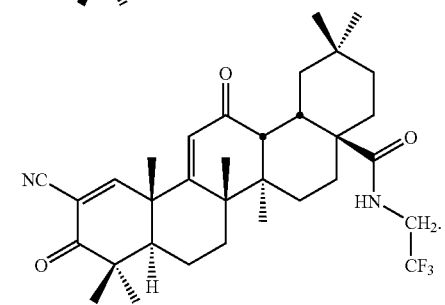

In some embodiments, Y is a heteroatom-substituted or heteroatom-unsubstituted $C_1$-$C_4$-alkoxy, such as a heteroatom-unsubstituted $C_1$-$C_2$-alkoxy. For example, one non-limiting example of such a compound is:

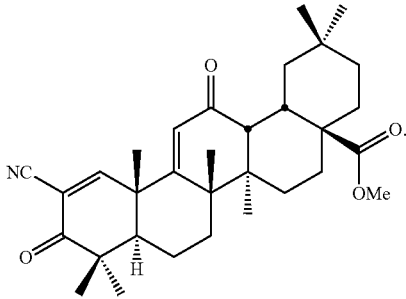

(CDDO-Me, RTA 402)

In some embodiments, at least a portion of the CDDO-Me is present as a polymorphic form, wherein the polymorphic form is a crystalline form having an X-ray diffraction pattern (CuKα) comprising significant diffraction peaks at about 8.8, 12.9, 13.4, 14.2 and 17.4° 2θ. In non-limiting examples, the X-ray diffraction pattern (CuKα) is substantially as shown in FIG. 12A or FIG. 12B. In other variations, at least a portion of the CDDO-Me is present as a polymorphic form, wherein the polymorphic form is an amorphous form having an X-ray diffraction pattern (CuKα) with a halo peak at approximately 13.5° 2θ, substantially as shown in FIG. 12C, and a $T_g$. In some variations, the compound is an amorphous form. In some variations, the compound is a glassy solid form of CDDO-Me, having an X-ray powder diffraction pattern with a halo peak at about 13.5° 2θ, as shown in FIG. 12C, and a $T_g$. In some variations, the $T_g$ value falls within a range of about 120° C. to about 135° C. In some variations, the $T_g$ value is from about 125° C. to about 130° C.

In some embodiments, Y is hydroxy, such that the compound of the invention is, for example:

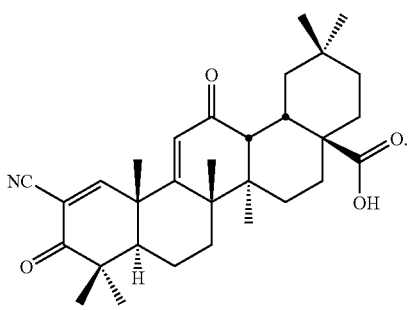

In some embodiments, the compound is:

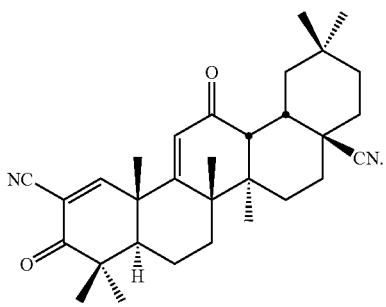

In some embodiments, the compound is defined as:

Formula III

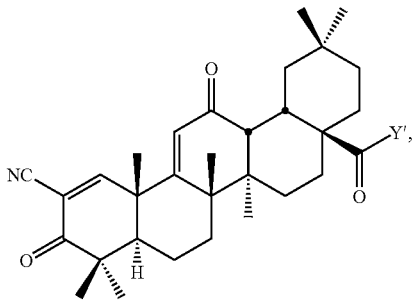

wherein Y' is a heteroatom-substituted or heteroatom-unsubstituted $C_1$-$C_{14}$-aryl; or a pharmaceutically acceptable salt, hydrate or solvate thereof.

In some embodiments, the compound is:

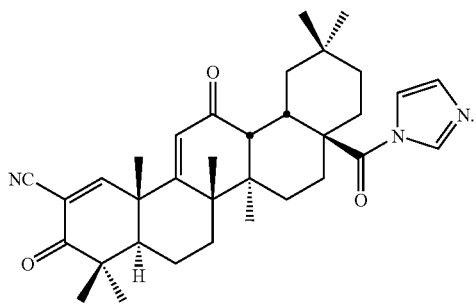

In some variations of the above methods, the compound is substantially free from optical isomers thereof. In some variations of the above methods, the compound is in the form of a pharmaceutically acceptable salt. In other variations of the above methods, the compound is not a salt.

In some embodiments, the compound is formulated as a pharmaceutical composition comprising (i) a therapeutically effective amount of the compound and (ii) an excipient is selected from the group consisting of (A) a carbohydrate, carbohydrate derivative, or carbohydrate polymer, (B) a synthetic organic polymer, (C) an organic acid salt, (D) a protein, polypeptide, or peptide, and (E) a high molecular weight polysaccharide. In some variations, the excipient is a synthetic organic polymer. In some variations, the excipient is selected from the group consisting of a hydroxypropyl methyl cellulose, a poly[1-(2-oxo-1-pyrrolidinyl)ethylene or copolymer thereof, and a methacrylic acid-methylmethacrylate copolymer. In some variations, the excipient is hydroxypropyl methyl cellulose phthalate ester. In some variations, the excipient is PVP/VA. In some variations, the excipient is a methacrylic acid-ethyl acrylate:copolymer (1:1). In some variations, the excipient is copovidone.

Any embodiment discussed herein with respect to one aspect of the invention applies to other aspects of the invention as well, unless specifically noted.

Other objects, features and advantages of the present invention will become apparent from the following detailed description and any accompanying drawings. It should be understood, however, that the detailed description and any specific examples or drawings provided, while indicating specific embodiments of the invention, are given by way of illustration only, since various changes and modifications within the spirit and scope of the invention will become apparent to those skilled in the art from this detailed description.

BRIEF DESCRIPTION OF THE DRAWINGS

The following drawings form part of the present specification and are included to further demonstrate certain aspects of the present invention. The invention may be better understood by reference to one or more of these drawings in combination with the detailed description of specific embodiments presented herein.

(FIG. 1a) On Day 1, blood was collected from animals that were subjected to clamping and "sham" control animals that underwent surgery without clamping of the renal artery. Blood urea nitrogen (BUN) levels were measured as a surrogate for renal damage. (FIGS. 1b-d) Sections of kidneys from RTA 402-treated or vehicle-treated mice were scored for histological damage (FIGS. 1b & 1d) and inflammation (FIG. 1c). (FIG. 1d) Black arrows (vehicle group) show two of many severely damaged tubules in the outer medulla. Red arrows (RTA 402 group) show two of many undamaged tubules in the outer medulla.

(FIG. 2c) Less damage to the proximal tubules is observed in RTA 402-treated animals compared to vehicle-treated animals.

(FIG. 3a) Cynomolgus monkeys were administered RTA 402 orally at the indicated doses once daily for 28 days. The percent reduction of serum creatinine on Day 28 in RTA 402-treated monkeys relative to vehicle-treated control monkeys is shown. (FIG. 3b) RTA 402 was administered orally to beagle dogs at the indicated doses daily for three months. Control animals received vehicle (sesame oil). The percent change in serum creatinine at the three-month time point relative to baseline is shown. (FIG. 3c) Sprague-Dawley rats were administered RTA 402 orally at the indicated doses once daily for a period of one month. The percent reduction of serum creatinine at study completion in RTA 402-treated rats relative to vehicle-treated control rats is shown. (FIG. 3d) Sprague-Dawley rats were administered the amorphous form of RTA 402 orally at the indicated doses once daily for a period of three months. The percent reduction of serum creatinine at study completion in RTA 402-treated rats relative to vehicle-treated control rats is shown. Note: in FIGS. 3A, 3C and 3D, "% reduction" on the vertical axis indicates percent change. For example, a reading of −15 on this axis indicates a 15% reduction in serum creatinine.

FIG. 4A: Serum creatinine was measured in RTA 402-treated patients enrolled in a Phase I clinical trial for the treatment of cancer. The patients were administered RTA 402 (p.o.) once daily for 21 days at doses ranging from 5 to 1,300 mg/day. The percent reduction of serum creatinine relative to baseline levels is shown for the indicated study days. Significant decreases in serum creatinine levels were observed on Days 15 and 21. FIG. 4B: The estimated glomerular filtration rate (eGFR) was calculated for the patients in FIG. 4A. Significant improvements in the eGFR were observed in both groups. All patients: n=24; patients with baseline≧1.5: n=5. For FIGS. 4A and 4B, * indicates p≧0.04; † indicates p=0.01, and ‡ indicates p≦0.01. Note: in FIG. 4A, "% Reduction from Baseline" on the vertical axis indicates percent change. For example, a reading of −15 on this axis indicates a 15% reduction in serum creatinine.

FIG. 12A shows unmicronized Form A; FIG. 12B shows micronized Form A; FIG. 12C shows Form B.

DESCRIPTION OF ILLUSTRATIVE EMBODIMENTS

I. The Present Invention

Figure 1:
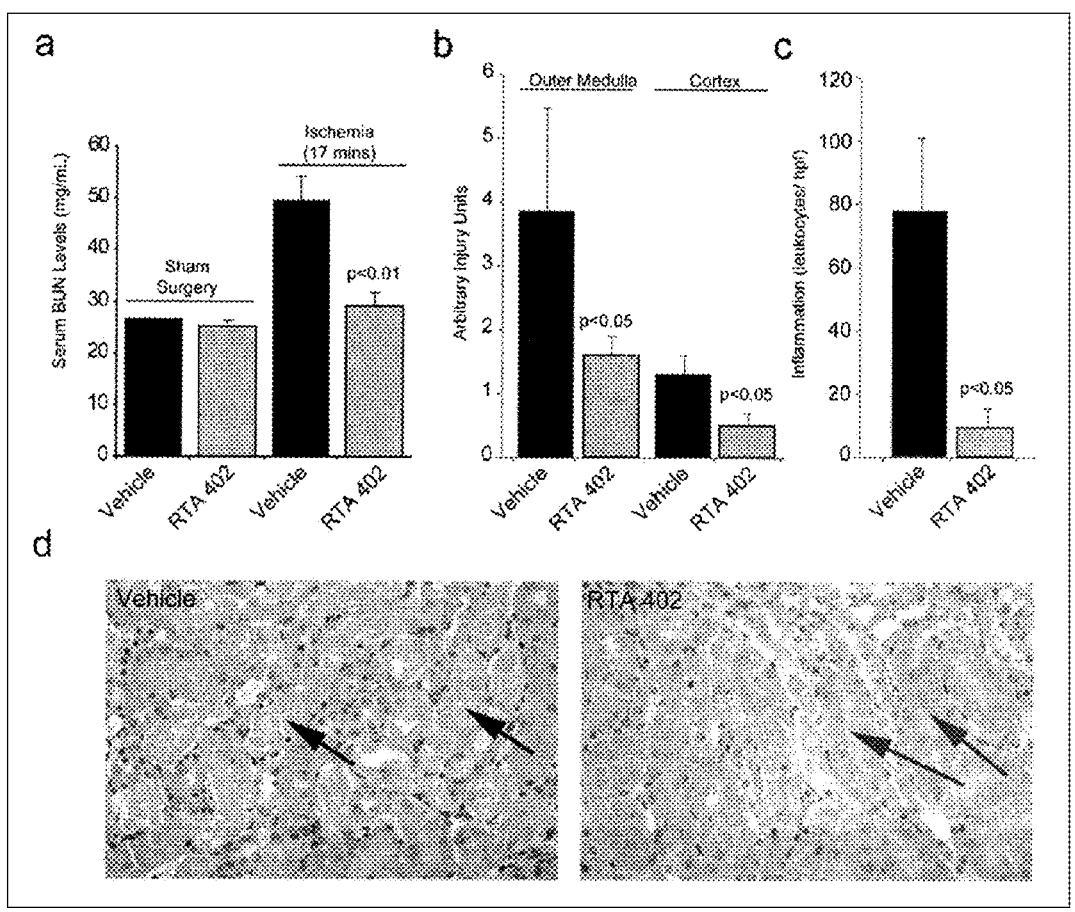
FIGS. 1a-d—RTA 402 reduces renal damage following ischemia-reperfusion. Mice were administered RTA 402 at 2 mg/kg or simply the vehicle (sesame oil) daily by oral gavage beginning on Day 2. On Day 0, a clamp was placed on the left renal artery for 17 minutes and then removed to induce ischemia-reperfusion.

The present invention concerns new methods for the treatment and prevention of renal disease and related disorders, including diabetes and cardiovascular disease, involving the use of triterpenoids.

II. Definitions

As used herein, the term "amino" means —$NH_2$; the term "nitro" means —$NO_2$; the term "halo" designates —F, —Cl, —Br or —I; the term "mercapto" means —SH; the term "cyano" means —CN; the term "silyl" means —$SiH_3$, and the term "hydroxy" means —OH.

The term "heteroatom-substituted," when used to modify a class of organic radicals (e.g., alkyl, aryl, acyl, etc.), means that one, or more than one, hydrogen atom of that radical has been replaced by a heteroatom, or a heteroatom containing group. Examples of heteroatoms and heteroatom containing groups include: hydroxy, cyano, alkoxy, =O, =S, —$NO_2$, —N(CH$_3$)$_2$, amino, or —SH. Specific heteroatom-substituted organic radicals are defined more fully below.

The term "heteroatom-unsubstituted," when used to modify a class of organic radicals (e.g., alkyl, aryl, acyl, etc.) means that none of the hydrogen atoms of that radical have been replaced with a heteroatom or a heteroatom containing group. Substitution of a hydrogen atom with a carbon atom, or a group consisting of only carbon and hydrogen atoms, is not sufficient to make a group heteroatom-substituted. For example, the group —C$_6$H$_4$C≡CH is an example of a heteroatom-unsubstituted aryl group, while —C$_6$H$_4$F is an example of a heteroatom-substituted aryl group. Specific heteroatom-unsubstituted organic radicals are defined more fully below.

The term "alkyl" includes straight-chain alkyl groups, branched-chain alkyl groups, cycloalkyl (alicyclic) groups, alkyl heteroatom-substituted cycloalkyl groups, and cycloalkyl heteroatom-substituted alkyl groups. The term "heteroatom-unsubstituted C$_n$-alkyl" refers to a radical having a linear or branched, cyclic or acyclic structure, further having no carbon-carbon double or triple bonds, further having a total of n carbon atoms, all of which are nonaromatic, 3 or more hydrogen atoms, and no heteroatoms. For example, a heteroatom-unsubstituted C$_1$-C$_{10}$-alkyl has 1 to 10 carbon atoms. The groups, —CH$_3$, —CH$_2$CH$_3$, —CH$_2$CH$_2$CH$_3$, —CH(CH$_3$)$_2$, —CH(CH$_2$)$_2$ (cyclopropyl), —CH$_2$CH$_2$CH$_2$CH$_3$, —CH(CH$_3$)CH$_2$CH$_3$, —CH$_2$CH(CH$_3$)$_2$, —C(CH$_3$)$_3$, —CH$_2$C(CH$_3$)$_3$, cyclobutyl, cyclopentyl, and cyclohexyl, are all examples of heteroatom-unsubstituted alkyl groups. The term "heteroatom-substituted C$_n$-alkyl" refers to a radical having a single saturated carbon atom as the point of attachment, no carbon-carbon double or triple bonds, further having a linear or branched, cyclic or acyclic structure, further having a total of n carbon atoms, all of which are nonaromatic, 0, 1, or more than one hydrogen atom, at least one heteroatom, wherein each heteroatom is independently selected from the group consisting of N, O, F, Cl, Br, I, Si, P, and S. For example, a heteroatom-substituted C$_1$-C$_{10}$-alkyl has 1 to 10 carbon atoms. The following groups are all examples of heteroatom-substituted alkyl groups: trifluoromethyl, —CH$_2$F, —CH$_2$Cl, —CH$_2$Br, —CH$_2$OH, —CH$_2$OCH$_3$, —CH$_2$OCH$_2$CH$_3$, —CH$_2$OCH$_2$CH$_2$CH$_3$, —CH$_2$OCH(CH$_3$)$_2$, —CH$_2$OCH(CH$_2$)$_2$, —CH$_2$OCH$_2$CF$_3$, —CH$_2$OCOCH$_3$, —CH$_2$NH$_2$, —CH$_2$NHCH$_3$, —CH$_2$N(CH$_3$)$_2$, —CH$_2$NHCH$_2$CH$_3$, —CH$_2$N(CH$_3$)CH$_2$CH$_3$, —CH$_2$NHCH$_2$CH$_2$CH$_3$, —CH$_2$NHCH(CH$_3$)$_2$, —CH$_2$NHCH(CH$_2$)$_2$, —CH$_2$N(CH$_2$CH$_3$)$_2$, —CH$_2$CH$_2$F, —CH$_2$CH$_2$Cl, —CH$_2$CH$_2$Br, —CH$_2$CH$_2$I, —CH$_2$CH$_2$OH, —CH$_2$CH$_2$OCOCH$_3$, —CH$_2$CH$_2$NH$_2$, —CH$_2$CH$_2$N(CH$_3$)$_2$, —CH$_2$CH$_2$NHCH$_2$CH$_3$, —CH$_2$CH$_2$N(CH$_3$)CH$_2$CH$_3$, —CH$_2$CH$_2$NHCH$_2$CH$_2$CH$_3$, —CH$_2$CH$_2$NHCH(CH$_3$)$_2$, —CH$_2$CH$_2$NHCH(CH$_2$)$_2$, —CH$_2$CH$_2$N(CH$_2$CH$_3$)$_2$, —CH$_2$CH$_2$NHCO$_2$C(CH$_3$)$_3$, and —CH$_2$Si(CH$_3$)$_3$.

The term "heteroatom-unsubstituted C$_n$-alkenyl" refers to a radical having a linear or branched, cyclic or acyclic structure, further having at least one nonaromatic carbon-carbon double bond, but no carbon-carbon triple bonds, a total of n carbon atoms, three or more hydrogen atoms, and no heteroatoms. For example, a heteroatom-unsubstituted C$_2$-C$_{10}$-alkenyl has 2 to 10 carbon atoms. Heteroatom-unsubstituted alkenyl groups include: —CH=CH$_2$, —CH=CHCH$_3$, —CH=CHCH$_2$CH$_3$, —CH=CHCH$_2$CH$_2$CH$_3$, —CH=CHCH(CH$_3$)$_2$, —CH=CHCH(CH$_2$)$_2$, —CH$_2$CH=CH$_2$, —CH$_2$CH=CHCH$_3$, —CH$_2$CH=CHCH$_2$CH$_3$, —CH$_2$CH=CHCH$_2$CH$_2$CH$_3$, —CH$_2$CH=CHCH(CH$_3$)$_2$, —CH$_2$CH=CHCH(CH$_2$)$_2$, and —CH=CH—C$_6$H$_5$. The term "heteroatom-substituted C$_n$-alkenyl" refers to a radical having a single nonaromatic carbon atom as the point of attachment and at least one nonaromatic carbon-carbon double bond, but no carbon-carbon triple bonds, further having a linear or branched, cyclic or acyclic structure, further having a total of n carbon atoms, 0, 1, or more than one hydrogen atom, and at least one heteroatom, wherein each heteroatom is independently selected from the group consisting of N, O, F, Cl, Br, I, Si, P, and S. For example, a heteroatom-substituted C$_2$-C$_{10}$-alkenyl has 2 to 10 carbon atoms. The groups, —CH=CHF, —CH=CHCl and —CH=CHBr, are examples of heteroatom-substituted alkenyl groups.

The term "heteroatom-unsubstituted C$_n$-alkynyl" refers to a radical having a linear or branched, cyclic or acyclic structure, further having at least one carbon-carbon triple bond, a total of n carbon atoms, at least one hydrogen atom, and no heteroatoms. For example, a heteroatom-unsubstituted C$_2$-C$_{10}$-alkynyl has 2 to 10 carbon atoms. The groups, —C≡CH, —C≡CCH$_3$, and —C≡CC$_6$H$_5$ are examples of heteroatom-unsubstituted alkynyl groups. The term "heteroatom-substituted C$_n$-alkynyl" refers to a radical having a single nonaromatic carbon atom as the point of attachment and at least one carbon-carbon triple bond, further having a linear or branched, cyclic or acyclic structure, and having a total of n carbon atoms, 0, 1, or more than one hydrogen atom, and at least one heteroatom, wherein each heteroatom is independently selected from the group consisting of N, O, F, Cl, Br, I, Si, P, and S. For example, a heteroatom-substituted C$_2$-C$_{10}$-alkynyl has 2 to 10 carbon atoms. The group, —C≡CSi(CH$_3$)$_3$, is an example of a heteroatom-substituted alkynyl group.

The term "heteroatom-unsubstituted C$_n$-aryl" refers to a radical having a single carbon atom as a point of attachment, wherein the carbon atom is part of an aromatic ring structure containing only carbon atoms, further having a total of n carbon atoms, 5 or more hydrogen atoms, and no heteroatoms. For example, a heteroatom-unsubstituted C$_6$-C$_{10}$-aryl has 6 to 10 carbon atoms. Examples of heteroatom-unsubstituted aryl groups include phenyl, methylphenyl, (dimethyl)phenyl, —C$_6$H$_4$CH$_2$CH$_3$, —C$_6$H$_4$CH$_2$CH$_2$CH$_3$, —C$_6$H$_4$CH(CH$_3$)$_2$, —C$_6$H$_4$CH(CH$_2$)$_2$, —C$_6$H$_3$(CH$_3$)CH$_2$CH$_3$, —C$_6$H$_4$CH=CH$_2$, —C$_6$H$_4$CH=CHCH$_3$, —C$_6$H$_4$C≡CH, —C$_6$H$_4$C≡CCH$_3$, naphthyl, and the radical derived from biphenyl. The term "heteroatom-unsubstituted aryl" includes carbocyclic aryl groups, biaryl groups, and radicals derived from polycyclic fused hydrocarbons (PAHs). The term "heteroatom-substituted C$_n$-aryl" refers to a radical having either a single aromatic carbon atom or a single aromatic heteroatom as the point of attachment, further having a total of n carbon atoms, at least one hydrogen atom, and at least one heteroatom, further wherein each heteroatom is independently selected from the group consisting of N, O, F, Cl, Br, I, Si, P, and S. For example, a heteroatom-unsubstituted C$_1$-C$_{10}$-heteroaryl has 1 to 10 carbon atoms. The term "heteroatom-substituted aryl" includes heteroaryl groups. It also includes those groups derived from the compounds: pyrrole, furan, thiophene, imidazole, oxazole, isoxazole, thiazole, isothiazole, triazole, pyrazole, pyridine, pyrazine, pyridazine, pyrimidine, and the like. Further examples of heteroatom-substituted aryl groups include the groups: —C$_6$H$_4$F, —C$_6$H$_4$Cl, —C$_6$H$_4$Br, —C$_6$H$_4$I, —C$_6$H$_4$OH, —C$_6$H$_4$OCH$_3$, —C$_6$H$_4$OCH$_2$CH$_3$, —C$_6$H$_4$OCOCH$_3$, —C$_6$H$_4$OC$_6$H$_5$, —C$_6$H$_4$NH$_2$, —C$_6$H$_4$NHCH$_3$, —C$_6$H$_4$NHCH$_2$CH$_3$, —C$_6$H$_4$CH$_2$Cl, —C$_6$H$_4$CH$_2$Br, —C$_6$H$_4$CH$_2$OH, —C$_6$H$_4$CH$_2$OCOCH$_3$, —C$_6$H$_4$CH$_2$NH$_2$, —C$_6$H$_4$N(CH$_3$)$_2$, —C$_6$H$_4$CH$_2$Cl, —C$_6$H$_4$CH$_2$CH$_2$OH, —C$_6$H$_4$CH$_2$CH$_2$OCOCH$_3$, —C$_6$H$_4$CH$_2$CH$_2$NH$_2$, —$C_6H_4CH_2CH=CH_2$, —$C_6H_4CF_3$, —$C_6H_4CN$, —$C_6H_4C\equiv CSi(CH_3)_3$, —$C_6H_4COH$, —$C_6H_4COCH_3$, —$C_6H_4COCH_2CH_3$, —$C_6H_4COCH_2CF_3$, —$C_6H_4COC_6H_5$, —$C_6H_4CO_2H$, —$C_6H_4CO_2CH_3$, —$C_6H_4CONH_2$, —$C_6H_4CONHCH_3$, —$C_6H_4CON(CH_3)_2$, furanyl, thienyl, pyridyl, pyrrolyl, pyrimidyl, pyrazinyl, imidazoyl, quinolyl and indolyl.

The term "heteroatom-unsubstituted $C_n$-aralkyl" refers to a radical having a single saturated carbon atom as the point of attachment, further having a total of n carbon atoms, wherein at least 6 of the carbon atoms form an aromatic ring structure containing only carbon atoms, 7 or more hydrogen atoms, and no heteroatoms. For example, a heteroatom-unsubstituted $C_7$-$C_{10}$-aralkyl has 7 to 10 carbon atoms. Examples of heteroatom-unsubstituted aralkyls include phenylmethyl (benzyl) and phenylethyl. The term "heteroatom-substituted $C_n$-aralkyl" refers to a radical having a single saturated carbon atom as the point of attachment, further having a total of n carbon atoms, 0, 1, or more than one hydrogen atom, and at least one heteroatom, wherein at least one of the carbon atoms is incorporated in an aromatic ring structure, further wherein each heteroatom is independently selected from the group consisting of N, O, F, Cl, Br, I, Si, P, and S. For example, a heteroatom-substituted $C_2$-$C_{10}$-heteroaralkyl has 2 to 10 carbon atoms.

The term "heteroatom-unsubstituted $C_n$-acyl" refers to a radical having a single carbon atom of a carbonyl group as the point of attachment, further having a linear or branched, cyclic or acyclic structure, further having a total of n carbon atoms, 1 or more hydrogen atoms, a total of one oxygen atom, and no additional heteroatoms. For example, a heteroatom-unsubstituted $C_1$-$C_{10}$-acyl has 1 to 10 carbon atoms. The groups, —COH, —$COCH_3$, —$COCH_2CH_3$, —$COCH_2CH_2CH_3$, —$COCH(CH_3)_2$, —$COCH(CH_2)_2$, —$COC_6H_5$, —$COC_6H_4CH_3$, —$COC_6H_4CH_2CH_3$, —$COC_6H_4CH_2CH_2CH_3$, —$COC_6H_4CH(CH_3)_2$, —$COC_6H_4CH(CH_2)_2$, and —$COC_6H_3(CH_3)_2$, are examples of heteroatom-unsubstituted acyl groups. The term "heteroatom-substituted $C_n$-acyl" refers to a radical having a single carbon atom as the point of attachment, the carbon atom being part of a carbonyl group, further having a linear or branched, cyclic or acyclic structure, further having a total of n carbon atoms, 0, 1, or more than one hydrogen atom, at least one additional heteroatom in addition to the oxygen of the carbonyl group, wherein each additional heteroatom is independently selected from the group consisting of N, O, F, Cl, Br, I, Si, P, and S. For example, a heteroatom-substituted $C_1$-$C_{10}$-acyl has 1 to 10 carbon atoms. The term heteroatom-substituted acyl includes carbamoyl, thiocarboxylate, and thiocarboxylic acid groups. The groups, —$COCH_2CF_3$, —$CO_2H$, —$CO_2CH_3$, —$CO_2CH_2CH_3$, —$CO_2CH_2CH_2CH_3$, —$CO_2CH(CH_3)_2$, —$CO_2CH(CH_2)_2$, —$CONH_2$, —$CONHCH_3$, —$CONHCH_2CH_3$, —$CONHCH_2CH_2CH_3$, —$CONHCH(CH_3)_2$, —$CONHCH(CH_2)_2$, —$CON(CH_3)_2$, —$CON(CH_2CH_3)CH_3$, —$CON(CH_2CH_3)_2$ and —$CONHCH_2CF_3$, are examples of heteroatom-substituted acyl groups.

The term "heteroatom-unsubstituted $C_n$-alkoxy" refers to a group, having the structure —OR, in which R is a heteroatom-unsubstituted $C_n$-alkyl, as that term is defined above. Heteroatom-unsubstituted alkoxy groups include: —$OCH_3$, —$OCH_2CH_3$, —$OCH_2CH_2CH_3$, —$OCH(CH_3)_2$, and —$OCH(CH_2)_2$. The term "heteroatom-substituted $C_n$-alkoxy" refers to a group, having the structure —OR, in which R is a heteroatom-substituted $C_n$-alkyl, as that term is defined above. For example, —$OCH_2CF_3$ is a heteroatom-substituted alkoxy group.

The term "heteroatom-unsubstituted $C_n$-alkenyloxy" refers to a group, having the structure —OR, in which R is a heteroatom-unsubstituted $C_n$-alkenyl, as that term is defined above. The term "heteroatom-substituted $C_n$-alkenyloxy" refers to a group, having the structure —OR, in which R is a heteroatom-substituted $C_n$-alkenyl, as that term is defined above.

The term "heteroatom-unsubstituted $C_n$-alkynyloxy" refers to a group, having the structure —OR, in which R is a heteroatom-unsubstituted $C_n$-alkynyl, as that term is defined above. The term "heteroatom-substituted $C_n$-alkynyloxy" refers to a group, having the structure —OR, in which R is a heteroatom-substituted $C_n$-alkynyl, as that term is defined above.

The term "heteroatom-unsubstituted $C_n$-aryloxy" refers to a group, having the structure —OAr, in which Ar is a heteroatom-unsubstituted $C_n$-aryl, as that term is defined above. An example of a heteroatom-unsubstituted aryloxy group is —$OC_6H_5$. The term "heteroatom-substituted $C_n$-aryloxy" refers to a group, having the structure —OAr, in which Ar is a heteroatom-substituted $C_n$-aryl, as that term is defined above.

The term "heteroatom-unsubstituted $C_n$-aralkyloxy" refers to a group, having the structure —$OR_{Ar}$, in which $R_{Ar}$ is a heteroatom-unsubstituted $C_n$-aralkyl, as that term is defined above. The term "heteroatom-substituted $C_n$-aralkyloxy" refers to a group, having the structure —$OR_{Ar}$, in which $R_{Ar}$ is a heteroatom-substituted $C_n$-aralkyl, as that term is defined above.

The term "heteroatom-unsubstituted $C_n$-acyloxy" refers to a group, having the structure —OAc, in which Ac is a heteroatom-unsubstituted $C_n$-acyl, as that term is defined above. A heteroatom-unsubstituted acyloxy group includes alkylcarbonyloxy and arylcarbonyloxy groups. For example, —$OCOCH_3$ is an example of a heteroatom-unsubstituted acyloxy group. The term "heteroatom-substituted $C_n$-acyloxy" refers to a group, having the structure —OAc, in which Ac is a heteroatom-substituted $C_n$-acyl, as that term is defined above. A heteroatom-substituted acyloxy group includes alkoxycarbonyloxy, aryloxycarbonyloxy, carboxylate, alkylcarbonyl, alkoxycarbonyl, aminocarbonyl, and alkylthiocarbonyl groups.

The term "heteroatom-unsubstituted $C_n$-alkylamino" refers to a radical having a single nitrogen atom as the point of attachment, further having one or two saturated carbon atoms attached to the nitrogen atom, further having a linear or branched, cyclic or acyclic structure, containing a total of n carbon atoms, all of which are nonaromatic, 4 or more hydrogen atoms, a total of 1 nitrogen atom, and no additional heteroatoms. For example, a heteroatom-unsubstituted $C_1$-$C_{10}$-alkylamino has 1 to 10 carbon atoms. The term "heteroatom-unsubstituted $C_n$-alkylamino" includes groups, having the structure —NHR, in which R is a heteroatom-unsubstituted $C_n$-alkyl, as that term is defined above. A heteroatom-unsubstituted alkylamino group would include —$NHCH_3$, —$NHCH_2CH_3$, —$NHCH_2CH_2CH_3$, —$NHCH(CH_3)_2$, —$NHCH(CH_2)_2$, —$NHCH_2CH_2CH_2CH_3$, —$NHCH(CH_3)CH_2CH_3$, —$NHCH_2CH(CH_3)_2$, —$NHC(CH_3)_3$, —$N(CH_3)_2$, —$N(CH_3)CH_2CH_3$, —$N(CH_2CH_3)_2$, N-pyrrolidinyl, and N-piperidinyl. The term "heteroatom-substituted $C_n$-alkylamino" refers to a radical having a single nitrogen atom as the point of attachment, further having one or two saturated carbon atoms attached to the nitrogen atom, no carbon-carbon double or triple bonds, further having a linear or branched, cyclic or acyclic structure, further having a total of n carbon atoms, all of which are nonaromatic, 0, 1, or more than one hydrogen atom, and at least one additional heteroatom, that is, in addition to the nitrogen atom at the point of attachment, wherein each additional heteroatom is independently selected from the group consisting of N, O, F, Cl, Br, I, Si, P, and S. For example, a heteroatom-substituted $C_1$-$C_{10}$-alkylamino has 1 to 10 carbon atoms. The term "heteroatom-substituted $C_n$-alkylamino" includes groups, having the structure —NHR, in which R is a heteroatom-substituted $C_n$-alkyl, as that term is defined above.

The term "heteroatom-unsubstituted $C_n$-alkenylamino" refers to a radical having a single nitrogen atom as the point of attachment, further having one or two carbon atoms attached to the nitrogen atom, further having a linear or branched, cyclic or acyclic structure, containing at least one nonaromatic carbon-carbon double bond, a total of n carbon atoms, 4 or more hydrogen atoms, a total of one nitrogen atom, and no additional heteroatoms. For example, a heteroatom-unsubstituted $C_2$-$C_{10}$-alkenylamino has 2 to 10 carbon atoms. The term "heteroatom-unsubstituted $C_n$-alkenylamino" includes groups, having the structure —NHR, in which R is a heteroatom-unsubstituted $C_n$-alkenyl, as that term is defined above. Examples of heteroatom-unsubstituted C-alkenylamino groups also include dialkenylamino and alkyl(alkenyl)amino groups. The term "heteroatom-substituted $C_n$-alkenylamino" refers to a radical having a single nitrogen atom as the point of attachment and at least one nonaromatic carbon-carbon double bond, but no carbon-carbon triple bonds, further having one or two carbon atoms attached to the nitrogen atom, further having a linear or branched, cyclic or acyclic structure, further having a total of n carbon atoms, 0, 1, or more than one hydrogen atom, and at least one additional heteroatom, that is, in addition to the nitrogen atom at the point of attachment, wherein each additional heteroatom is independently selected from the group consisting of N, O, F, Cl, Br, I, Si, P, and S. For example, a heteroatom-substituted $C_2$-$C_{10}$-alkenylamino has 2 to 10 carbon atoms. The term "heteroatom-substituted $C_n$-alkenylamino" includes groups, having the structure —NHR, in which R is a heteroatom-substituted $C_n$-alkenyl, as that term is defined above.

The term "heteroatom-unsubstituted $C_n$-alkynylamino" refers to a radical having a single nitrogen atom as the point of attachment, further having one or two carbon atoms attached to the nitrogen atom, further having a linear or branched, cyclic or acyclic structure, containing at least one carbon-carbon triple bond, a total of n carbon atoms, at least one hydrogen atoms, a total of one nitrogen atom, and no additional heteroatoms. For example, a heteroatom-unsubstituted $C_2$-$C_{10}$-alkynylamino has 2 to 10 carbon atoms. The term "heteroatom-unsubstituted $C_n$-alkynylamino" includes groups, having the structure —NHR, in which R is a heteroatom-unsubstituted $C_n$-alkynyl, as that term is defined above. An alkynylamino group includes dialkynylamino and alkyl(alkynyl)amino groups. The term "heteroatom-substituted $C_n$-alkynylamino" refers to a radical having a single nitrogen atom as the point of attachment, further having one or two carbon atoms attached to the nitrogen atom, further having at least one nonaromatic carbon-carbon triple bond, further having a linear or branched, cyclic or acyclic structure, and further having a total of n carbon atoms, 0, 1, or more than one hydrogen atom, and at least one additional heteroatom, that is, in addition to the nitrogen atom at the point of attachment, wherein each additional heteroatom is independently selected from the group consisting of N, O, F, Cl, Br, I, Si, P, and S. For example, a heteroatom-substituted $C_2$-$C_{10}$-alkynylamino has 2 to 10 carbon atoms. The term "heteroatom-substituted $C_n$-alkynylamino" includes groups, having the structure —NHR, in which R is a heteroatom-substituted $C_n$-alkynyl, as that term is defined above.

The term "heteroatom-unsubstituted $C_n$-arylamino" refers to a radical having a single nitrogen atom as the point of attachment, further having at least one aromatic ring structure attached to the nitrogen atom, wherein the aromatic ring structure contains only carbon atoms, further having a total of n carbon atoms, 6 or more hydrogen atoms, a total of one nitrogen atom, and no additional heteroatoms. For example, a heteroatom-unsubstituted $C_6$-$C_{10}$-arylamino has 6 to 10 carbon atoms. The term "heteroatom-unsubstituted $C_n$-arylamino" includes groups, having the structure —NHR, in which R is a heteroatom-unsubstituted $C_n$-aryl, as that term is defined above. A heteroatom-unsubstituted arylamino group includes diarylamino and alkyl(aryl)amino groups. The term "heteroatom-substituted $C_n$-arylamino" refers to a radical having a single nitrogen atom as the point of attachment, further having a total of n carbon atoms, at least one hydrogen atom, at least one additional heteroatoms, that is, in addition to the nitrogen atom at the point of attachment, wherein at least one of the carbon atoms is incorporated into one or more aromatic ring structures, further wherein each additional heteroatom is independently selected from the group consisting of N, O, F, Cl, Br, I, Si, P, and S. For example, a heteroatom-substituted $C_6$-$C_{10}$-arylamino has 6 to 10 carbon atoms. The term "heteroatom-substituted $C_n$-arylamino" includes groups, having the structure —NHR, in which R is a heteroatom-substituted $C_n$-aryl, as that term is defined above. A heteroatom-substituted arylamino group includes heteroarylamino groups.

The term "heteroatom-unsubstituted $C_n$-aralkylamino" refers to a radical having a single nitrogen atom as the point of attachment, further having one or two saturated carbon atoms attached to the nitrogen atom, further having a total of n carbon atoms, wherein at least 6 of the carbon atoms form an aromatic ring structure containing only carbon atoms, 8 or more hydrogen atoms, a total of one nitrogen atom, and no additional heteroatoms. For example, a heteroatom-unsubstituted $C_7$-$C_{10}$-aralkylamino has 7 to 10 carbon atoms. The term "heteroatom-unsubstituted $C_n$-aralkylamino" includes groups, having the structure —NHR, in which R is a heteroatom-unsubstituted $C_n$-aralkyl, as that term is defined above. An aralkylamino group includes diaralkylamino groups. The term "heteroatom-substituted $C_n$-aralkylamino" refers to a radical having a single nitrogen atom as the point of attachment, further having at least one or two saturated carbon atoms attached to the nitrogen atom, further having a total of n carbon atoms, 0, 1, or more than one hydrogen atom, at least one additional heteroatom, that is, in addition to the nitrogen atom at the point of attachment, wherein at least one of the carbon atom incorporated into an aromatic ring, further wherein each heteroatom is independently selected from the group consisting of N, O, F, Cl, Br, I, Si, P, and S. For example, a heteroatom-substituted $C_7$-$C_{10}$-aralkylamino has 7 to 10 carbon atoms. The term "heteroatom-substituted $C_n$-aralkylamino" includes groups, having the structure —NHR, in which R is a heteroatom-substituted $C_n$-aralkyl, as that term is defined above. The term "heteroatom-substituted aralkylamino" includes the term "heteroaralkylamino."

The term amido includes N-alkyl-amido, N-aryl-amido, N-aralkyl-amido, acylamino, alkylcarbonylamino, arylcarbonylamino, and ureido groups. The group, —NHCOCH$_3$, is an example of a heteroatom-unsubstituted amido group. The term "heteroatom-unsubstituted $C_n$-amido" refers to a radical having a single nitrogen atom as the point of attachment, further having a carbonyl group attached via its carbon atom to the nitrogen atom, further having a linear or branched, cyclic or acyclic structure, further having a total of n carbon atoms, 1 or more hydrogen atoms, a total of one oxygen atom, a total of one nitrogen atom, and no additional heteroatoms. For example, a heteroatom-unsubstituted $C_1$-$C_{10}$-amido has 1 to 10 carbon atoms. The term "heteroatom-unsubstituted $C_n$-amido" includes groups, having the structure —NHR, in which R is a heteroatom-unsubstituted $C_n$-acyl, as that term is defined above. The term "heteroatom-substituted $C_n$-amido" refers to a radical having a single nitrogen atom as the point of attachment, further having a carbonyl group attached via its carbon atom to the nitrogen atom, further having a linear or branched, cyclic or acyclic structure, further having a total of n aromatic or nonaromatic carbon atoms, 0, 1, or more than one hydrogen atom, at least one additional heteroatom in addition to the oxygen of the carbonyl group and the nitrogen atom at the point of attachment, wherein each additional heteroatom is independently selected from the group consisting of N, O, F, Cl, Br, I, Si, P, and S. For example, a heteroatom-substituted $C_1$-$C_{10}$-amido has 1 to 10 carbon atoms. The term "heteroatom-substituted $C_n$-amido" includes groups, having the structure —NHR, in which R is a heteroatom-unsubstituted $C_n$-acyl, as that term is defined above. The group, —NHCO$_2$CH$_3$, is an example of a heteroatom-substituted amido group.

In addition, atoms making up the compounds of the present invention are intended to include all isotopic forms of such atoms. Isotopes, as used herein, include those atoms having the same atomic number but different mass numbers. By way of general example and without limitation, isotopes of hydrogen include tritium and deuterium, and isotopes of carbon include $^{13}$C and $^{14}$C. Similarly, it is contemplated that one or more carbon atom(s) of a compound of the present invention may be replaced by a silicon atom(s). Similarly, it is contemplated that one or more oxygen atom(s) of a compound of the present invention may be replaced by a sulfur or a selenium atom(s).

Any undefined valency on an atom of a structure shown in this application implicitly represents a hydrogen atom bonded to the atom.

The use of the word "a" or "an," when used in conjunction with the term "comprising" in the claims and/or the specification may mean "one," but it is also consistent with the meaning of "one or more," "at least one," and "one or more than one."

Throughout this application, the term "about" is used to indicate that a value includes the inherent variation of error for the device, the method being employed to determine the value, or the variation that exists among the study subjects.

The terms "comprise," "have" and "include" are open-ended linking verbs. Any forms or tenses of one or more of these verbs, such as "comprises," "comprising," "has," "having," "includes" and "including," are also open-ended. For example, any method that "comprises," "has" or "includes" one or more steps is not limited to possessing only those one or more steps and also covers other unlisted steps.

The term "effective," as that term is used in the specification and/or claims, means adequate to accomplish a desired, expected, or intended result.

The term "hydrate" when used as a modifier to a compound means that the compound has less than one (e.g., hemihydrate), one (e.g., monohydrate), or more than one (e.g., dihydrate) water molecules associated with each compound molecule, such as in solid forms of the compound.

As used herein, the term "IC$_{50}$" refers to an inhibitory dose which is 50% of the maximum response obtained.

An "isomer" of a first compound is a separate compound in which each molecule contains the same constituent atoms as the first compound, but where the configuration of those atoms in three dimensions differs.

As used herein, the term "patient" or "subject" refers to a living mammalian organism, such as a human, monkey, cow, sheep, goat, dog, cat, mouse, rat, guinea pig, or transgenic species thereof. In certain embodiments, the patient or subject is a primate. Non-limiting examples of human subjects are adults, juveniles, infants and fetuses.

"Pharmaceutically acceptable" means that which is useful in preparing a pharmaceutical composition that is generally safe, non-toxic and neither biologically nor otherwise undesirable and includes that which is acceptable for veterinary use as well as human pharmaceutical use.

"Pharmaceutically acceptable salts" means salts of compounds of the present invention which are pharmaceutically acceptable, as defined above, and which possess the desired pharmacological activity. Such salts include acid addition salts formed with inorganic acids such as hydrochloric acid, hydrobromic acid, sulfuric acid, nitric acid, phosphoric acid, and the like; or with organic acids such as 1,2-ethanedisulfonic acid, 2-hydroxyethanesulfonic acid, 2-naphthalenesulfonic acid, 3-phenylpropionic acid, 4,4'-methylenebis(3-hydroxy-2-ene-1-carboxylic acid), 4-methylbicyclo[2.2.2]oct-2-ene-1-carboxylic acid, acetic acid, aliphatic mono- and dicarboxylicacids, aliphatic sulfuric acids, aromatic sulfuric acids, benzenesulfonic acid, benzoic acid, camphorsulfonic acid, carbonic acid, cinnamic acid, citric acid, cyclopentanepropionic acid, ethanesulfonic acid, fumaric acid, glucoheptonic acid, gluconic acid, glutamic acid, glycolic acid, heptanoic acid, hexanoic acid, hydroxynaphthoic acid, lactic acid, laurylsulfuric acid, maleic acid, malic acid, malonic acid, mandelic acid, methanesulfonic acid, muconic acid, o-(4-hydroxybenzoyl)benzoic acid, oxalic acid, p-chlorobenzenesulfonic acid, phenyl-substituted alkanoic acids, propionic acid, p-toluenesulfonic acid, pyruvic acid, salicylic acid, stearic acid, succinic acid, tartaric acid, tertiarybutylacetic acid, trimethylacetic acid, and the like. Pharmaceutically acceptable salts also include base addition salts which may be formed when acidic protons present are capable of reacting with inorganic or organic bases. Acceptable inorganic bases include sodium hydroxide, sodium carbonate, potassium hydroxide, aluminum hydroxide and calcium hydroxide. Acceptable organic bases include ethanolamine, diethanolamine, triethanolamine, tromethamine, N-methylglucamine and the like. It should be recognized that the particular anion or cation forming a part of any salt of this invention is not critical, so long as the salt, as a whole, is pharmacologically acceptable. Additional examples of pharmaceutically acceptable salts and their methods of preparation and use are presented in *Handbook of Pharmaceutical Salts: Properties, and Use* (P. H. Stahl & C. G. Wermuth eds., Verlag Helvetica Chimica Acta, 2002), As used herein, "predominantly one enantiomer" means that a compound contains at least about 85% of one enantiomer, or more preferably at least about 90% of one enantiomer, or even more preferably at least about 95% of one enantiomer, or most preferably at least about 99% of one enantiomer. Similarly, the phrase "substantially free from other optical isomers" means that the composition contains at most about 15% of another enantiomer or diastereomer, more preferably at most about 10% of another enantiomer or diastereomer, even more preferably at most about 5% of another enantiomer or diastereomer, and most preferably at most about 1% of another enantiomer or diastereomer.

"Prevention" or "preventing" includes: (1) inhibiting the onset of a disease in a subject or patient which may be at risk and/or predisposed to the disease but does not yet experience or display any or all of the pathology or symptomatology of the disease, and/or (2) slowing the onset of the pathology or symptomatology of a disease in a subject or patient which may be at risk and/or predisposed to the disease but does not yet experience or display any or all of the pathology or symptomatology of the disease.

The term "saturated" when referring to an atom means that the atom is connected to other atoms only by means of single bonds.

A "stereoisomer" or "optical isomer" is an isomer of a given compound in which the same atoms are bonded to the same other atoms, but where the configuration of those atoms in three dimensions differs. "Enantiomers" are stereoisomers of a given compound that are mirror images of each other, like left and right hands. "Diastereomers" are stereoisomers of a given compound that are not enantiomers.

"Therapeutically effective amount" or "pharmaceutically effective amount" means that amount which, when administered to a subject or patient for treating a disease, is sufficient to effect such treatment for the disease.

"Treatment" or "treating" includes (1) inhibiting a disease in a subject or patient experiencing or displaying the pathology or symptomatology of the disease (e.g., arresting further development of the pathology and/or symptomatology), (2) ameliorating a disease in a subject or patient that is experiencing or displaying the pathology or symptomatology of the disease (e.g., reversing the pathology and/or symptomatology), and/or (3) effecting any measurable decrease in a disease in a subject or patient that is experiencing or displaying the pathology or symptomatology of the disease.

As used herein, the term "water soluble" means that the compound dissolves in water at least to the extent of 0.010 mole/liter or is classified as soluble according to literature precedence.

Other abbreviations used herein are as follows: DMSO, dimethyl sulfoxide; NO, nitric oxide; iNOS, inducible nitric oxide synthase; COX-2, cyclooxygenase-2; NGF, nerve growth factor; IBMX, isobutylmethylxanthine; FBS, fetal bovine serum; GPDH, glycerol 3-phosphate dehydrogenase; RXR, retinoid X receptor; TGF-β, transforming growth factor-β; IFNγ or IFN-γ, interferon-γ; LPS, bacterial endotoxic lipopolysaccharide; TNFα or TNF-α, tumor necrosis factor-α; IL-1β, interleukin-1β; GAPDH, glyceraldehyde-3-phosphate dehydrogenase; MTBE, methyl-tert-butylether; MTT, 3-[4,5-dimethylthiazol-2-yl]-2,5-diphenyltetrazolium bromide; TCA, trichloroacetic acid; HO-1, inducible heme oxygenase.

The above definitions supersede any conflicting definition in any of the reference that is incorporated by reference herein.

III. Synthetic Triterpenoids

Triterpenoids, biosynthesized in plants by the cyclization of squalene, are used for medicinal purposes in many Asian countries; and some, like ursolic and oleanolic acids, are known to be anti-inflammatory and anti-carcinogenic (Huang et al., 1994; Nishino et al., 1988). However, the biological activity of these naturally-occurring molecules is relatively weak, and therefore the synthesis of new analogs to enhance their potency was undertaken (Honda et al., 1997; Honda et al., 1998). Subsequent research has identified a number of synthetic compounds that have improved activity as compared to the naturally-occurring triterpenoids.

The ongoing efforts for the improvement of anti-inflammatory and antiproliferative activity of oleanolic and ursolic acid analogs led to the discovery of 2-cyano-3,12-dioxooleane-1,9(11)-dien-28-oic acid (CDDO, RTA 402) and related compounds (e.g., CDDO-Me, TP-225, CDDO-Im) (Honda et al., 1997, 1998, 1999, 2000a, 2000b, 2002; Suh et al., 1998; 1999; 2003; Place et al., 2003; Liby et al., 2005). In the case of inducing cytoprotective genes through Keap1-Nrf2-antioxidant response element (ARE) signaling, a recent structure activity evaluation of 15 triterpenoids noted the importance of Michael acceptor groups on both the A and C rings, a nitrile group at C-2 of the A ring, and that substituents at C-17 affected pharmacodynamic action in vivo (Yates et al., 2007).

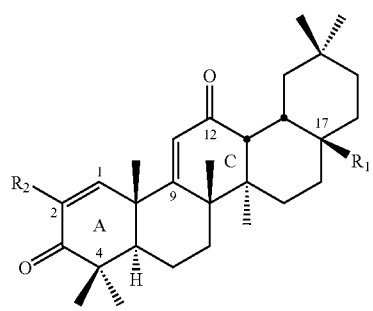

In general, CDDO is the prototype for a large number of compounds in a family of agents that have been shown useful in a variety of contexts. For example, CDDO-Me and CDDO-Im are reported to possess the ability to modulate transforming growth factor-β (TGF-β)/Smad signaling in several types of cells (Suh et al., 2003; Minns et al., 2004; Mix et al., 2004). Both are known to be potent inducers of heme-oxygenase-1 and Nrf2/ARE signaling (Liby et al., 2005), and a series of synthetic triterpenoid (TP) analogs of oleanolic acid have also been shown to be potent inducers of the phase 2 response, that is elevation of NAD(P)H-quinone oxidoreductase and heme oxygenase 1 (HO-1), which is a major protector of cells against oxidative and electrophile stress (Dinkova-Kostova et al., 2005). Like previously identified phase 2 inducers, the TP analogs were shown to use the antioxidant response element-Nrf2-Keap1 signaling pathway.

RTA 402 (bardoxolone methyl), one of the compounds for use with the methods of this invention, is an Antioxidant Inflammation Modulator (AIM) in clinical development for inflammation and cancer-related indications that inhibits immune-mediated inflammation by restoring redox homeostasis in inflamed tissues. It induces the cytoprotective transcription factor Nrf2 and suppresses the activities of the pro-oxidant and pro-inflammatory transcription factors NF-κB and STAT3. In vivo, RTA 402 has demonstrated significant single agent anti-inflammatory activity in several animal models of inflammation such as renal damage in the cisplatin model and acute renal injury in the ischemia-reperfusion model. In addition, significant reductions in serum creatinine have been observed in patients treated with RTA 402.

In one aspect of the invention, the compounds of the present invention may be used for treating a subject having a renal disease or condition caused by elevated levels of oxidative stress in one or more tissues. The oxidative stress may be accompanied by either acute or chronic inflammation. The oxidative stress may be caused by acute exposure to an external agent such as ionizing radiation or a cytotoxic chemotherapy agent (e.g., doxorubicin), by trauma or other acute tissue injury, by ischemia/reperfusion injury, by poor circulation or anemia, by localized or systemic hypoxia or hyperoxia, or by other abnormal physiological states such as hyperglycemia or hypoglycemia.

Accordingly, in pathologies involving oxidative stress alone or oxidative stress exacerbated by inflammation, treatment may comprise administering to a subject a therapeutically effective amount of a compound of this invention, such as those described above or throughout this specification. Treatment may be administered preventively in advance of a predictable state of oxidative stress (e.g., organ transplantation or the administration of therapy to a cancer patient), or it may be administered therapeutically in settings involving established oxidative stress and inflammation.

Newer amide derivatives of CDDO have now also been found to be promising agents, for example for their ability to pass through the blood brain barrier. In addition to the methyl amide of CDDO (CDDO-MA), as reported in Honda et al. (2002), the invention provides for the use of additional CDDO amide derivatives, such as the ethyl amide (CDDO-EA), as well fluorinated amide derivatives of CDDO, such as the 2,2,2-trifluoroethyl amide derivative of CDDO (CDDO-TFEA).

The compounds of the present invention can be prepared according to the methods taught by Honda et al. (1998), Honda et al. (2000b), Honda et al. (2002), Yates et al. (2007), and U.S. Pat. Nos. 6,326,507 and 6,974,801, which are all incorporated herein by reference.

Non-limiting examples of triterpenoids that may be used in accordance with the methods of this invention are shown here.

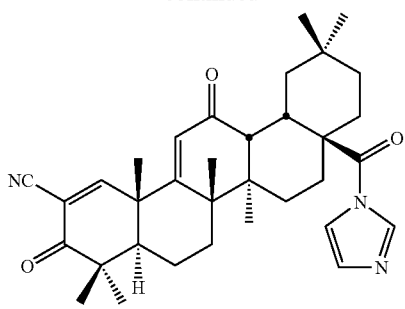

CDDO-Im
(TP-235)
(RTA 403)

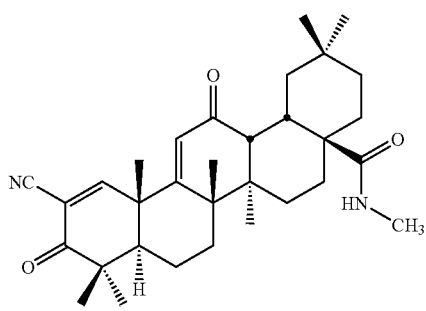

CDDO-MA
(TP-224)

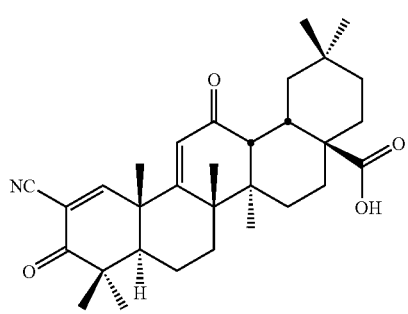

CDDO
(TP-151)
(RTA 401)

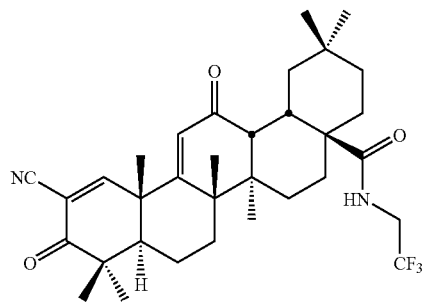

CDDP-TFEA
(TP-500)
(RTA 404)

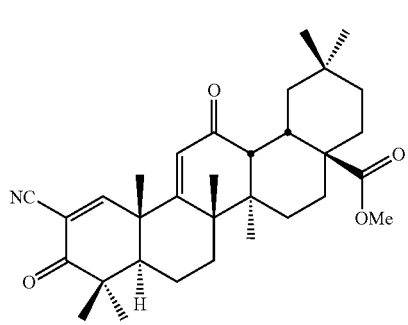

CDDO-Me
bardoxolone methyl
(TP-155)
(RTA 402)

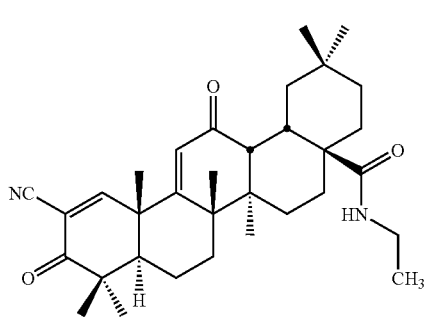

CDDO-EA
(TP-319)
(RTA 405)

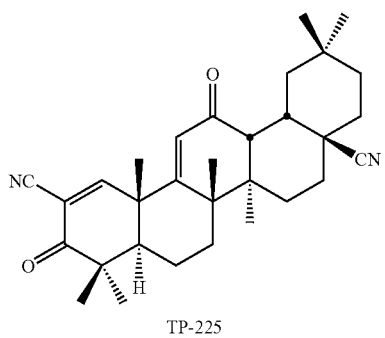

TP-225

The compounds for use with the present invention, such as those of the table above, are structurally similar to RTA 402 and in many cases exhibit similar biological properties, as has been noted above. As additional examples, Table 1 summarizes in vitro results for several of these compounds in which RAW264.7 macrophages were pre-treated with DMSO or drugs at various concentrations (nM) for 2 hours, then treated with 20 ng/ml IFNγ for 24 hours. NO concentration in media was determined using a Griess reagent system; cell viability was determined using WST-1 reagent. NQO1 CD represents the concentration required to induce a two-fold increase in the expression of NQO1, an Nrf2-regulated antioxidant enzyme, in Hepa1c1c7 murine hepatoma cells (Dinkova-Kostova et al., 2005). All these results are orders of magnitude more active than, for example, the parent oleanolic acid molecule. In part because induction of antioxidant pathways resulting from Nrf2 activation provides important protective effects against oxidative stress and inflammation, compounds related to RTA 402 may also provide significant benefits similar to those presented for RTA 402 in this application, and these related compounds may, therefore, be used for the treatment and/or prevention of diseases, such as: renal/kidney disease (RKD), insulin resistance, diabetes, endothelial dysfunction, fatty liver disease, cardiovascular disease (CVD), and related disorders.

TABLE 1

Suppression of IFNγ-induced NO production.

| Working ID | RAW264.7 (20 ng/ml IFNγ) | | Hepa1c1c7 cells |
|---|---|---|---|
| | NO IC$_{50}$ | WST-1 IC$_{50}$ | NQO1 CD |
| RTA 401 | ~10 nM | >200 nM | 2.3 nM |
| RTA 402 | 2.2 nM | 80 nM | 1.0 nM |
| RTA 403 | ~0.6 nM | 100 nM | 3.3 nM |
| RTA 404 | 5.8 nM | 100 nM | n/a |
| RTA 405 | 6 nM | ~200 nM | n/a |
| TP-225 | ~0.4 nM | 75 nM | 0.28 nM |

The synthesis of CDDO-MA is discussed in Honda et al. (2002), which is incorporated herein by reference. The syntheses of CDDO-EA and CDDO-TFEA are presented in Yates et al. (2007), which is incorporated herein by reference, and shown in the Scheme 1 below.

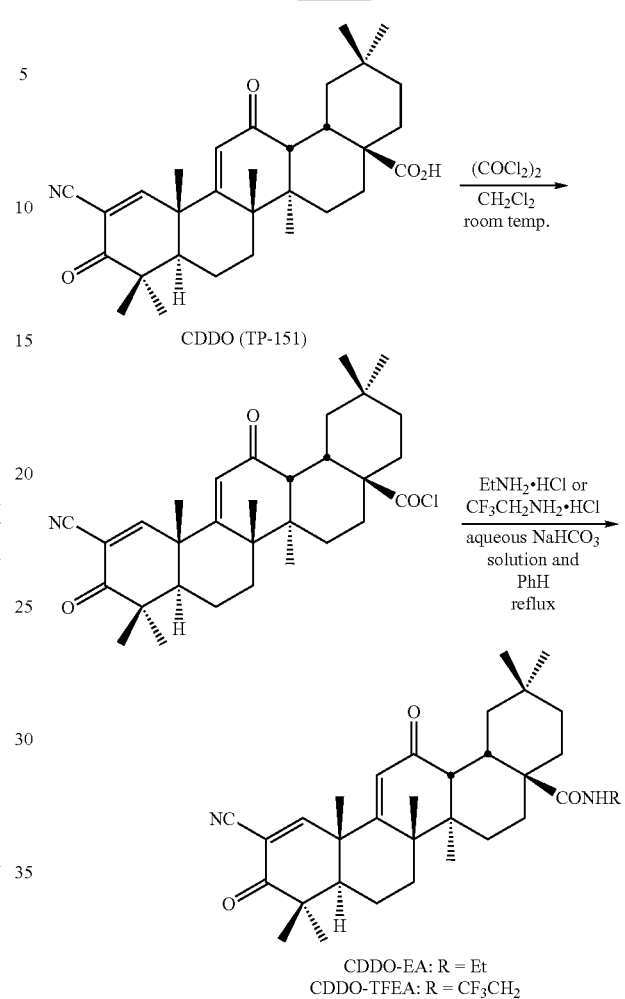

Scheme 1

CDDO (TP-151)

CDDO-EA: R = Et
CDDO-TFEA: R = CF$_3$CH$_2$

IV. Polymorphic Forms of CDDO-Me

Figure 15:
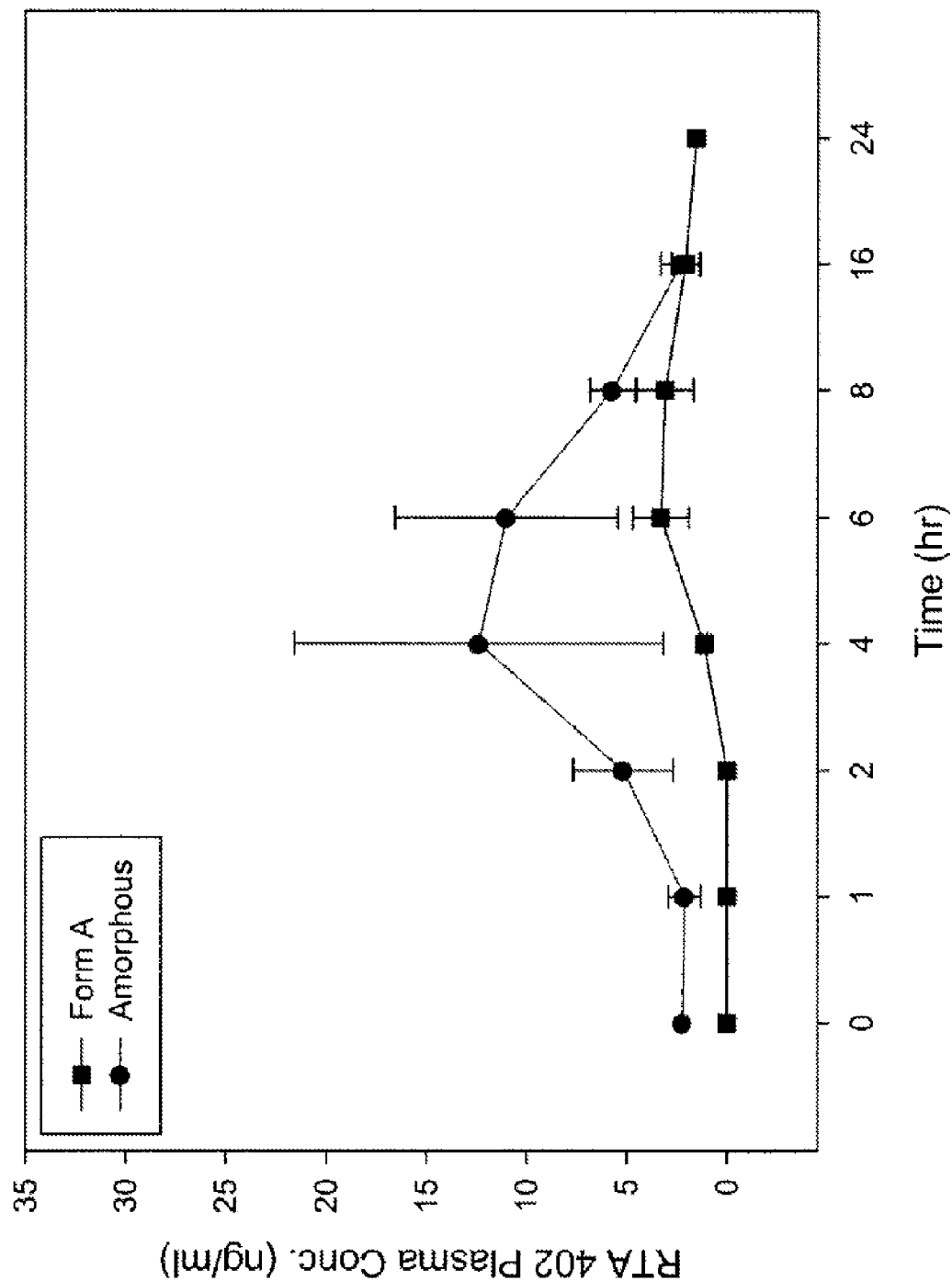
FIG. 15—Improved Bioavailability of Form B (Amorphous) in Cynomolgus Monkeys. The figure shows a representative plot of the area under the curve for Form A and Form B, following a 4.1 mg/kg oral administration to cynomolgus monkeys. Each data point represents the mean plasma concentration of CDDO methyl ester in 8 animals. Error bars represent the standard deviation within the sampled population.

Polymorphic forms of the compounds of the present invention, e.g., Forms A and B of CDDO-Me, may be used in accordance with the methods of this inventions. Form B displays a bioavailability that is surprisingly better than that of Form A (FIG. 15). Specifically the bioavailability of Form B was higher than that of Form A CDDO-Me in monkeys when the monkeys received equivalent dosages of the two forms orally, in gelatin capsules (U.S. application Ser. No. 12/191, 176, filed Aug. 13, 2008).

Figure 12:
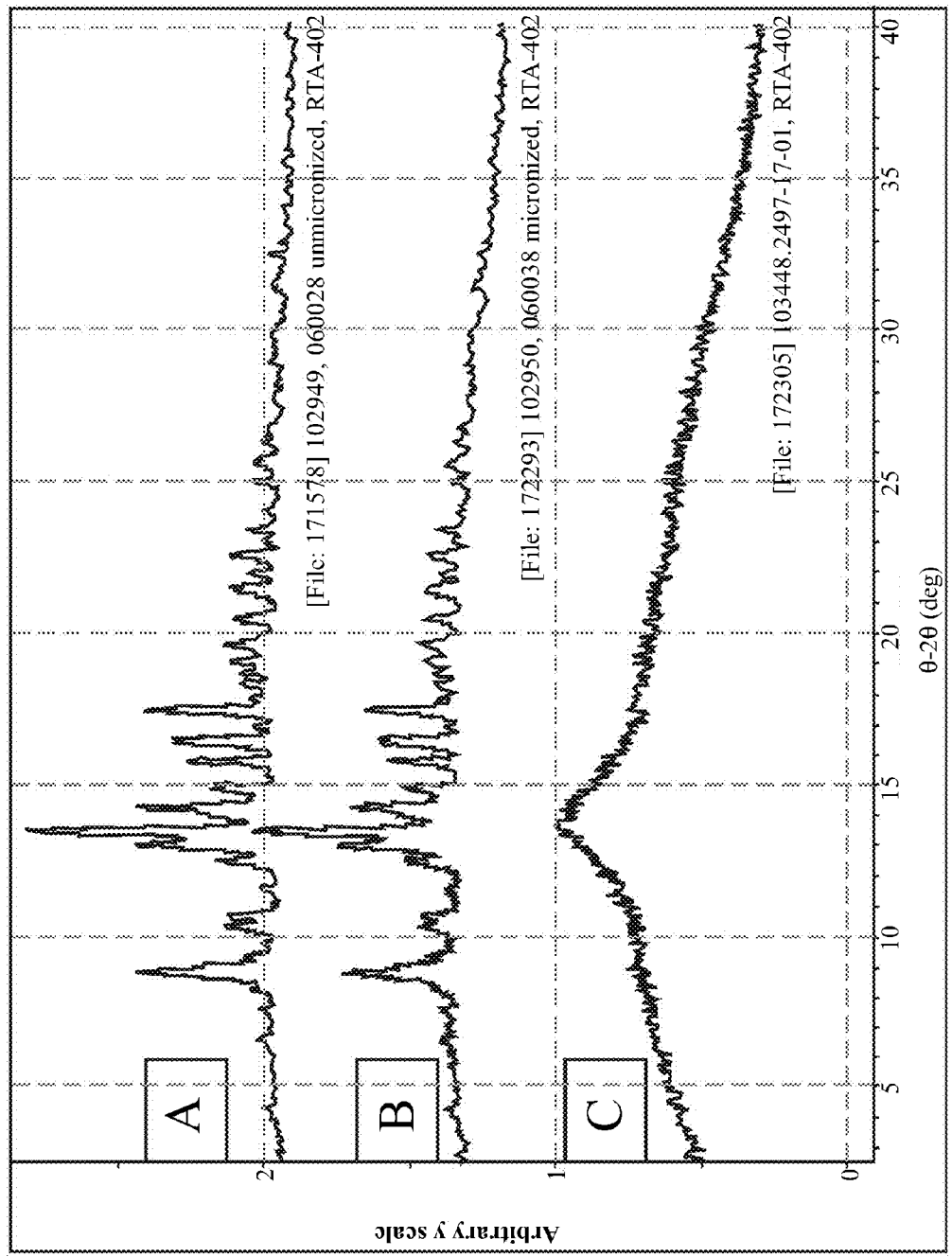
FIGS. 12A-C—X-ray Powder Diffraction (XRPD) Spectra of Forms A and B of RTA 402.

"Form A" of CDDO-Me (RTA 402) is unsolvated (non-hydrous) and can be characterized by a distinctive crystal structure, with a space group of P4$_3$2$_1$2 (no. 96) unit cell dimensions of a=14.2 Å, b=14.2 Å and c=81.6 Å, and by a packing structure, whereby three molecules are packed in helical fashion down the crystallographic b axis. In some embodiments, Form A can also be characterized by X-ray powder diffraction (XRPD) pattern (CuKα) comprising significant diffraction peaks at about 8.8, 12.9, 13.4, 14.2 and 17.4° 2θ. In some variations, the X-ray powder diffraction of Form A is substantially as shown in FIG. 12A or FIG. 12B.

Figure 14:
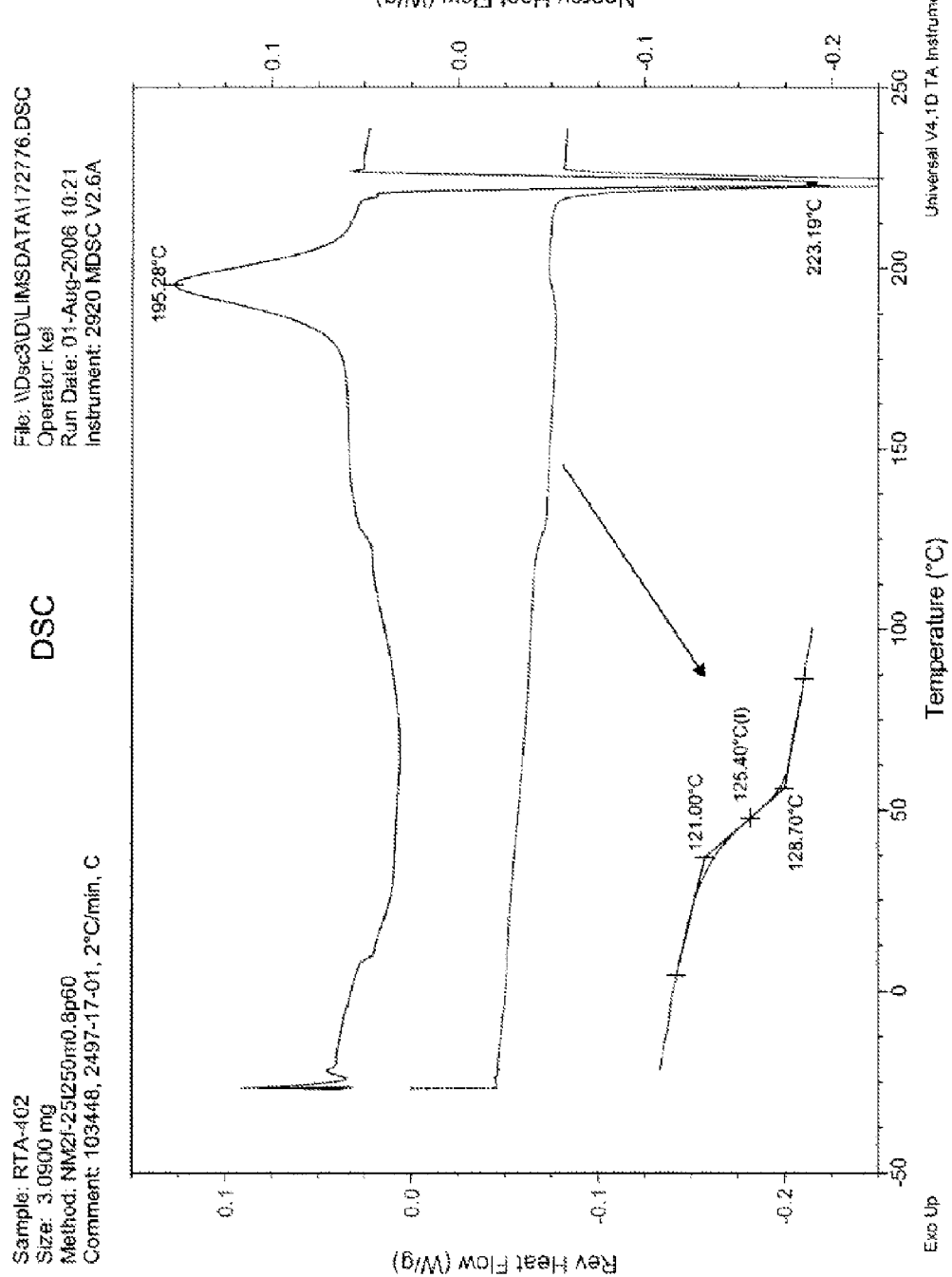
FIG. 14—Modulated Differential Scanning Calorimetry (MDSC) Curve of Form B RTA 402. The section of the curve shown in the expanded view is consistent with a glass transition temperature ($T_g$).

Unlike Form A, "Form B" of CDDO-Me is in a single phase but lacks such a defined crystal structure. Samples of Form B show no long-range molecular correlation, i.e., above roughly 20 Å. Moreover, thermal analysis of Form B samples reveals a glass transition temperature ($T_g$) in a range from about 120° C. to about 130° C. (FIG. 14). In contrast, a disordered nanocrystalline material does not display a $T_g$ but instead only a melting temperature ($T_m$), above which crystalline structure becomes a liquid. Form B is typified by an XRPD spectrum (FIG. 12C) differing from that of Form A (FIG. 12A or FIG. 12B). Since it does not have a defined crystal structure, Form B likewise lacks distinct XRPD peaks, such as those that typify Form A, and instead is characterized by a general "halo" XRPD pattern. In particular, the non-crystalline Form B falls into the category of "X-ray amorphous" solids because its XRPD pattern exhibits three or fewer primary diffraction halos. Within this category, Form B is a "glassy" material.

Form A and Form B of CDDO-Me are readily prepared from a variety of solutions of the compound. For example, Form B can be prepared by fast evaporation or slow evaporation in MTBE, THF, toluene, or ethyl acetate. Form A can be prepared in several ways, including via fast evaporation, slow evaporation, or slow cooling of a CDDO-Me solution in ethanol or methanol. Preparations of CDDO-Me in acetone can produce either Form A, using fast evaporation, or Form B, using slow evaporation.

Figure 13:
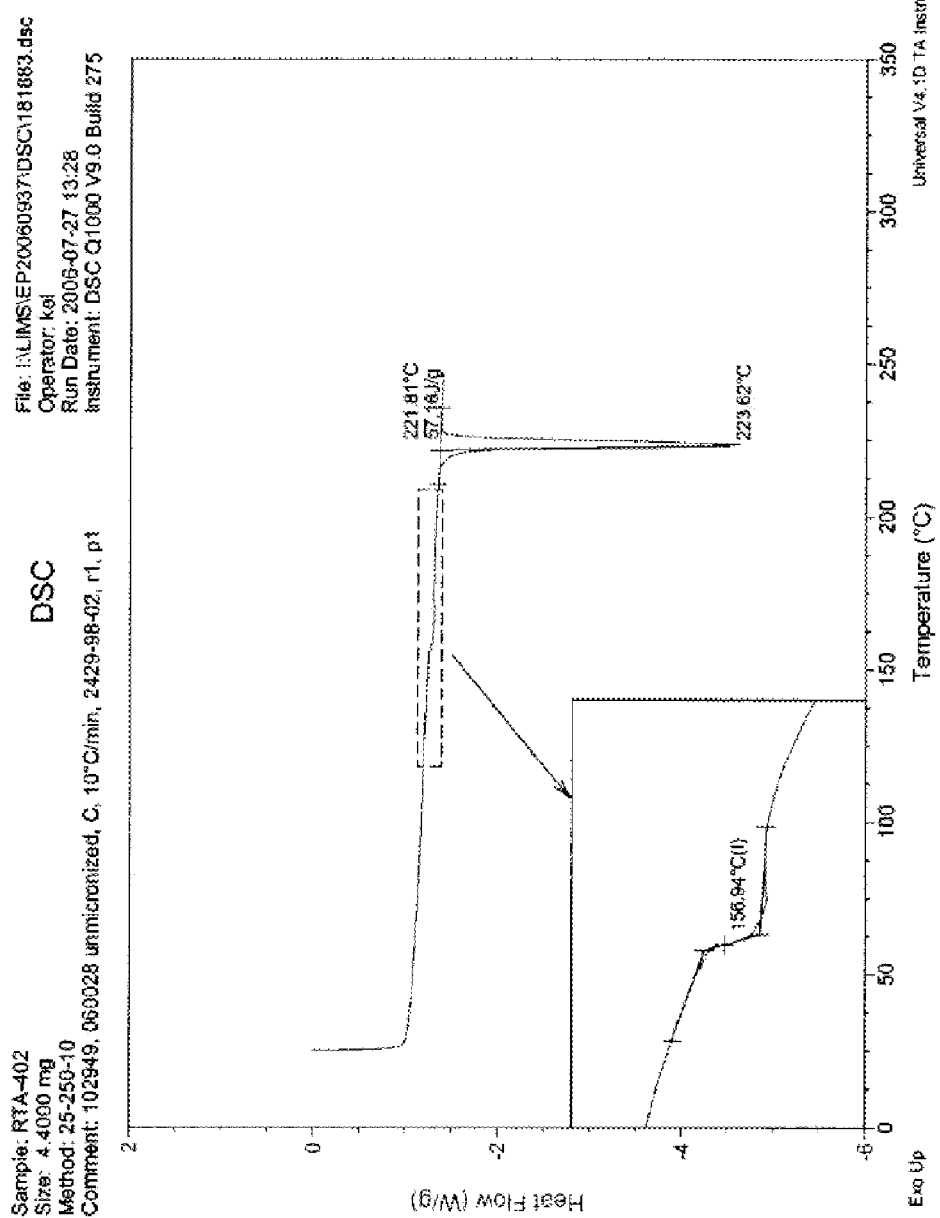
FIG. 13—Modulated Differential Scanning Calorimetry (MDSC) Curve of Form A RTA 402. The section of the curve shown in the expanded view is consistent with a glass transition temperature ($T_g$).

Various means of characterization can be used together to distinguish Form A and Form B CDDO-Me from each other and from other forms of CDDO-Me. Illustrative of the techniques suitable for this purpose are solid state Nuclear Magnetic Resonance (NMR), X-ray powder diffraction (compare FIGS. 12A & B with FIG. 12C), X-ray crystallography, Differential Scanning Calorimetry (DSC) (compare FIG. 13 with FIG. 14), dynamic vapor sorption/desorption (DVS), Karl Fischer analysis (KF), hot stage microscopy, modulated differential screening calorimetry, FT-IR, and Raman spectroscopy. In particular, analysis of the XRPD and DSC data can distinguish Form A, Form B, and a hemibenzenate forms of CDDO-Me (U.S. application Ser. No. 12/191,176, filed Aug. 13, 2008.)

Additional details regarding polymorphic forms of CDDO-Me are described in U.S. Provisional Application No. 60/955,939, filed Aug. 15, 2007, and the corresponding non-provisional U.S. application Ser. No. 12/191,176, filed Aug. 13, 2008, which are both incorporated herein by reference in their entireties.

V. Use of Triterpenoids for the Treatment of Chronic Kidney Disease, Insulin Resistance/Diabetes and Endothelial Dysfunction/Cardiovascular Disease The compounds and methods of this invention may be used for treating various aspects of renal/kidney disease, including both acute and chronic indications. In general, the method will comprise administering to the subjects pharmaceutically effective amounts of a compound of this invention.

Inflammation contributes significantly to the pathology of chronic kidney disease (CKD). There is also a strong mechanistic link between oxidative stress and renal dysfunction. The NF-κB signaling pathway plays an important role in the progression of CKD as NF-κB regulates the transcription of MCP-1, a chemokine that is responsible for the recruitment of monocytes/macrophages resulting in an inflammatory response that ultimately injures the kidney (Wardle, 2001). The Keap1/Nrf2/ARE pathway controls the transcription of several genes encoding antioxidant enzymes, including heme oxygenase-1 (HO-1). Ablation of the Nrf2 gene in female mice results in the development of lupus-like glomerular nephritis (Yoh et al., 2001; Ma et al., 2006). Furthermore, several studies have demonstrated that HO-1 expression is induced in response to renal damage and inflammation and that this enzyme and its products—bilirubin and carbon monoxide—play a protective role in the kidney (Nath et al., 2006).

The glomerulus and the surrounding Bowman's capsule constitute the basic functional unit of the kidney. Glomerular filtration rate (GFR) is the standard measure of renal function. Creatinine clearance is commonly used to measure GFR. However, the level of serum creatinine is commonly used as a surrogate measure of creatinine clearance. For instance, excessive levels of serum creatinine are generally accepted to indicate inadequate renal function and reductions in serum creatinine over time are accepted as an indication of improved renal function. Normal levels of creatinine in the blood are approximately 0.6 to 1.2 milligrams (mg) per deciliter (dl) in adult males and 0.5 to 1.1 milligrams per deciliter in adult females.

Acute kidney injury (AKI) can occur following ischemia-reperfusion, treatment with certain pharmacological agents such as cisplatin and rapamycin, and intravenous injection of radiocontrast media used in medical imaging. As in CKD, inflammation and oxidative stress contribute to the pathology of AKI. The molecular mechanisms underlying radiocontrast-induced nephropathy (RCN) are not well understood; however, it is likely that a combination of events including prolonged vasoconstriction, impaired kidney autoregulation, and direct toxicity of the contrast media all contribute to renal failure (Tumlin et al., 2006). Vasoconstriction results in decreased renal blood flow and causes ischemia-reperfusion and the production of reactive oxygen species. HO-1 is strongly induced under these conditions and has been demonstrated to prevent ischemia-reperfusion injury in several different organs, including the kidney (Nath et al., 2006). Specifically, induction of HO-1 has been shown to be protective in a rat model of RCN (Goodman et al., 2007). Reperfusion also induces an inflammatory response, in part though activation of NF-κB signaling (Nichols, 2004). Targeting NF-κB has been proposed as a therapeutic strategy to prevent organ damage (Zingarelli et al., 2003).

Without being bound by theory, the potency of the compounds of the present invention, e.g., RTA 402, is largely derived from the addition of α,β-unsaturated carbonyl groups. In vitro assays, most activity of the compounds can be abrogated by the introduction of dithiothreitol (DTT), N-acetyl cysteine (NAC), or glutathione (GSH); thiol containing moieties that interact with α,β-unsaturated carbonyl groups (Wang et al., 2000; Ikeda et al., 2003; 2004; Shishodia et al., 2006). Biochemical assays have established that RTA 402 directly interacts with a critical cysteine residue (C179) on IKKβ (see below) and inhibits its activity (Shishodia et al., 2006; Ahmad et al., 2006). IKKβ controls activation of NF-κB through the "classical" pathway which involves phosphorylation-induced degradation of IκB resulting in release of NF-κB dimers to the nucleus. In macrophages, this pathway is responsible for the production of many pro-inflammatory molecules in response to TNFα and other pro-inflammatory stimuli.

RTA 402 also inhibits the JAK/STAT signaling pathway at multiple levels. JAK proteins are recruited to transmembrane receptors (e.g., IL-6R) upon activation by ligands such as interferons and interleukins. JAKs then phosphorylate the intracellular portion of the receptor causing recruitment of STAT transcription factors. The STATs are then phosphorylated by JAKs, form dimers, and translocate to the nucleus where they activate transcription of several genes involved in inflammation. RTA 402 inhibits constitutive and IL-6-induced STAT3 phosphorylation and dimer formation and directly binds to cysteine residues in STAT3 (C259) and in the kinase domain of JAK1 (C1077). Biochemical assays have also established that the triterpenoids directly interact with critical cysteine residues on Keap1 (Dinkova-Kostova et al., 2005). Keap1 is an actin-tethered protein that keeps the transcription factor Nrf2 sequestered in the cytoplasm under normal conditions (Kobayashi & Yamamoto, 2005). Oxidative stress results in oxidation of the regulatory cysteine residues on Keap1 and causes the release of Nrf2. Nrf2 then translocates to the nucleus and binds to antioxidant response elements (AREs) resulting in transcriptional activation of many antioxidant and anti-inflammatory genes. Another target of the Keap1/Nrf2/ARE pathway is heme oxygenase 1 (HO-1). HO-1 breaks down heme into bilirubin and carbon monoxide and plays many antioxidant and anti-inflammatory roles (Maines & Gibbs, 2005). HO-1 has recently been shown to be potently induced by the triterpenoids (Liby et al., 2005), including RTA 402. RTA 402 and many structural analogs have also been shown to be potent inducers of the expression of other Phase 2 proteins (Yates et al., 2007).

RTA 402 is a potent inhibitor of NF-κB activation. Furthermore, RTA 402 activates the Keap1/Nrf2/ARE pathway and induces expression of HO-1. As described below, RTA 402 has demonstrated activity in two animal models of AKI. Furthermore, reduced serum creatinine levels and improvement of glomerular filtration have been observed in the majority of human patients that have been treated with RTA 402 (see Examples below). Significant improvements have now been observed in a Phase II study of patients with diabetic nephropathy. The findings indicate that RTA 402 may be used to improve renal function in patients with diabetic nephropathy through suppression of renal inflammation and improvement of glomerular filtration.

As noted above, both diabetes and essential hypertension are major risk factors for the development of chronic kidney disease and, ultimately, renal failure. Both of these conditions, along with indicators of systemic cardiovascular disease such as hyperlipidemia, are frequently present in the same patient, especially if that patient is clinically obese. Although the unifying factors are not completely understood, dysfunction of the vascular endothelium has been implicated as a significant pathological factor in systemic cardiovascular disease, chronic kidney disease, and diabetes (see, e.g., Zoccali, 2006). Acute or chronic oxidative stress in vascular endothelial cells has been implicated in the development of endothelial dysfunction, and is strongly associated with chronic inflammatory processes. Therefore, an agent capable of relieving oxidative stress and concomitant inflammation in the vascular endothelium may alleviate dysfunction and restore endothelial homeostasis. Without being bound by theory, compounds of the invention, by stimulating Nrf2-regulated endogenous antioxidant mechanisms, have shown the highly unusual ability to improve parameters related to renal function (e.g., serum creatinine and estimated glomerular filtration rate), glycemic control and insulin resistance (e.g., hemoglobin A1c), and systemic cardiovascular disease (e.g., circulating endothelial cells) in patients having abnormal clinical values for these parameters. Currently, combination therapy is typically required in such patients to achieve improvements in measures of glycemic control and cardiovascular disease, including the use of angiotensin-converting enzyme inhibitors or angiotensin II receptor blockers to alleviate hypertension and slow the progression of chronic kidney disease. By achieving simultaneous and clinically meaningful improvements in all of these parameters, especially measures of renal function, compounds of the invention represent a significant improvement over currently available therapies. In some aspects, the compounds of the present invention may be used to treat a combination of the above conditions as a single therapy, or in combination with fewer additional therapies than would currently be used.

These findings also indicate that administration of RTA 402 may be used to protect patients from kidney damage such as from exposure to radiocontrast agents, as in the case of radiocontrast-induced nephropathy (RCN), as well as in other contexts. In one aspect, the compounds of this invention may be used to treat ischemia-reperfusion- and/or chemotherapy-induced acute renal injury. For example, the results shown in Examples 2 and 3 below demonstrate that RTA 402 is protective in animal models of ischemia-reperfusion- and chemotherapy-induced acute renal injury.

Serum creatinine has been measured in several animal models treated with RTA 402. Significant reductions of serum creatinine levels relative to baseline levels or levels in control animals have been observed in cynomolgus monkeys, beagle dogs, and Sprague-Dawley rats (FIGS. 3A-D). This effect has been observed in rats with both forms of RTA 402 (crystalline and amorphous).

RTA 402 reduces serum creatinine in patients. For example, improvements were observed in cancer patients receiving RTA 402. In humans, nephrotoxicity is a dose-limiting side-effect of treatment with cisplatin. Cisplatin-induced damage to the proximal tubules is thought to be mediated by increased inflammation, oxidative stress, and apoptosis (Yao et al., 2007). Serum creatinine has also been measured in patients with chronic kidney disease (CKD) enrolled in an open label Phase II clinical trial of RTA 402 (Example 6). This study was designed with multiple endpoints, in categories of insulin resistance, endothelial dysfunction/CVD, and CKD, including measurements of hemoglobin A1c (A1c), a widely used phase 3 endpoint for glycemic control.

A1c is a minor component of hemoglobin to which glucose is bound. A1c also is referred to as glycosylated or glucosylated hemoglobin. A1c may be separated by charge and size from the other hemoglobin A components in blood using high performance liquid chromatography (HPLC). Because A1c is not affected by short-term fluctuations in blood glucose concentrations, for example, due to meals, blood can be drawn for A1c testing without regard to when food was eaten. In healthy, non-diabetic patients the A1c level is less than 7% of total hemoglobin. The normal range is 4-5.9%. In poorly controlled diabetes, it can be 8.0% or above. It has been demonstrated that the complications of diabetes can be delayed or prevented if the A1c level can be kept close to 7%.

Recently approved agents typically only reduce A1c levels an amount of 0.4 to 0.80 over six months of treatment, with 28 day improvements typically smaller. The table below shows six-month Hemoglobin A1c Reductions by two approved agents, sitagliptin and pramlintide acetate (Aschner et al., 2006; Goldstein et al., 2007; Pullman et al., 2006).

| Drug | Duration of DM (years) | Study Design | Mean A1c | Change |
|---|---|---|---|---|
| Sitagliptin | 4.3 | +/−placebo with A1c ≧ 7.0 | 8.0 | −0.8 |
| | 4.4 | +/−metformin with A1c ≧ 7.5 | 8.9 | −0.7 |
| | 6.1 | pioglitazone +/− sitagliptin; A1c ≧ 7.0 | 8.1 | −0.7 |

-continued

| Drug | Duration of DM (years) | Study Design | Mean A1c | Change |
|---|---|---|---|---|
| Pramlintide acetate | 13 | +/−insulin | 9.1 | −0.4 |

In comparison, RTA 402 reduces A1c in 28 days in refractory diabetics on top of standard of care. The treatment showed an intent-to-treat reduction of 0.34 (n=21) and an elevated baseline (≧7.0 at baseline) reduction of 0.50 (n=16). These results are presented in greater detail in the Examples section below. See also FIGS. 6 and 7.

In another aspect, the compounds of this invention may also be used to improve insulin sensitivity and/or glycemic control. For example, hyperinsulinemic euglycemic clamp test results in the study detailed in Example 6 showed that treatment with RTA 402 improved glycemic control. The hyperinsulinemic euglycemic clamp test is a standard method for investigating and quantifying insulin sensitivity. It measures the amount of glucose necessary to compensate for an increased insulin level without causing hypoglycemia (DeFronzo et al., 1979).

The typical procedure is as follows: Through a peripheral vein, insulin is infused at 10-120 mU per $m^2$ per minute. In order to compensate for the insulin infusion, glucose 20% is infused to maintain blood sugar levels between 5 and 5.5 mmol/liter. The rate of glucose infusion is determined by checking the blood sugar levels every 5 to 10 minutes.

Typically, low-dose insulin infusions are more useful for assessing the response of the liver, whereas high-dose insulin infusions are useful for assessing peripheral (i.e., muscle and fat) insulin action.

Results are typically evaluated as follows: The rate of glucose infusion during the last 30 minutes of the test determines insulin sensitivity. If high levels (7.5 mg/min or higher) are required, the patient is insulin-sensitive. Very low levels (4.0 mg/min or lower) indicate that the body is resistant to insulin action. Levels between 4.0 and 7.5 mg/min may not be definitive and may suggest "impaired glucose tolerance," an early sign of insulin resistance.

Figure 9:
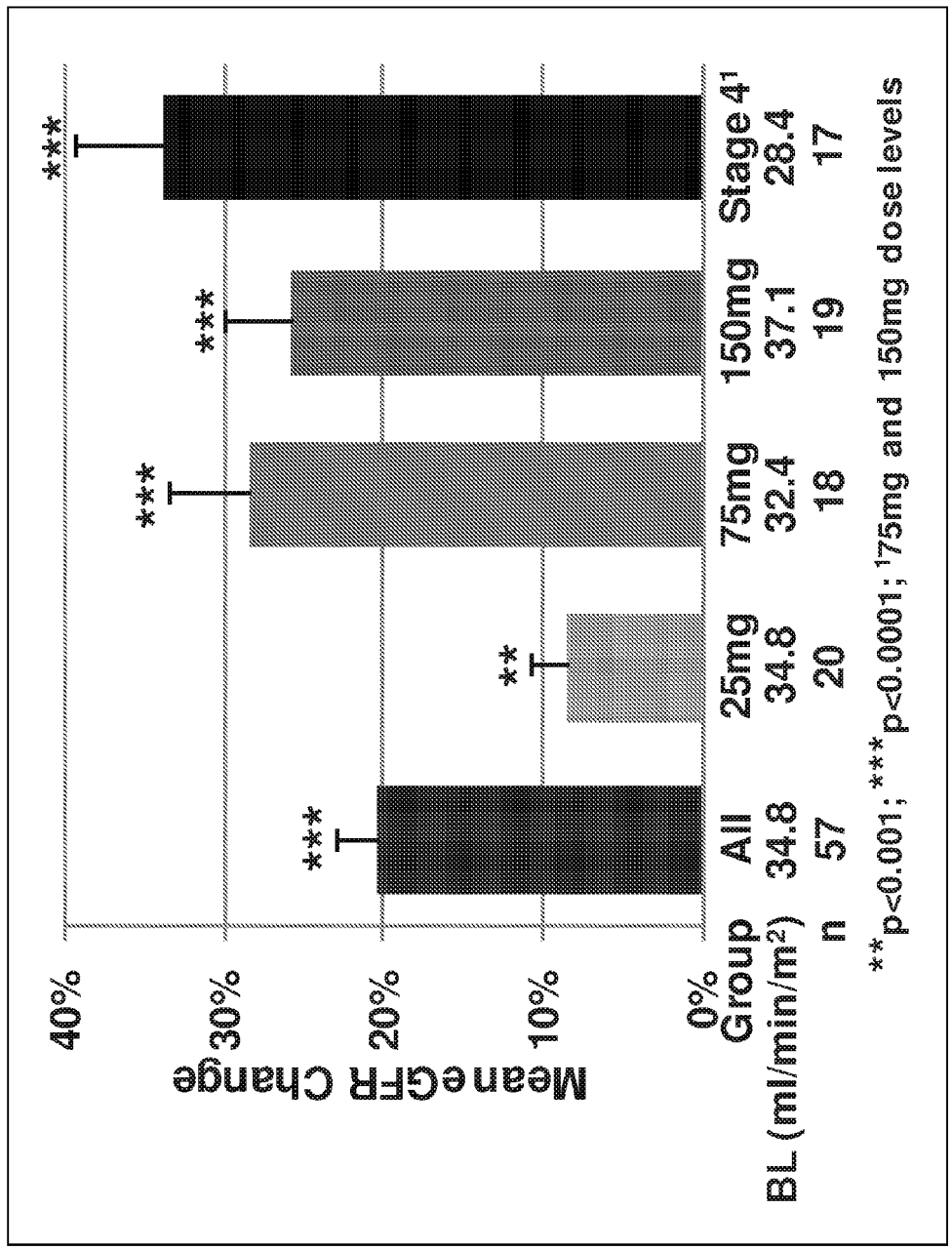
FIG. 9—Reversible Dose Dependent GFR Increase in 28 Days. Treatment with RTA 402 increases GFR dose-dependently. All evaluable patients were included. An improvement of >30% was noted in patients with Stage 4 renal disease.

The methods of this invention may be used to improve renal function. As shown in Example 6, treatment using RTA 402 has been shown to improve six measures of renal function and status, including serum creatinine based eGFR, creatinine clearance, BUN, Cystatin C, Adiponectin, and Angiotensin II. RTA 402 was shown to increase GFR in a dose-dependent manner and with high response rate (86%; n=22). As also shown in FIG. 9, the 28 day GFR improvements were reversible after the drug was withdrawn.

In some embodiments, treatment methods of this invention result in improved levels of Adiponectin and/or Angiotensin II. Adiponectin and Angiotensin II are typically elevated in DN patients and correlate with renal disease severity. Adiponectin (also referred to as Acrp30, apM1) is a hormone known to modulate a number of metabolic processes, including glucose regulation and fatty acid catabolism. Adiponectin is secreted from adipose tissue into the bloodstream and is abundant in plasma relative to many other hormones. Levels of the hormone are inversely correlated with body fat percentage in adults, while the association in infants and young children is more unclear. The hormone plays a role in the suppression of the metabolic derangements that may result in type 2 diabetes, obesity, atherosclerosis and non-alcoholic fatty liver disease (NAFLD). Adiponectin can be used to predict all-cause mortality and end stage renal disease in DN patients.

The compounds and methods of this invention may be used for treating various aspects of cardiovascular disease (CVD). The treatment methods of this invention have been found to reduce circulating endothelial cells (CECs) in human patients. CECs are markers of endothelial dysfunction and vascular injury. Endothelial dysfunction is a systemic inflammatory process that is linked to cardiovascular and end-organ damage. Elevated CECs typically correlate with the development, progression, and death from CVD. They also typically correlate with chronic kidney disease and decreased GFR. Historical normal levels are ≦5 cells/mL.

Typical features of endothelial dysfunction include the inability of arteries and arterioles to dilate fully in response to an appropriate stimulus. This creates a detectable difference in subjects with endothelial dysfunction versus a normal, healthy endothelium. Such a difference can be tested by a variety of methods including iontophoresis of acetylcholine, intra-arterial administration of various vasoactive agents, localised heating of the skin or temporary arterial occlusion by inflating a blood pressure cuff to high pressures. Testing can also take place in the coronary arteries themselves. These techniques are thought to stimulate the endothelium to release nitric oxide (NO) and possibly some other agents, which diffuse into the surrounding vascular smooth muscle causing vasodilation.

For example, according to the Phase II study results (Example 6), patients treated with RTA 402 for 28 days showed a reduction in cardiovascular inflammatory markers in the form of a reduction in the number of circulating endothelial cells. The reduction in CECs for the intent-to-treat group (n=20) was 27%; the reduction for the elevated baseline group (n=14) was 40% (p=0.02) and nine of those patients showed a normal level for CECs post-treatment. These results are consistent with a reversal of endothelial dysfunction.

The treatment methods of this invention have been found to reduce matrix metallopeptidase 9 (MMP-9), soluble adhesion molecules and tumor necrosis factor (TNFα) in most patients. High levels of these typically correlate with poor cardiovascular outcomes.

VI. Pharmaceutical Formulations and Routes of Administration

Administration of the compounds of the present invention to a patient will follow general protocols for the administration of pharmaceuticals, taking into account the toxicity, if any, of the drug. It is expected that the treatment cycles would be repeated as necessary.

The compounds of the present invention may be administered by a variety of methods, e.g., orally or by injection (e.g. subcutaneous, intravenous, intraperitoneal, etc.). Depending on the route of administration, the active compounds may be coated by a material to protect the compound from the action of acids and other natural conditions which may inactivate the compound. They may also be administered by continuous perfusion/infusion of a disease or wound site. Specific examples of formulations, including a polymer-based dispersion of CDDO-Me that showed improved oral bioavailability, are provided in U.S. application Ser. No. 12/191,176, filed Aug. 13, 2008, which is incorporated herein by reference in its entirety. It will be recognized by those skilled in the art that other methods of manufacture may be used to produce dispersions of the present invention with equivalent properties and utility (see Repka et al., 2002 and references cited therein). Such alternative methods include but are not limited to solvent evaporation, extrusion, such as hot melt extrusion, and other techniques.

To administer the therapeutic compound by other than parenteral administration, it may be necessary to coat the compound with, or co-administer the compound with, a material to prevent its inactivation. For example, the therapeutic compound may be administered to a patient in an appropriate carrier, for example, liposomes, or a diluent. Pharmaceutically acceptable diluents include saline and aqueous buffer solutions. Liposomes include water-in-oil-in-water CGF emulsions as well as conventional liposomes (Strejan et al., 1984).

The therapeutic compound may also be administered parenterally, intraperitoneally, intraspinally, or intracerebrally. Dispersions may be prepared in, e.g., glycerol, liquid polyethylene glycols, mixtures thereof, and in oils. Under ordinary conditions of storage and use, these preparations may contain a preservative to prevent the growth of microorganisms.

Pharmaceutical compositions suitable for injectable use include sterile aqueous solutions (where water soluble) or dispersions and sterile powders for the extemporaneous preparation of sterile injectable solutions or dispersion. In all cases, the composition must be sterile and must be fluid to the extent that easy syringability exists. It must be stable under the conditions of manufacture and storage and must be preserved against the contaminating action of microorganisms such as bacteria and fungi. The carrier may be a solvent or dispersion medium containing, for example, water, ethanol, polyol (such as, glycerol, propylene glycol, and liquid polyethylene glycol, and the like), suitable mixtures thereof, and vegetable oils. The proper fluidity can be maintained, for example, by the use of a coating such as lecithin, by the maintenance of the required particle size in the case of dispersion and by the use of surfactants. Prevention of the action of microorganisms can be achieved by various antibacterial and antifungal agents, for example, parabens, chlorobutanol, phenol, ascorbic acid, thimerosal, and the like. In many cases, it will be preferable to include isotonic agents, for example, sugars, sodium chloride, or polyalcohols such as mannitol and sorbitol, in the composition. Prolonged absorption of the injectable compositions can be brought about by including in the composition an agent which delays absorption, for example, aluminum monostearate or gelatin.

Sterile injectable solutions can be prepared by incorporating the therapeutic compound in the required amount in an appropriate solvent with one or a combination of ingredients enumerated above, as required, followed by filtered sterilization. Generally, dispersions are prepared by incorporating the therapeutic compound into a sterile carrier which contains a basic dispersion medium and the required other ingredients from those enumerated above. In the case of sterile powders for the preparation of sterile injectable solutions, the preferred methods of preparation are vacuum drying and freeze-drying which yields a powder of the active ingredient (i.e., the therapeutic compound) plus any additional desired ingredient from a previously sterile-filtered solution thereof.

The therapeutic compound can be orally administered, for example, with an inert diluent or an assimilable edible carrier. The therapeutic compound and other ingredients may also be enclosed in a hard or soft shell gelatin capsule, compressed into tablets, or incorporated directly into the subject's diet. For oral therapeutic administration, the therapeutic compound may be incorporated with excipients and used in the form of ingestible tablets, buccal tablets, troches, capsules, elixirs, suspensions, syrups, wafers, and the like. The percentage of the therapeutic compound in the compositions and preparations may, of course, be varied. The amount of the therapeutic compound in such therapeutically useful compositions is such that a suitable dosage will be obtained.

It is especially advantageous to formulate parenteral compositions in dosage unit form for ease of administration and uniformity of dosage. Dosage unit form as used herein refers to physically discrete units suited as unitary dosages for the subjects to be treated; each unit containing a predetermined quantity of therapeutic compound calculated to produce the desired therapeutic effect in association with the required pharmaceutical carrier. The specification for the dosage unit forms of the invention are dictated by and directly dependent on (a) the unique characteristics of the therapeutic compound and the particular therapeutic effect to be achieved, and (b) the limitations inherent in the art of compounding such a therapeutic compound for the treatment of a selected condition in a patient.

The therapeutic compound may also be administered topically to the skin, eye, or mucosa. Alternatively, if local delivery to the lungs is desired the therapeutic compound may be administered by inhalation in a dry-powder or aerosol formulation.

The actual dosage amount of a compound of the present invention or composition comprising a compound of the present invention administered to a subject may be determined by physical and physiological factors such as age, sex, body weight, severity of condition, the type of disease being treated, previous or concurrent therapeutic interventions, idiopathy of the subject and on the route of administration. These factors may be determined by a skilled artisan. The practitioner responsible for administration will typically determine the concentration of active ingredient(s) in a composition and appropriate dose(s) for the individual subject. The dosage may be adjusted by the individual physician in the event of any complication.

In some embodiments, the pharmaceutically effective amount is a daily dose from about 0.1 mg to about 500 mg of the compound. In some variations, the daily dose is from about 1 mg to about 300 mg of the compound. In some variations, the daily dose is from about 10 mg to about 200 mg of the compound. In some variations, the daily dose is about 25 mg of the compound. In other variations, the daily dose is about 75 mg of the compound. In still other variations, the daily dose is about 150 mg of the compound. In further variations, the daily dose is from about 0.1 mg to about 30 mg of the compound. In some variations, the daily dose is from about 0.5 mg to about 20 mg of the compound. In some variations, the daily dose is from about 1 mg to about 15 mg of the compound. In some variations, the daily dose is from about 1 mg to about 10 mg of the compound. In some variations, the daily dose is from about 1 mg to about 5 mg of the compound.

In some embodiments, the pharmaceutically effective amount is a daily dose is 0.01-25 mg of compound per kg of body weight. In some variations, the daily dose is 0.05-20 mg of compound per kg of body weight. In some variations, the daily dose is 0.1-10 mg of compound per kg of body weight. In some variations, the daily dose is 0.1-5 mg of compound per kg of body weight. In some variations, the daily dose is 0.1-2.5 mg of compound per kg of body weight.

In some embodiments, the pharmaceutically effective amount is a daily dose is of 0.1-1000 mg of compound per kg of body weight. In some variations, the daily dose is 0.15-20 mg of compound per kg of body weight. In some variations, the daily dose is 0.20-10 mg of compound per kg of body weight. In some variations, the daily dose is 0.40-3 mg of compound per kg of body weight. In some variations, the daily dose is 0.50-9 mg of compound per kg of body weight. In some variations, the daily dose is 0.60-8 mg of compound per kg of body weight. In some variations, the daily dose is 0.70-7 mg of compound per kg of body weight. In some variations, the daily dose is 0.80-6 mg of compound per kg of body weight. In some variations, the daily dose is 0.90-5 mg of compound per kg of body weight. In some variations, the daily dose is from about 1 mg to about 5 mg of compound per kg of body weight.

An effective amount typically will vary from about 0.001 mg/kg to about 1,000 mg/kg, from about 0.01 mg/kg to about 750 mg/kg, from about 0.1 mg/kg to about 500 mg/kg, from about 0.2 mg/kg to about 250 mg/kg, from about 0.3 mg/kg to about 150 mg/kg, from about 0.3 mg/kg to about 100 mg/kg, from about 0.4 mg/kg to about 75 mg/kg, from about 0.5 mg/kg to about 50 mg/kg, from about 0.6 mg/kg to about 30 mg/kg, from about 0.7 mg/kg to about 25 mg/kg, from about 0.8 mg/kg to about 15 mg/kg, from about 0.9 mg/kg to about 10 mg/kg, from about 1 mg/kg to about 5 mg/kg, from about 100 mg/kg to about 500 mg/kg, from about 1.0 mg/kg to about 250 mg/kg, or from about 10.0 mg/kg to about 150 mg/kg, in one or more dose administrations daily, for one or several days (depending, of course, of the mode of administration and the factors discussed above). Other suitable dose ranges include 1 mg to 10,000 mg per day, 100 mg to 10,000 mg per day, 500 mg to 10,000 mg per day, and 500 mg to 1,000 mg per day. In some particular embodiments, the amount is less than 10,000 mg per day with a range, for example, of 750 mg to 9,000 mg per day.

The effective amount may be less than 1 mg/kg/day, less than 500 mg/kg/day, less than 250 mg/kg/day, less than 100 mg/kg/day, less than 50 mg/kg/day, less than 25 mg/kg/day, less than 10 mg/kg/day, or less than 5 mg/kg/day. It may alternatively be in the range of 1 mg/kg/day to 200 mg/kg/day. For example, regarding treatment of diabetic patients, the unit dosage may be an amount that reduces blood glucose by at least 40% as compared to an untreated subject. In another embodiment, the unit dosage is an amount that reduces blood glucose to a level that is within ±10% of the blood glucose level of a non-diabetic subject.

In other non-limiting examples, a dose may also comprise from about 1 micro-gram/kg/body weight, about 5 microgram/kg/body weight, about 10 microgram/kg/body weight, about 50 microgram/kg/body weight, about 100 microgram/kg/body weight, about 200 microgram/kg/body weight, about 350 microgram/kg/body weight, about 500 microgram/kg/body weight, about 1 milligram/kg/body weight, about 5 milli-gram/kg/body weight, about 10 milligram/kg/body weight, about 50 milligram/kg/body weight, about 100 milligram/kg/body weight, about 200 milligram/kg/body weight, about 350 milligram/kg/body weight, about 500 milligram/kg/body weight, to about 1000 mg/kg/body weight or more per administration, and any range derivable therein. In non-limiting examples of a derivable range from the numbers listed herein, a range of about 1 mg/kg/body weight to about 5 mg/kg/body weight, a range of about 5 mg/kg/body weight to about 100 mg/kg/body weight, about 5 microgram/kg/body weight to about 500 milligram/kg/body weight, etc., can be administered, based on the numbers described above.

In certain embodiments, a pharmaceutical composition of the present invention may comprise, for example, at least about 0.1% of a compound of the present invention. In other embodiments, the compound of the present invention may comprise between about 2% to about 75% of the weight of the unit, or between about 25% to about 60%, for example, and any range derivable therein.

Single or multiple doses of the agents are contemplated. Desired time intervals for delivery of multiple doses can be determined by one of ordinary skill in the art employing no more than routine experimentation. As an example, subjects may be administered two doses daily at approximately 12 hour intervals. In some embodiments, the agent is administered once a day.

The agent(s) may be administered on a routine schedule. As used herein a routine schedule refers to a predetermined designated period of time. The routine schedule may encompass periods of time which are identical or which differ in length, as long as the schedule is predetermined. For instance, the routine schedule may involve administration twice a day, every day, every two days, every three days, every four days, every five days, every six days, a weekly basis, a monthly basis or any set number of days or weeks there-between. Alternatively, the predetermined routine schedule may involve administration on a twice daily basis for the first week, followed by a daily basis for several months, etc. In other embodiments, the invention provides that the agent(s) may taken orally and that the timing of which is or is not dependent upon food intake. Thus, for example, the agent can be taken every morning and/or every evening, regardless of when the subject has eaten or will eat.

Non-limiting specific formulations include CDDO-Me polymer dispersions (see U.S. application Ser. No. 12/191, 176, filed Aug. 13, 2008, which is incorporated herein by reference). Some of the formulations reported therein exhibited higher bioavailability than either the micronized Form A or nanocrystalline Form A formulations. Additionally, the polymer dispersion based formulations demonstrated further surprising improvements in oral bioavailability relative to the micronized Form B formulations. For example, the methacrylic acid copolymer, Type C and HPMC-P formulations showed the greatest bioavailability in the subject monkeys.

VII. Combination Therapy

In addition to being used as a monotherapy, the compounds of the present invention may also find use in combination therapies. Effective combination therapy may be achieved with a single composition or pharmacological formulation that includes both agents, or with two distinct compositions or formulations, administered at the same time, wherein one composition includes a compound of this invention, and the other includes the second agent(s). Alternatively, the therapy may precede or follow the other agent treatment by intervals ranging from minutes to months.

Various combinations may be employed, such as when a compound of the present invention is "A" and "B" represents a secondary agent, non-limiting examples of which are described below:

| A/B/A | B/A/B | B/B/A | A/A/B | A/B/B | B/A/A | A/B/B/B | B/A/B/B |
|-------|-------|-------|-------|-------|-------|---------|---------|
| B/B/B/A | B/B/A/B | A/A/B/B | A/B/A/B | A/B/B/A | B/B/A/A | | |
| B/A/B/A | B/A/A/B | A/A/A/B | B/A/A/A | A/B/A/A | A/A/B/A | | |

It is contemplated that other anti-inflammatory agents may be used in conjunction with the treatments of the current invention. For example, other COX inhibitors may be used, including arylcarboxylic acids (salicylic acid, acetylsalicylic acid, diflunisal, choline magnesium trisalicylate, salicylate, benorylate, flufenamic acid, mefenamic acid, meclofenamic acid and triflumic acid), arylalkanoic acids (diclofenac, fenclofenac, alclofenac, fentiazac, ibuprofen, flurbiprofen, ketoprofen, naproxen, fenoprofen, fenbufen, suprofen, indoprofen, tiaprofenic acid, benoxaprofen, pirprofen, tolmetin, zomepirac, clopinac, indomethacin and sulindac) and enolic acids (phenylbutazone, oxyphenbutazone, azapropazone, feprazone, piroxicam, and isoxicam. See also U.S. Pat. No. 6,025,395, which is incorporated herein by reference.

Dietary and nutritional supplements with reported benefits for treatment or prevention of Parkinson's, Alzheimer's, multiple sclerosis, amyotrophic lateral sclerosis, rheumatoid arthritis, inflammatory bowel disease, and all other diseases whose pathogenesis is believed to involve excessive production of either nitric oxide (NO) or prostaglandins, such as acetyl-L-carnitine, octacosanol, evening primrose oil, vitamin B6, tyrosine, phenylalanine, vitamin C, L-dopa, or a combination of several antioxidants may be used in conjunction with the compounds of the current invention.

Other particular secondary therapies include immunosuppressants (for transplants and autoimmune-related RKD), anti-hypertensive drugs (for high blood pressure-related RKD, e.g., angiotensin-converting enzyme inhibitors and angiotensin receptor blockers), insulin (for diabetic RKD), lipid/cholesterol-lowering agents (e.g., HMG-CoA reductase inhibitors such as atorvastatin or simvastatin), treatments for hyperphosphatemia or hyperparathyroidism associated with CKD (e.g., sevelamer acetate, cinacalcet), dialysis, and dietary restrictions (e.g., protein, salt, fluid, postassium, phosphorus).

VIII. EXAMPLES

The following examples are included to demonstrate preferred embodiments of the invention. It should be appreciated by those of skill in the art that the techniques disclosed in the examples which follow represent techniques discovered by the inventor to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

Example 1

Materials and Methods

Chemicals. Triterpenoids were synthesized as previously described in Honda et al. (1998), Honda et al. (2000b), Honda et al. (2002) and Yates et al. (2007), which are all incorporated herein by reference.

Example 2

Mouse Ischemia-Reperfusion Results

In a mouse model of ischemic acute renal failure, the renal artery is clamped for approximately twenty minutes. After this time, the clamp is removed and the kidney is reperfused with blood. Ischemia-reperfusion results in renal damage and decreased renal function which can be assessed by blood urea nitrogen (BUN) levels, which become elevated following renal damage. As shown in FIGS. 1a-d, surgically-induced ischemia-reperfusion increased BUN levels by approximately 2-fold. However, in animals treated with 2 mg/kg RTA 402 orally once daily beginning two days prior to the surgery, the BUN levels were significantly reduced (p<0.01) relative to vehicle-treated animals and were similar to the levels in animals that underwent sham surgeries (FIGS. 1a-c). Histological measures of kidney damage and inflammation were also significantly improved by treatment with RTA 402 (FIG. 1d). These data indicate that RTA 402 is protective against ischemia-reperfusion induced tissue damage.

Example 3

Rat Chemotherapy-Induced Acute Renal Injury Results

Figure 2:
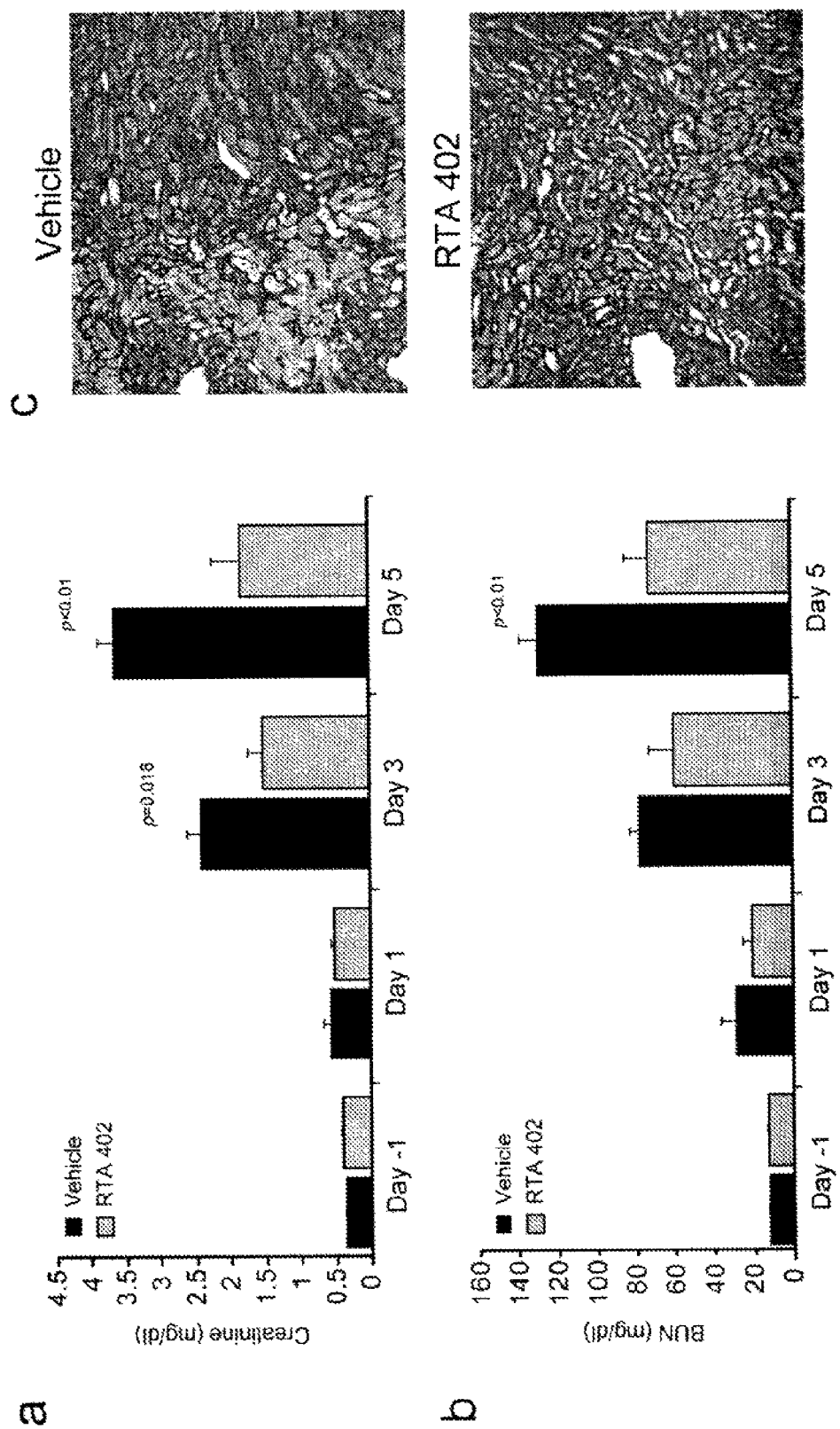
FIGS. 2a-c—RTA 402 reduces cisplatin-induced renal toxicity. Rats were administered RTA 402 at 10 mg/kg or simply the vehicle (sesame oil) every day by oral gavage beginning on Day −1. On Day 0, the rats received an intravenous injection of cisplatin at 6 mg/kg. Blood samples were drawn on the indicated days and the levels of creatinine (FIG. 2a) and blood urea nitrogen (BUN) (FIG. 2b) were measured as markers of renal damage. A statistically significant difference was observed between the vehicle-treated and RTA 402-treated groups on Day 3 (creatinine) and Day 5 (creatinine and BUN).
Figure 3:
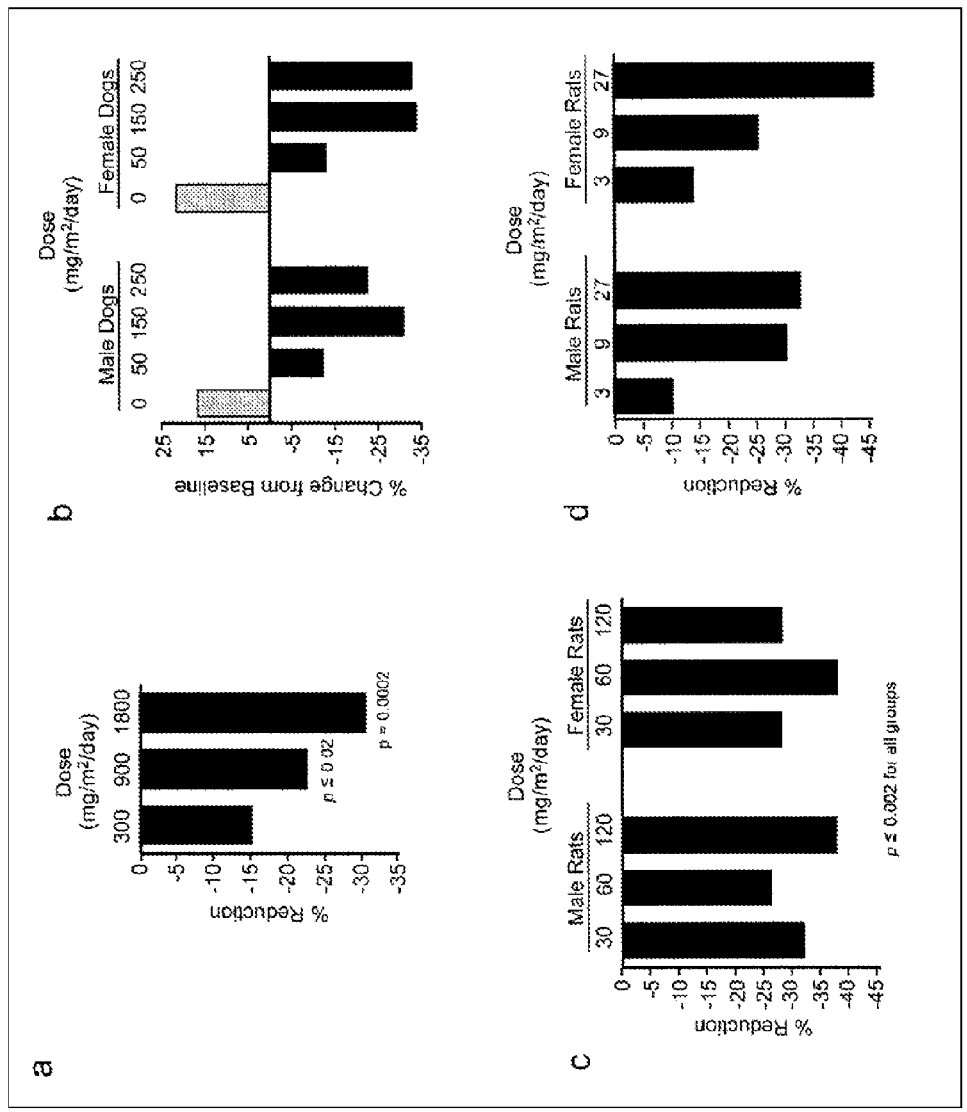
FIGS. 3a-d—RTA 402 reduces serum creatinine levels in monkeys, dogs, and rats.

In another model of acute renal injury, rats were injected intravenously with the antineoplastic agent cisplatin. In humans, nephrotoxicity is a dose-limiting side effect of treatment with cisplatin. Cisplatin-induced damage to the proximal tubules is thought to be mediated by increased inflammation, oxidative stress, and apoptosis (Yao et al., 2007). Rats treated with a single dose of cisplatin at 6 mg/kg developed renal insufficiency as measured by increased blood levels of creatinine and BUN. Treatment with 10 mg/kg RTA 402 by oral gavage beginning one day prior to treatment with cisplatin and continuing every day significantly reduced blood levels of creatinine and BUN (FIGS. 2a-b). Histological evaluation of the kidneys demonstrated an improvement in the extent of proximal tubule damage in RTA 402-treated animals compared to vehicle-treated animals (FIG. 2c).

Example 4

Reduction of Serum Creatinine Levels in Several Species

Serum creatinine has been measured in several animal species treated with RTA 402 in the course of toxicology studies. Significant reductions of serum creatinine levels relative to baseline levels or levels in control animals have been observed in cynomolgus monkeys, beagle dogs, and Sprague-Dawley rats (FIGS. 3a-d). This effect has been observed in rats with crystalline and amorphous forms of RTA 402.

Example 5

Reduced Serum Creatinine and Increased eGFR in Cancer Patients

Figure 4:
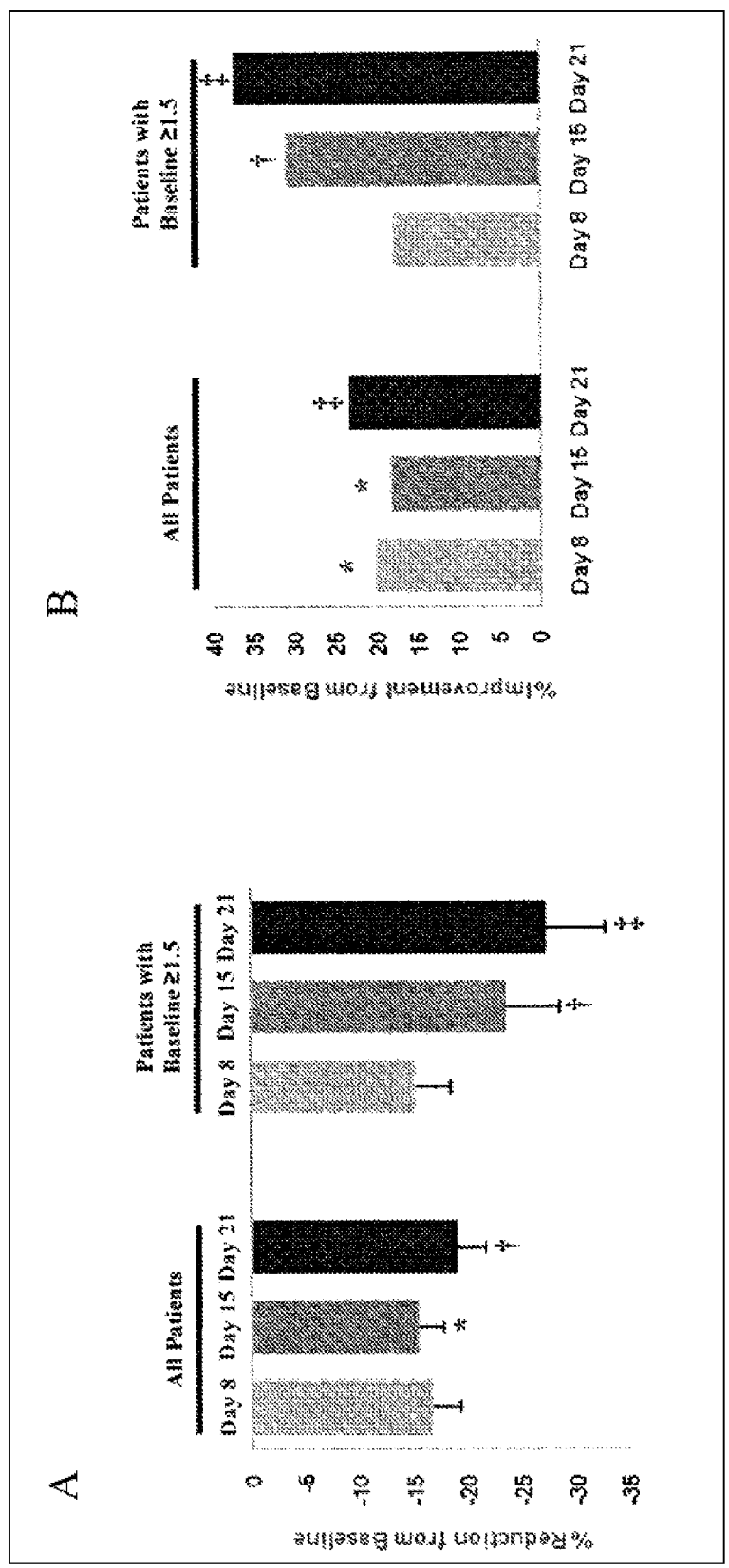
FIGS. 4A-B—RTA 402 reduces serum creatinine levels and increases the estimated glomerular filtration rate (eGFR) in human patients with cancer.

Serum creatinine has also been measured in patients with cancer enrolled in a Phase I clinical trial of RTA 402. These patients received RTA 402 once daily at doses from 5 to 1,300 mg/day for a total of twenty-one days every 28 days. A reduction in serum creatinine by greater than 15% was observed as early as eight days following treatment initiation and persisted through the end of the cycle (FIG. 4A). This reduction was maintained in those patients that received six or more cycles of treatment with RTA 402. A subset of patients with pre-existing renal damage (baseline serum creatinine levels of at least 1.5 mg/dl) also had significant reductions in serum creatinine levels following treatment with RTA 402. In these patients, serum creatinine levels decreased progressively throughout the cycle such that the Day 21 levels were approximately 25% lower than baseline levels (FIG. 4A). These results can be summarized as shown in the table below.

|  | All patients | Sub-set with elevated baseline serum creatinine levels |
| --- | --- | --- |
| Number of patients who received drug for at least 3 weeks | 45 | 8 |
| % of Patients with Decrease on Day 21 | 87% | 100% |
| % Serum Creatinine Decrease from Baseline | −18.3% | −24.5% |
| p-value (Baseline versus Day 21) | 0.001 | 0.0007 |

The estimated glomerular filtration rate (eGFR) significantly improved in the patients treated with RTA 402 (FIG. 4B).

Figure 5:
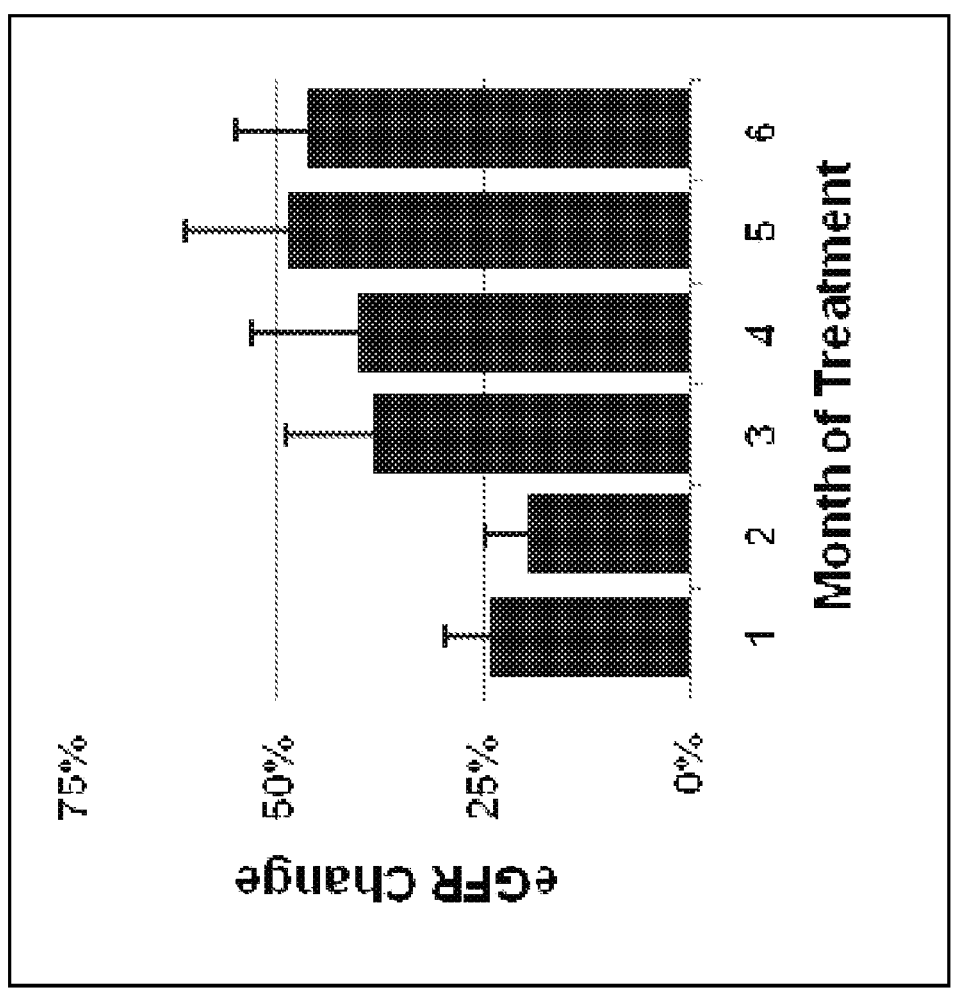
FIG. 5—RTA 402 increases GFR in human patients with cancer. Estimated glomerular filtration rate (eGFR) was measured in RTA 402-treated patients enrolled in a multi-month clinical trial for the treatment of cancer. All patients (n=11) dosed through six months were included in the analysis. The dosing information for these patients is provided in Example 5, below.

FIG. 5 shows the results following at least six months of RTA 402 treatment in eleven cancer patients, showing that eGFR improved in an approximately continuous manner. Some of these patients were enrolled in the Phase I study, whereas others were enrolled in a study of RTA 402 (in combination with gemcitabine) in patients with pancreatic cancer. The results can be summarized as shown in Table 2, below.

TABLE 2 eGFR in Patients Receiving RTA 402 for 6 Cycles.

|  |  | Solid Tumor Study | | | | | | Pancreatic Study | | | |
| --- | --- | --- | --- | --- | --- | --- | --- | --- | --- | --- | --- |
|  |  | Pt ID: | | | | | | | | | |
|  |  | 402 | 406 | 408 | 409 | 410 | 421 | 427 | 1001 | 1104 | 1105 | 1106 |
|  |  | Dose (mg): | | | | | | | | | |
|  |  | 5 | 80 | 150 | 150/300 | 300/600 | 1300/900 | 1300 | 150 | 300/150 | 300 | 300 |
| Cycle | BL | 109.7 | 94.2 | 73.2 | 48.4 | 49.9 | 52.5 | 70.1 | 68.8 | 67.3 | 82.4 | 89.0 |
| (each cycle | 1 | 109.7 | 125.9 | 82.1 | 62.6 | 69.6 | 58.6 | 101.3 | 78.9 | 95.7 | 106.6 | 106.3 |
| is 28 days) | 2 | 109.7 | 107.9 | 77.4 | 62.6 | 63.4 | 66.2 | 78.3 | 109.9 | 71.6 | 89.3 | 106.3 |
|  | 3 | 95.7 | 107.9 | 69.4 | 62.6 | 63.4 | 75.8 | 88.4 | 135.7 | 141.2 | 106.6 | 106.3 |
|  | 4 | 95.7 | 125.9 | 77.4 | 57.0 | 69.6 | N/A | 101.3 | 175.5 | 95.7 | 106.6 | 131.2 |
|  | 5 | 109.7 | 107.9 | 77.4 | 69.2 | 63.4 | 88.4 | 101.3 | 175.5 | 114.4 | 131.6 | 131.2 |
|  | 6 | 95.7 | 125.9 | 87.4 | 69.2 | 69.6 | 75.8 | 101.3 | 135.7 | 114.4 | 170.3 | 131.2 |

Example 6

Phase 2 Study in Patients with Diabetic Nephropathy

Serum creatinine has also been measured in patients with chronic kidney disease (CKD) enrolled in an open label Phase II clinical trial of RTA 402. These patients received RTA 402 once daily at three dose levels, 25 mg, 75 mg and 150 mg, for a total of 28 days.

The study was designed with multiple endpoints, in categories of insulin resistance, endothelial dysfunction/CVD, and CKD. These can be summarized as follows:

| Insulin Resistance/Diabetes | Endothelial Dysfunction/ Cardiovascular | Chronic Kidney Disease |
| --- | --- | --- |
| Hgb A1c | CECs | GFR |
| GDR/Euglycemic Clamp | C-Reactive Protein (CRP) | Serum Creatinine |
| Glucose | E-Selectin | Creatinine Clearance |
|  | VCAM | Cystatin C |
|  | Cytokines | Adiponectin |
|  |  | Angiotensin II |

A primary outcome measure for this study is determining the effects of RTA 402 administered orally at the three dose strengths on the glomerular filtration rate (as estimated by the MDRD formula) in patients with diabetic nephropathy.

Secondary outcome measures include: (1) an evaluation of the safety and tolerability of oral RTA 402 administered orally at the three different doses, in this patient population; (2) an evaluation of the effects of RTA 402 administered orally at the three dose strengths on the serum creatinine level, creatinine clearance, and urine albumin/creatinine ratio in patients with diabetic nephropathy; (3) an evaluation of the effects of RTA 402 administered orally at the three dose strengths on hemoglobin A1c in all patients enrolled and on insulin response by the hyperinsulinemic euglycemic clamp test in patients enrolled at only one of the study centers; (4) an evaluation of the effects of RTA 402 at the three different doses on a panel of markers of inflammation, renal injury, oxidative stress, and endothelial cell dysfunction.

The patient population selected for this study all had type 2 diabetes with CKD. Most had been diagnosed with poor glycemic control for two decades. CKD was established through elevated serum creatinine (SCr) levels. Most of the patients had been diagnosed with cardiovascular disease (CVD) and most were receiving standard of care (SOC) treatment for diabetes, CKD and CVD, (e.g., insulin, ACEI/ARB, β-blocker, diuretic, and statin). The baseline demographic can be summarized as follows:

| Age | 59 |
| --- | --- |
| Diabetes Duration (yrs) | 15.4 |
| Diabetic Nephropathy | 100% |
| Non-renal Diabetic Complications[1] | 100% |
| Hypertensive | 100% |
| Hgb A1c(%) | 7.9% |
| Failed Oral Antihyperglycemics | 90% |
| ACEI/ARB Use | 80% |
| Statin Use | 50% |

[1] Includes neuropathy and retinopathy
All values represent the mean;
n = 10;
1st 10 patients to complete study The patient inclusion criteria were as follows: (1) diagnosis of type 2 diabetes; (2) serum creatinine in women 1.3-3.0 mg/dL (115-265 μmol/L), inclusive, and in men 1.5-3.0 mg/dL (133-265 μmol/L), inclusive; (3) patient must agree to practice effective contraception; (4) patient must have a negative urine pregnancy test within 72 hours prior to the first dose of study medication; (5) patient is willing and able to cooperate with all aspects of the protocol and is able to communicate effectively; (6) patient is willing and able to provide written informed consent to participate in this clinical study.

The patient exclusion criteria were the following: (1) patients having type 1 (insulin-dependent; juvenile onset) diabetes; (2) patients with known non-diabetic renal disease (nephrosclerosis superimposed on diabetic nephropathy acceptable), or with renal allograft; (3) patients having cardiovascular disease as follows: unstable angina pectoris within 3 months of study entry; myocardial infarction, coronary artery bypass graft surgery, or percutaneous transluminal coronary angioplasty/stent within 3 months of study entry; transient ischemic attack within 3 months of study entry; cerebrovascular accident within 3 months of study entry; obstructive valvular heart disease or hypertrophic cardiomyopathy; second or third degree atrioventricular block not successfully treated with a pacemaker; (4) patients with need for chronic (>2 weeks) immunosuppressive therapy, including corticosteroids (excluding inhaled or nasal steroids) within 3 months of study entry; (5) patients with evidence of hepatic dysfunction including total bilirubin>1.5 mg/dL (>26 micromole/L) or liver transaminase (aspartate aminotransferase [AST] or alanine transferase [ALT])>1.5 times upper limit of normal; (6) if female, patient is pregnant, nursing or planning a pregnancy; (7) patients with any concurrent clinical conditions that in the judgment of the investigator could either potentially pose a health risk to the patient while involved in the study or could potentially influence the study outcome; (8) patients having known hypersensitivity to any component of the study drug; (9) patients having known allergy to iodine; (10) patients having undergone diagnostic or intervention procedure requiring a contrast agent within the last 30 days prior to entry into the study; (11) patients with change or dose-adjustment in any of the following medications: ACE inhibitors, angiotensin II blockers, non-steroidal anti inflammatory drugs (NSAIDs), or COX-2 inhibitors within 3 months; other anti-hypertensive, and other anti-diabetic medications within 6 weeks prior to entry into the study; (12) patients having a history of drug or alcohol abuse or having positive test results for any drug of abuse (positive urine drug test and/or alcohol breathalyzer test); (13) patients having participated in another clinical study involving investigational or marketed products within 30 days prior to entry into the study or would concomitantly participate in such a study; (14) patients unable to communicate or cooperate with the Investigator due to language problems, poor mental development or impaired cerebral function.

As of the end of September 2008, there were 32 of 60 patients enrolled in this study. All but one patient was receiving insulin and standard-of-care oral antihyperglycemics.

Figure 6:
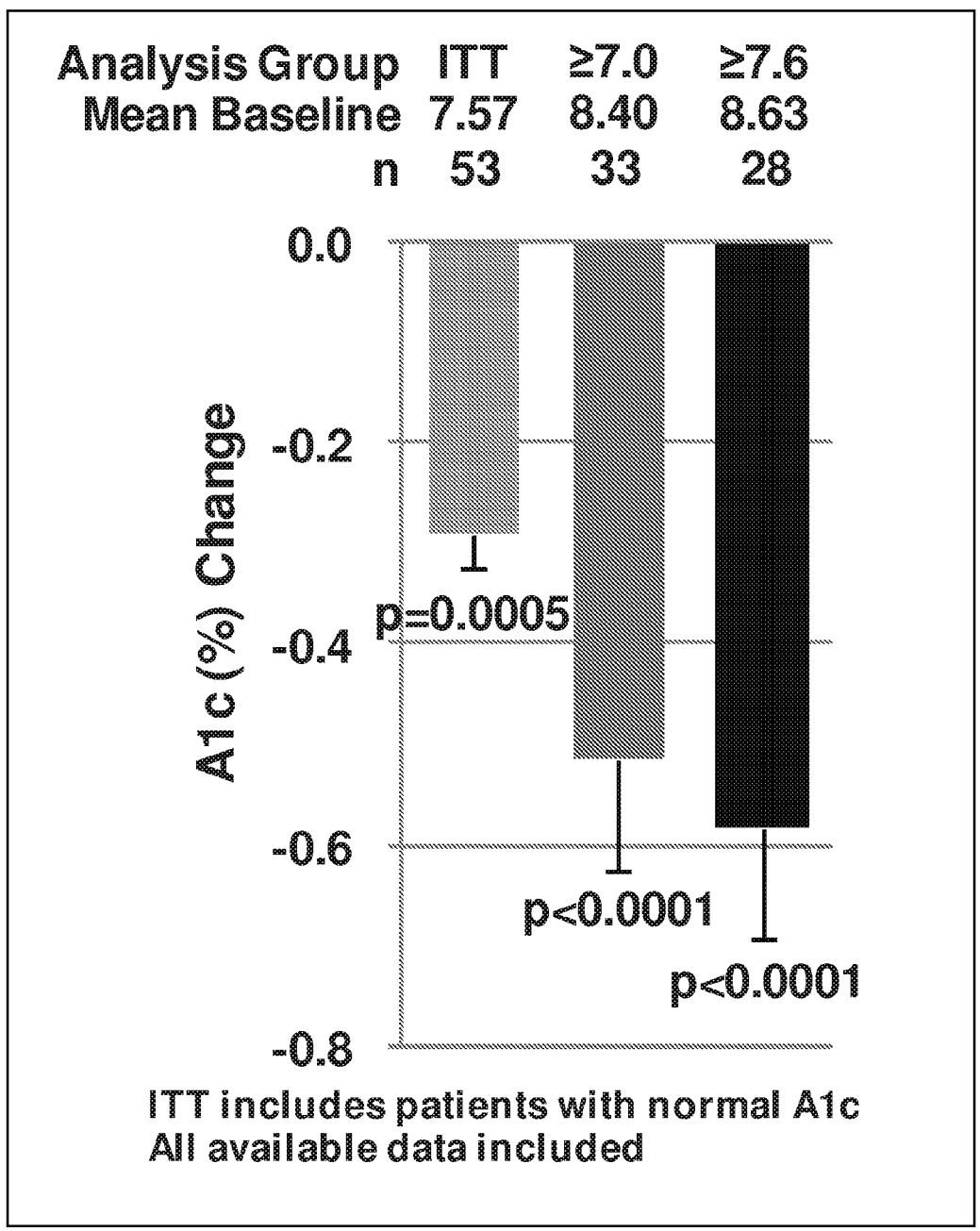
FIG. 6—RTA 402 Activity Correlates with Severity. Reduction of hemoglobin A1c is presented as a fraction of the initial baseline value. Groups with higher baselines, e.g., mean baseline≧7.0% A1c or ≧7.6% A1c, showed greater reduction. The intent-to-treat (ITT) group includes all patients (n=53), including those starting at a normal A1c value.
Figure 7:
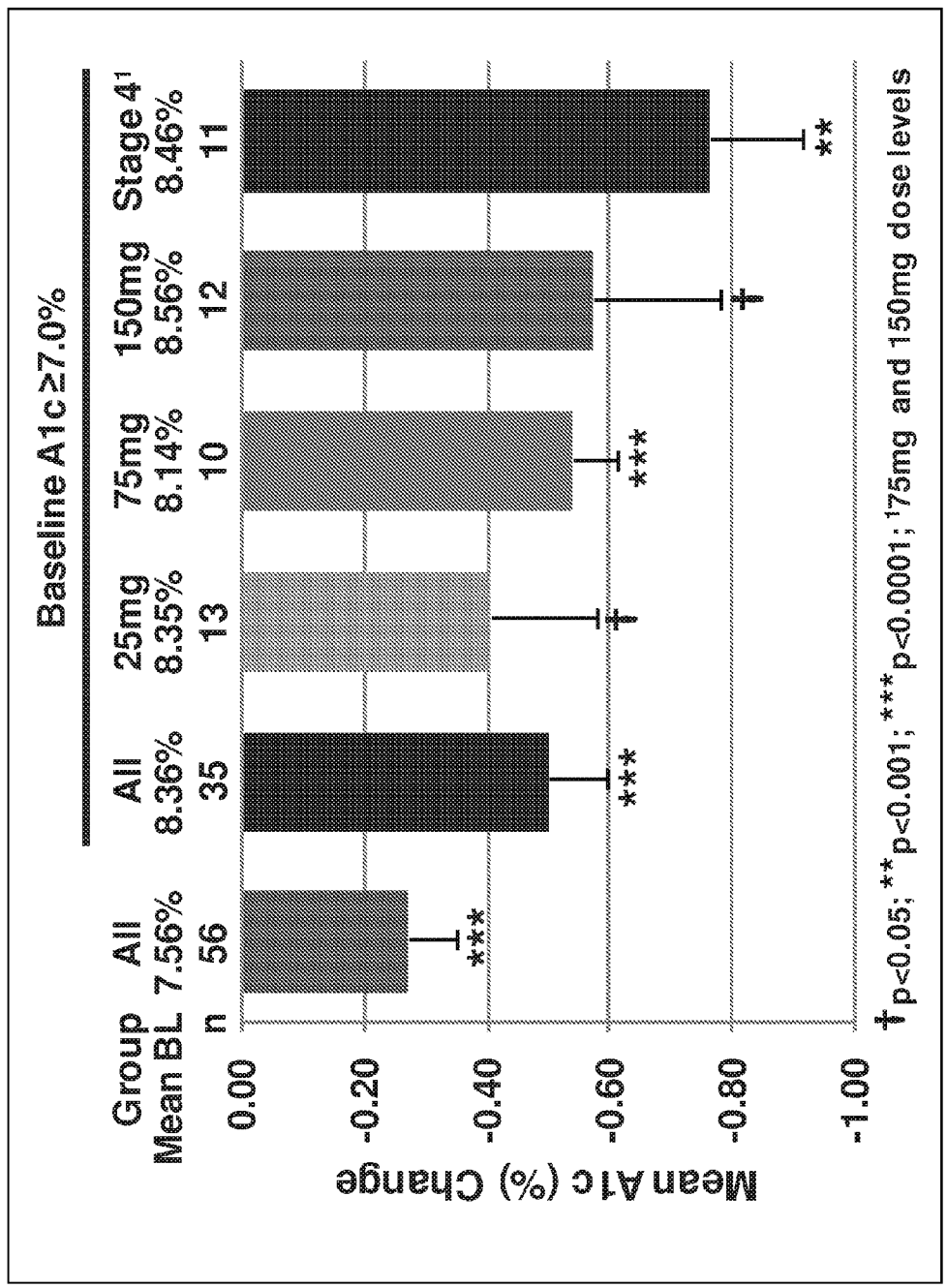
FIG. 7—RTA 402 Activity is Dose Dependent. Reduction of hemoglobin A1c is presented relative to the initial baseline value. The bar graph shows mean results for all patients, all patients with baseline A1c values≧7.0%, individual dose cohorts from the ≧7.0% group, and patients with Stage 4 renal disease (GFR 15-29 mL/min), wherein n is the number of patients in each group.

Treatment with RTA 402 was observed to reduce hemoglobin % A1c in 28 days in refractory diabetics on top of standard of care. The treatment showed an intent-to-treat reduction of approximately 0.25 (n=56) and an elevated baseline (≧7.0 at baseline) reduction of 0.50 (n=35). Hemoglobin % A1c reduction as a function of baseline severity is shown in FIG. 6, and reduction as a function of dosage is shown in FIG. 7. Patients with advanced (Stage 4) renal disease (GFR from 15-29 ml/min) showed a mean % A1c reduction of approximately 0.77. All reductions were statistically significant.

Hyperinsulinemic euglycemic clamp test results showed that the 28 day treatment also improved glycemic control and insulin sensitivity in the patients, as measured by glucose disposal rate (GDR). Patients exhibited improvements in GDR after the 28 day treatment, with more severely impaired patients (GDR<4) showing statistically significant improvements (p≦0.02). The hyperinsulinemic euglycemic clamp test was performed at Baseline (Day −1) and at the end of the study on Day 28. The test measures the rate of glucose infusion (GINF) necessary to compensate for an increased insulin level without causing hypoglycemia; this value is used to derive the GDR.

In short, the hyperinsulinemic euglycemic clamp test takes about 2 hours. Through a peripheral vein, insulin is infused at 10-120 mU per $m^2$ per minute. In order to compensate for the insulin infusion, glucose 20% is infused to maintain blood sugar levels between 5 and 5.5 mmol/L. The rate of glucose infusion is determined by checking the blood sugar levels every 5 to 10 minutes. The rate of glucose infusion during the last 30 minutes of the test is used to determine insulin sensitivity as determined by the glucose metabolism rate (M) in mg/kg/min.

The following protocol guidelines are in place for the hyperinsulinemic euglycemic clamp test:
1) Subject to fast 8-10 hours prior to the clamp procedure.
2) The morning of the clamp measure vital signs and weight.
3) Start a retrograde line in one hand with 1¼", 18-20 gauge catheter for drawing samples.
4) Prepare IV tubing with 2 three-way stop cocks and j-loop extension tubing. Spike tubing to a liter bag of 0.9% NaCl to run at KVO (keep vein open, about 10 cc/hr) until the start of the procedure.
5) Apply a heating pad covered in a pillow case with a pad separating the heating pad from the subject's hand. (Enables the collection of shunted arterialized blood from venous catheterization)
6) Monitor the temperature (approximately 150° F./65° C.) generated by the heating pad before and during the clamp, to maintain arterialization.
7) Start another line opposite the draw side in the distal forearm with 1¼", 18-20 gauge catheter for the infusion line. Prepare IV tubing with 2 three-way stop cocks.
8) Hang a 500 ml bag of 20% dextrose and attach to port on the infusion side
9) Prepare the insulin infusion
   a. Remove 53 cc (50 cc of overfill) of saline from a 500 cc bag of 0.9% NaCl and discard
   b. Draw 8 cc of blood from subject using sterile technique and inject into a tiger top tube
   c. Centrifuge the tiger top tube. Withdraw 2 cc of serum and inject into the 500 cc bag of 0.9% NaCl
   d. Add 100 units of insulin to the bag with the serum and mix well (0.2 U insulin/ml)
   e. Connect IV tubing with duo-vent spike into the 0.9% NaCl bag
   f. Place on Baxter pump
10) Time and draw all basal blood samples (Baseline fasting blood glucose values will be obtained prior to beginning the insulin prime).
11) Perform insulin infusion rate calculations for a priming dose and 60 mU/$m^2$ insulin infusion. This background insulin is to suppress endogenous hepatic glucose production. Lean subjects can be suppressed with 40 mU/m 2; obese, insulin resistant subjects require 80 mU/$m^2$. 60 mU/$m^2$ should be sufficient to suppress the suggested study population with a BMI of 27-40 kg/$m^2$. The suggested 60 mU/$m^2$ insulin infusion may need to be adjusted if the BMI is amended.
12) 0.5 mL samples will be drawn every five minutes and the readings from the YSI Blood Glucose Analyzer will be used to determine/adjust the glucose infusion rate (mg/kg/min). Any additional laboratory tests required by the protocol will be in addition to the blood volume.

The clamp will last 120 minutes which is believed to be a sufficient duration for determining insulin sensitivity.

13) Label and save all YSI printouts for source documents.

14) The glucose infusion rates from the last 30 minutes of the euglycemic clamp will be adjusted using space correction. This will be used to determine the glucose metabolism rate (M mg/kg/min), which represents the subject's sensitivity to insulin.

Figure 8:
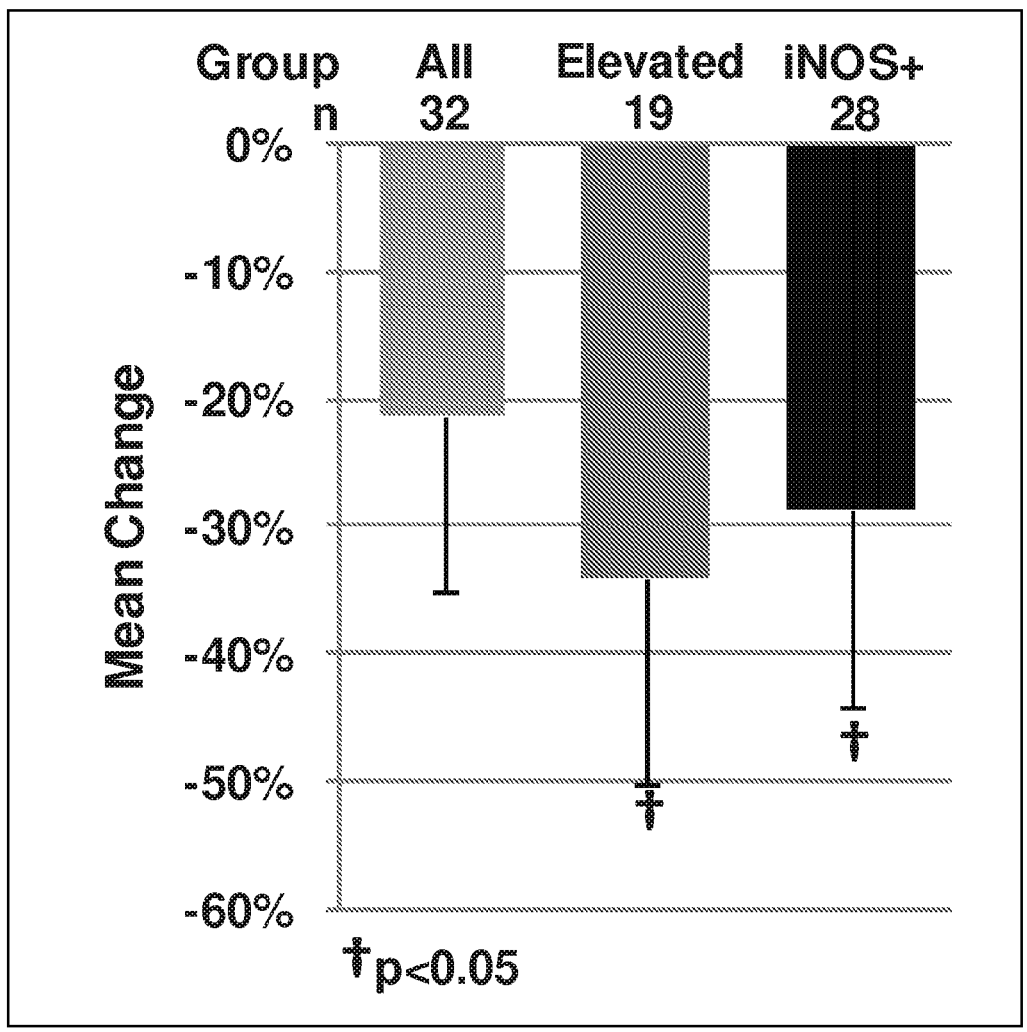
FIG. 8—RTA 402 Reduces Circulating Endothelial Cells (CECs) and iNOS-positive CECs. The change in the mean number of CECs in cells/mL is shown for intent-to-treat (ITT) and elevated baseline groups, both before and after the 28 day RTA treatment. The reduction for the Intent-to-treat group was approximately 20%, and the reduction in the elevated baseline group (>5 CECs/ml) was approximately 33%. The fraction of iNOS-positive CECs was reduced approximately 29%.

As shown in FIG. 8, RTA 402 reduces circulating endothelial cells (CECs). The mean number of CECs in cells/mL is shown for intent-to-treat (ITT) and elevated baseline groups, both before and after the 28 day RTA treatment. The reduction for the Intent-to-treat group was approximately 20%, and the reduction in the elevated baseline group (>5 CECs/ml) was approximately 33%. The fraction of iNOS-positive CECs was reduced approximately 29%. Normalization of CEC values ($\leq$5 cells/mL) was observed in 11 out of the 19 patients with elevated baseline.

CECs were isolated from whole blood by using CD146 Ab (an antibody to the CD146 antigen that is expressed on endothelial cells and leukocytes). After CEC isolation, a FITC (fluorescein isothiocyanate) conjugated CD105 Ab (a specific antibody for endothelial cells) is used to identify CECs using the CellSearch™ system. A fluorescent conjugate of CD45 Ab was added to stain the leukocytes, and these were then gated out. For a general overview of this method, see Blann et al., (2005), which is incorporated herein by reference in its entirety. CEC samples were also assessed for the presence of iNOS by immunostaining. Treatment with RTA 402 reduced iNOS-positive CECs by approximately 29%, further indicating that RTA 402 reduces inflammation in endothelial cells.

Figure 10:
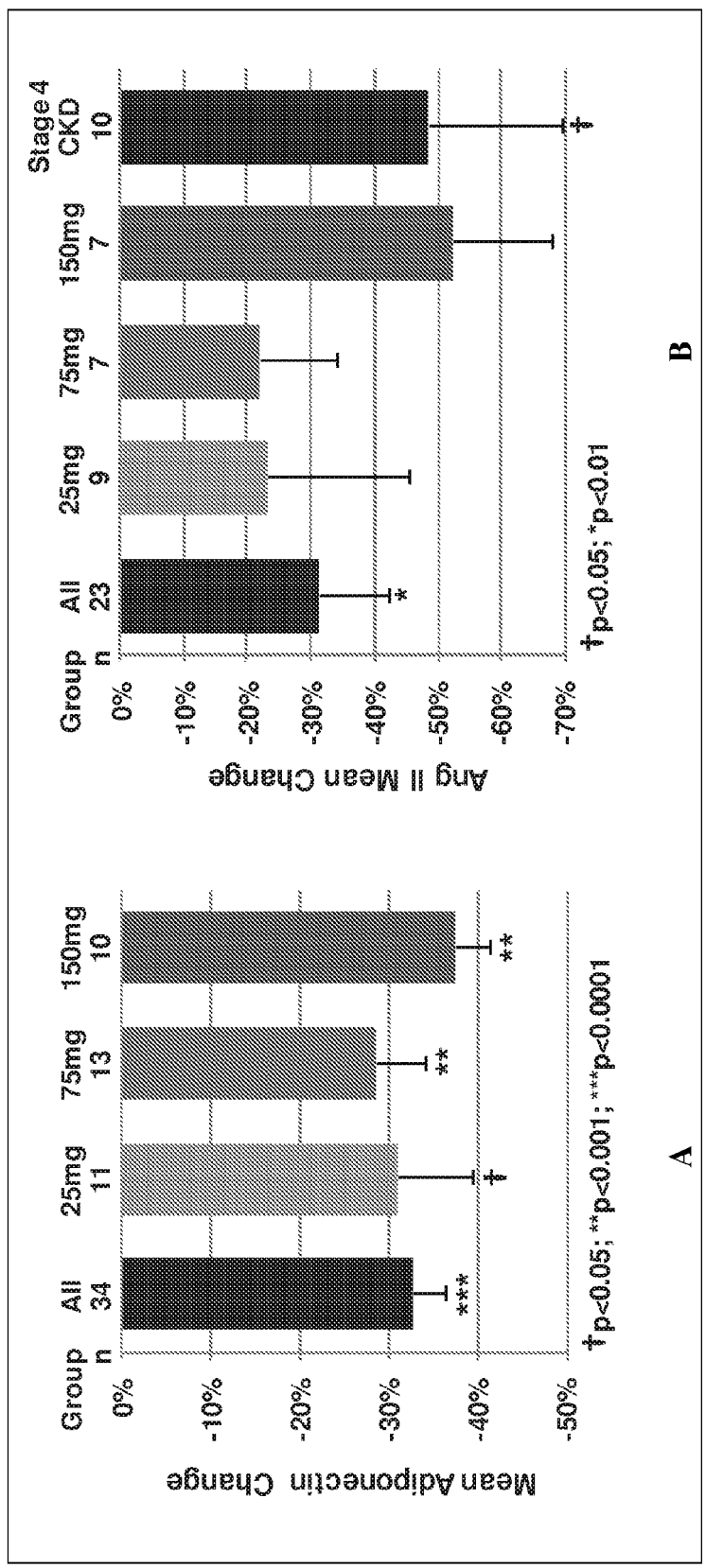
FIGS. 10A-B—Reduction of Markers of Diabetic Nephropathy Severity and Outcome. Improvements in Adiponectin (FIG. 10A) and Angiotensin II (FIG. 10B), which are elevated in diabetic nephropathy (DN) patients and correlate with renal disease severity. Adiponectin predicts all-cause mortality and end stage renal disease in DN patients. All available data included.
Figure 11:
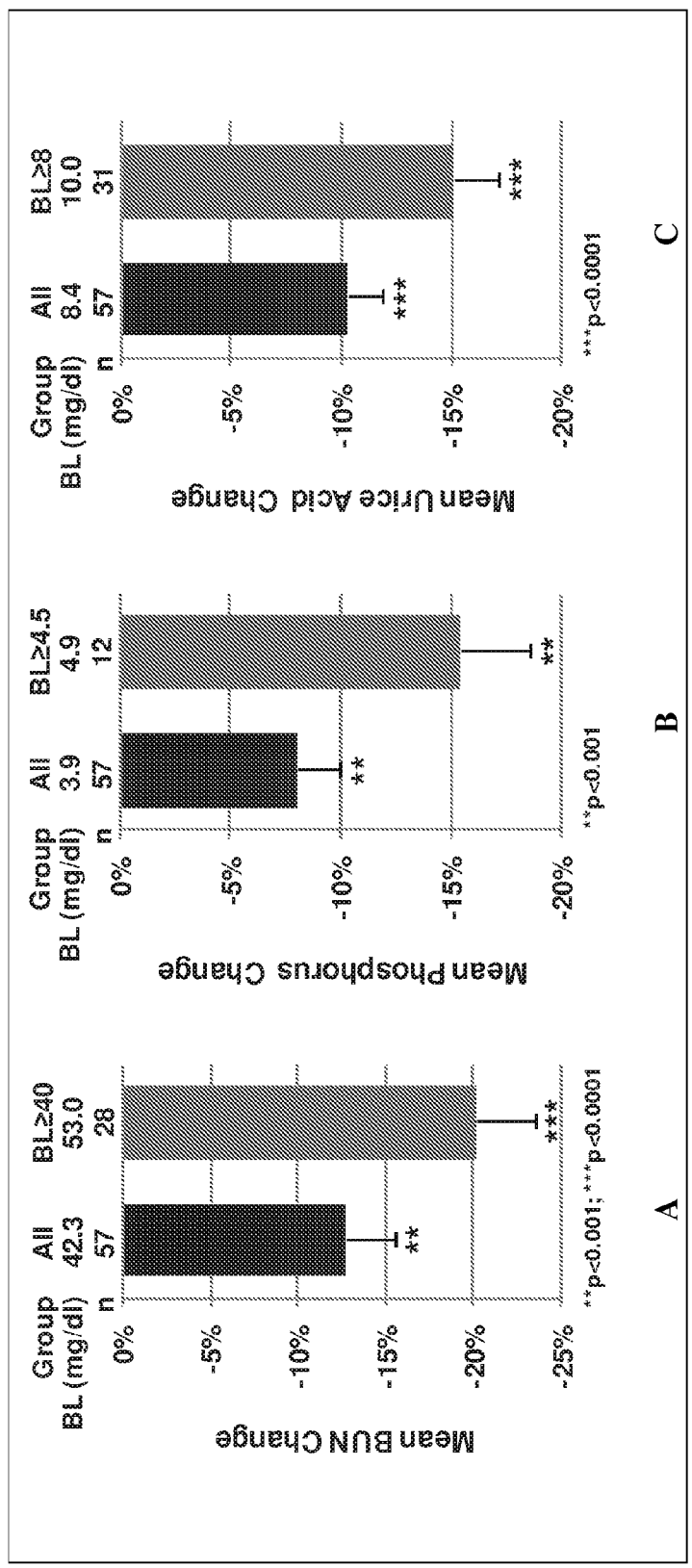
FIGS. 11A-C—RTA 402 Significantly Reduces Uremic Solutes. The graphs present mean changes in BUN (FIG. 11A), phosphorus (FIG. 11B), and uric acid (FIG. 11C) for all patients and for those patients showing elevated baseline values of a particular solute.

RTA 402 was shown to improve significantly eight measures of renal function and status, including serum creatinine based eGFR (FIG. 9), creatinine clearance, BUN (FIG. 11A), serum phosphorus (FIG. 11B), serum uric acid (FIG. 1 IC), Cystatin C, Adiponectin (FIG. 10A), and Angiotensin II (FIG. 10B). Adiponectin predicts all-cause mortality and end stage renal disease in DN patients. Adiponectin and Angiotensin II, which are elevated in DN patients, correlate with renal disease severity (FIGS. 10A-B). Effects on BUN, phosphorus, and uric acid are shown in FIGS. 11A-C.

Patients treated with higher doses (75 or 150 mg) of RTA 402 showed modest elevations (approximately 20 to 25%) in proteinuria. This is consistent with studies indicating that better GFR performance correlates with increased proteinuria. For example, in a long-term clinical study of more than 25,000 patients, treatment with ramipril (an ACE inhibitor) slowed the rate of eGFR decline more effectively than either telmisartan (an angiotensin receptor blocker) or the combination of ramipril and telmisartan (Mann et al., 2008). Conversely, proteinuria increased more in the ramipril group than in the other two groups. Major renal outcomes were also better with either drug alone than with combination therapy, although proteinuria increased least in the combination therapy group. Other studies have shown that drugs that reduce GFR, such as ACE-inhibitors, also reduce proteinuria (Lozano et al., 2001; Sengul et al., 2006). Other studies have shown that drugs that acutely increase GFR, such as certain calcium channel blockers, increase proteinuria up to 60% during short-term dosing (Agodoa et al., 2001; Viberti et al., 2002).

All of the compositions and/or methods disclosed and claimed herein can be made and executed without undue experimentation in light of the present disclosure. While the compositions and methods of this invention have been described in terms of preferred embodiments, it will be apparent to those of skill in the art that variations may be applied to the compositions and/or methods and in the steps or in the sequence of steps of the method described herein without departing from the concept, spirit and scope of the invention. More specifically, it will be apparent that certain agents which are both chemically and physiologically related may be substituted for the agents described herein while the same or similar results would be achieved. All such similar substitutes and modifications apparent to those skilled in the art are deemed to be within the spirit, scope and concept of the invention as defined by the appended claims.

IX. References

The following references, to the extent that they provide exemplary procedural or other details supplementary to those set forth herein, are specifically incorporated herein by reference.

U.S. Pat. No. 6,025,395
U.S. Pat. No. 6,326,507
U.S. Pat. No. 6,974,801
U.S. Patent Prov. 60/955,939
U.S. patent application Ser. No. 12/191,176
Agodoa et al., *JAMA*, 285:2719-2728, 2001.
Ahmad et al., *J. Biol. Chem.*, 281:3576-3579, 2006.
Aschner et al., *Diabetes Care*, 29(12):2632-2637, 2006.
Blann et al., *Thromb. Haemost.*, 93: 228-35 (2005).
DeFronzo et al., *Am. J. Physiol.*, 237(3):E214-223, 1979.
Dinkova-Kostova et al., *Proc. Natl. Acad. Sci. USA*, 102(12): 4584-4589, 2005.
Goldstein et al., *Diabetes Care*, 30(8):1979-1987, 2007.
Goodman et al., *Kidney Int.*, 72:945-953, 2007.
Honda et al., *Bioorg. Med. Chem. Lett.*, 12:1027-1030, 2002.
Honda et al., *Bioorg. Med. Chem. Lett.*, 19:2711-2714, 1998.
Honda et al., *Bioorg. Med. Chem. Lett.*, 9:3429-3434, 1999.
Honda et al., *J. Med. Chem.*, 43:1866-1877, 2000a.
Honda et al., *J. Med. Chem.*, 43:4233-4246, 2000b.
Honda et al., *Med. Chem. Lett.*, 7:1623-1628, 1997.
Honda et al., *Org. Biomol. Chem.*, 1:4384-4391, 2003.
Huang et al., *Cancer Res.*, 54:701-708, 1994.
Ikeda et al., *Cancer Res.*, 63: 5551-5558, 2003.
Ikeda et al., *Mol. Cancer. Ther.*, 3:39-45, 2004.
Kobayashi & Yamamoto, *Antioxid. Redox. Signal.*, 7:385-394, 2005.
Liby et al., *Cancer Res.*, 65:4789-4798, 2005.
Liu, *J. Ethnopharmacol.*, 49:57-68, 1995.
Lozano et al., *Nephrol. Dial. Transplant.*, 16-[Suppl 1]:85-89, 2001.
Ma et al., *Am. J. Pathol.*, 168:1960-1974, 2006.
Mann et al., *The Lancet*, 372: 547-553, 2008.
Maines & Gibbs, *Biochem. Biophys. Res. Commun.*, 338: 568-577, 2005.
Minns et al., *Gastroenterology*, 127:119-26, 2004.
Mix et al., *Mol. Pharmacol.*, 65:309-318, 2004.
Nath, *Kidney Int.*, 70, 432-443, 2006.
Nichols, *Drug News Perspect.*, 17:99-104, 2004.

Nishino et al., *Cancer Res.*, 48:5210-5215, 1988.
Place et al., *Clin. Cancer Res.*, 9:2798-2806, 2003.
Pullman et al., *Vasc. Health Risk Manag.*, 2(3):203-212, 2006.
Repka, M A, McGinity, J W, Zhang, F, Koleng, J J, Hot-melt extrusion technology. In: *Enclopedia of Pharmaceutical Technology*, 2nd ed, New York, N.Y.: Marcel Dekker, 2002: 203-206.
Sengul et al., *Diab. Res. Clin. Pract.*, 71:210-219, 2006.
Shishodia et al., *Clin. Cancer Res.*, 12(6):1828-1838, 2006.
Suh et al., *Cancer Res.*, 63:1371-1376, 2003.
Suh et al., *Cancer Res.*, 58:717-723, 1998.
Suh et al., *Cancer Res.*, 59(2):336-341, 1999.
Tumlin et al., *Am. J. Cardiol.*, 98:14 K-20K, 2006.
Viberti et al., *Circulation*, 106:672-678, 2002.
Wang et al., *Mol. Endocrinol.*, 14:1550-1556, 2000.
Wardle, *Nephrol. Dial. Transplant.*, 16, 1764-1768 2001.
Wermuth and Stahl, In: *Pharmaceutical Salts: Properties, Selection and Use—A Handbook*, Verlag Helvetica Chimica Acta, 2002.
Yao et al., *Am. J. Med. Sci.*, 334(2):115-24, 2007.
Yates et al., *Mol. Cancer. Ther.*, 6(1):154-162, 2007.
Yoh et al., *Kidney Int.*, 60, 1343-1353, 2001.
Zingarelli et al., *Crit. Care Med.*, 31, S105-S111, 2003.
Zoccali, *J. Amer. Soc. Nephrol.*, 17:S61-S-63, 2006.

What is claimed is:

1. A method of improving kidney function in a subject in need thereof comprising administering to the subject a compound of the formula,

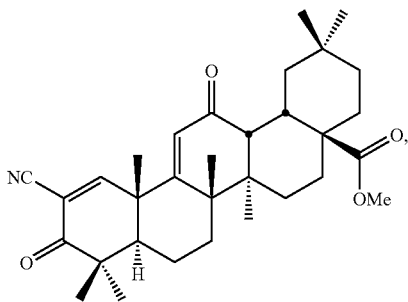

in an amount sufficient to improve kidney function.

2. The method of claim 1, where the subject has chronic kidney disease (CKD) or exhibits one or more symptoms of CKD.

3. The method of claim 2, where the subject has been identified as having CKD.

4. The method of claim 2, where the CKD is characterized by a serum creatinine level of 1.3-3.0 mg/DL where the subject is a human female or a serum creatinine level of 1.5-3.0 mg/DL where the subject is a human male.

5. The method of claim 2, where the CKD is stage 4.

6. The method of claim 1, where the subject has diabetic nephropathy (DN) or exhibits one or more symptoms of DN.

7. The method of claim 6, where the subject has been identified as having DN.

8. The method of claim 1, where the administering results in an improvement in estimated glomerular filtration rate (eGFR) of the subject.

9. The method of claim 8, where the administering reduces the level of serum creatinine in the subject.

10. The method of claim 9, where the level of serum creatinine in the blood of the subject has been measured.

11. The method of claim 1, where the level of blood urea nitrogen (BUN) in the subject has been measured.

12. The method of claim 1, where the level of Adiponectin in the blood of the subject has been measured.

13. The method of claim 1, where the level of Angiotensin II in the subject has been measured.

14. The method of claim 1, where the subject has insulin resistance or exhibits one or more symptoms of insulin resistance.

15. The method of claim 14, where the subject has been identified as having insulin resistance.

16. The method of claim 14, where the level of hemoglobin Alc in the subject has been measured.

17. The method of claim 14, where a blood sugar level of the subject has been measured.

18. The method of claim 14, where the administering reduces the level of hemoglobin Alc or fasting blood glucose in the subject.

19. The method of claim 17, where a fasting glucose level of the subject has been measured.

20. The method of claim 14, where the insulin sensitivity of the subject has been measured by a hyperinsulinemic euglycemic clamp test.

21. The method of claim 14, where a glucose disposal rate (GDR) in the subject has been measured.

22. The method of claim 1, where the subject has cardiovascular disease (CVD) or exhibits one or more symptoms of CVD.

23. The method of claim 22, where the subject has been identified as having CVD.

24. The method of claim 22, where the level of a marker of CVD in the subject has been measured.

25. The method of claim 22, where the number of circulating endothelial cells (CFCs) in the blood of the subject has been measured.

26. The method of claim 25, where the CECs are iNOS-positive circulating endothelial cells.

27. The method of claim 22, where the administering reduces the level of circulating endothelial cells in the subject.

28. The method of claim 27, where the administering reduces the level of hemoglobin Alc or fasting blood glucose in the subject.

29. The method of claim 1, wherein the subject is a human.

30. The method of claim 1, wherein at least a portion of the compound is present as a crystalline form having an X-ray diffraction pattern (CuKα) comprising significant diffraction peaks at about 8.8, 12.9, 13.4, 14.2 and 17.4 °2θ.

31. The method of claim 30, wherein the X-ray diffraction pattern (CuKα) is substantially as shown in FIG. 12A or FIG. 12B.

32. The method of claim 30, wherein the pharmaceutically effective amount is a daily dose of about 10 mg to about 200 mg of the compound.

33. The method of claim 1, wherein at least a portion of the compound is present as an amorphous form having an X-ray diffraction pattern (CuKα) with a halo peak at approximately 13.5 °2θ, substantially as shown in FIG. 12C, and a $T_g$ from about 120 ° C. to about 135 °C.

34. The method of claim 33, wherein the $T_g$ is from about 125 ° C. to about 130 ° C.

35. The method of claim 33, wherein the pharmaceutically effective amount is a daily dose from about 0.1 mg to about 30 mg of the compound.

36. The method of claim 1, where the compound is administered orally, intraarterially or intravenously.

37. The method of claim 1, where the compound is formulated as a hard or soft capsule or a tablet.

38. The method of claim 1, wherein the compound is formulated as a solid dispersion comprising (i) the compound and (ii) an excipient.

39. The method of claim 38, wherein the excipient is a methacrylic acid-ethyl acrylate copolymer (1:1).

40. A method of improving kidney function in a subject comprising administering to the subject a compound of the formula,

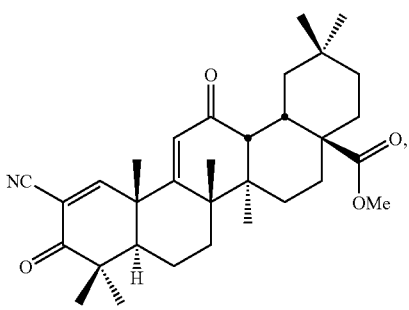

in an amount sufficient to improve kidney function, wherein:
(a) at least a portion of the compound is present as an amorphous form having an X-ray diffraction pattern (CuKα) with a halo peak at approximately 13.5 °2θ, substantially as shown in FIG. 12C, and a $T_g$ from about 120 ° C. to about 135 ° C.; and
(b) where the subject has been identified as having chronic kidney disease (CKD).

* * * * *

UNITED STATES PATENT AND TRADEMARK OFFICE
CERTIFICATE OF CORRECTION

PATENT NO.        : 8,129,429 B2
APPLICATION NO.   : 12/352473
DATED             : March 6, 2012
INVENTOR(S)       : Michael B. Sporn et al.

It is certified that error appears in the above-identified patent and that said Letters Patent is hereby corrected as shown below:

In claim 25, column 44, line 43, delete "(CFCs)" and insert --(CECs)-- therefor.

Signed and Sealed this
First Day of May, 2012

David J. Kappos
*Director of the United States Patent and Trademark Office*